(12) United States Patent
Cheshire et al.

(10) Patent No.: US 6,887,871 B2
(45) Date of Patent: May 3, 2005

(54) USE OF PHENYLHETEROAKYLAMINE DERIVATIVES

(75) Inventors: David Cheshire, Leics (GB); Stephen Connolly, Leics (GB); David Cox, Leics (GB); Peter Hamley, Leics (GB); Antonio Mete, Leics (GB); Austen Pimm, Leics (GB)

(73) Assignee: AstraZeneca AB, Södertälje (SE)

( * ) Notice: Subject to any disclaimer, the term of this patent is extended or adjusted under 35 U.S.C. 154(b) by 1 day.

(21) Appl. No.: 10/204,742

(22) PCT Filed: Feb. 20, 2001

(86) PCT No.: PCT/SE01/00373

§ 371 (c)(1),
(2), (4) Date: Oct. 18, 2002

(87) PCT Pub. No.: WO01/62704

PCT Pub. Date: Aug. 30, 2001

(65) Prior Publication Data

US 2003/0158185 A1 Aug. 21, 2003

(30) Foreign Application Priority Data

Feb. 23, 2000 (GB) .............................................. 0004153

(51) Int. Cl.$^7$ .................. A61K 31/535; A61K 31/4965; A61K 31/42; A01N 43/76; A01N 43/50
(52) U.S. Cl. .................... 514/237.8; 514/256; 514/374; 514/385; 514/438; 514/646; 544/335; 544/336; 546/208; 546/209; 546/210; 546/213; 546/214; 546/248; 546/334; 548/305; 548/247; 548/341.1; 549/75; 549/491; 549/497; 564/346
(58) Field of Search ............................. 514/237.8, 252, 514/256, 374, 385, 438, 646; 544/335, 336; 546/208, 209, 210, 213, 214, 248, 334; 548/305, 247, 341.1, 205; 549/75, 491, 497; 564/346

(56) References Cited

U.S. PATENT DOCUMENTS

| | | | | |
|---|---|---|---|---|
| 4,296,126 A | 10/1981 | Nedelec et al. | ............. | 424/316 |
| 4,314,081 A | 2/1982 | Molloy et al. | ............... | 564/347 |
| 4,666,910 A | 5/1987 | Schneider et al. | .......... | 514/228 |
| 4,902,710 A | 2/1990 | Foster et al. | ................. | 514/438 |
| 2003/0139350 A1 | 7/2003 | Larsen et al. | ................. | 514/25 |

FOREIGN PATENT DOCUMENTS

| | | |
|---|---|---|
| DE | 29 07 217 A1 | 8/1979 |
| EP | 0 318 727 A2 | 6/1989 |
| EP | 0 273 658 B1 | 10/1990 |
| EP | 0 399 504 A2 | 11/1990 |
| EP | 0 515 240 A1 | 11/1992 |
| EP | 0 571 685 A1 | 12/1993 |
| EP | 0 576 766 A1 | 1/1994 |
| EP | 0 661 266 A1 | 7/1995 |
| EP | 0 707 007 A1 | 4/1996 |
| GB | 765849 | 1/1957 |
| GB | 922600 | 4/1963 |
| GB | 1014348 | 12/1965 |
| GB | 2 060 620 A | 5/1981 |
| GB | 2 060 621 | 5/1981 |
| GB | 2 060 622 A | 5/1981 |
| JP | 51044934 B4 | 12/1976 |
| JP | 52-941 * | 1/1977 |
| JP | 52000941 B4 | 1/1977 |
| WO | WO 92/19210 | 11/1992 |
| WO | WO 99/10339 | 3/1999 |
| WO | WO 99/11620 | 3/1999 |
| WO | WO 99/38514 | 8/1999 |
| WO | WO 99/62883 | 12/1999 |
| WO | WO 00/27842 | 5/2000 |
| WO | WO 00/58305 | 10/2000 |
| WO | WO 02/20484 | 3/2002 |
| WO | WO 02/30899 | 4/2002 |

OTHER PUBLICATIONS

S.J. Yan, et al., "Potential causal prophylactic antimalarial agents. Synthesis of quinoxaline, benzimidazole, and alkoxybenzene derivatives containing a novoldiamine moiety." J. Heterocycl. Chem. 297–300, (1978).

Chemical Abstracts, CAPLUS accession no. 1998: 394854 (Zhongguo Yaoke Daxue Xuebao, 1998, 29, 81–91).

Chemical Abstracts, CAPLUS accession no. 1968: 28182 (J. Med. Chem., 1968, 11, 95–97).

(Continued)

*Primary Examiner*—Richard L. Raymon
*Assistant Examiner*—Zachary C. Tucker
(74) *Attorney, Agent, or Firm*—Fish & Richardson P.C.

(57) ABSTRACT

There is disclosed the use of a compound of formula (I) wherein $R^1$, $R^2$, X, Y, V, W and Z are as defined in the specification, and pharmaceutically acceptable salts, enantiomers or racemates thereof, in the manufacture of a medicament, for the treatment or prophylaxis of diseases or conditions in which inhibition of nitric oxide synthase activity is beneficial. Certain novel compounds of formula (Ia) and pharmaceutically acceptable salts thereof, and enantiomers and racemates thereof are disclosed; together with processes for their preparation, compositions containing them and their use in therapy. The compounds of formulae (I) and (Ia) are inhibitors of the enzyme nitric oxide synthase and are thereby particularly useful in the treatment or prophylaxis of inflammatory disease.

(I)

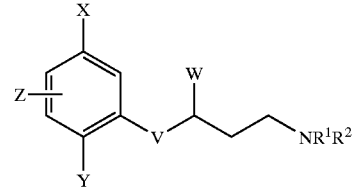

6 Claims, No Drawings

OTHER PUBLICATIONS

Chemical Abstracts, CAPLUS accession no. 1997: 534782 (Zhongguo Yaoke Huaxue Zazhi, 1997, 7, 1–8).
Chemical Abstracts, CAPLUS accession no. 1999: 659361 (WO 99/51575).
Chemical Abstracts, CAPLUS accession no. 1967: 499505 (J. Chem. Soc. B, 1967, 859–866).
Chemical Abstracts, CAPLUS accession no. 1994: 579176 (Tetrahedron Letters, 1994, 35, 4585–4586).
Chemical Abstracts, CAPLUS accession no. 1968: 29366 (Probl. Poluch. Poluprod. Prom. Org. Sin., 1967, 90–97).
Chemical Abstracts, CAPLUS accession no. 1995: 664999 (DE 4 331 179).
Chemical Abstracts, CAPLUS accession no. 1995: 913361 (WO 95/15954).
Chemical Abstracts, CAPLUS accession no. 1981: 121503 (DE 2 905 877).
Chemical Abstracts, CAPLUS accession no. 1990: 35674 (JP A2 01168666).
Chemical Abstracts, CAPLUS accession no. 1978: 169760 (JP A2 52153922).
Chemical Abstracts, CAPLUS accession no. 1977: 189458 (JP B4 51 44934).
Chemical Abstracts, CAPLUS accession no. 1996: 113480 (SU 1824396).
Chemical Abstracts, 1965, vol. 62, 16781 (J. Med. Chem. 1965, 8, 356–367).
Chemical Abstracts, 1958, vol. 52, 11069 (J. Am. Chem. Soc., 1958, 80, 162–164).
Chemical Abstracts, 1966, vol. 65, 2181 (Neth. Appln. 6,508,754).

* cited by examiner

USE OF PHENYLHETEROAKYLAMINE DERIVATIVES

CROSS REFERENCE TO RELATED APPLICATIONS

The present application is a national phase application under 35 U.S.C. Section 371 filed from International Patent Application PCT/SE01/00373, filed 20 Feb. 2001, which claims priority to United Kingdom patent application Serial. No. 0004153.3, filed 23 Feb. 2000. The contents of these applications are incorporated herein by reference in their entirety.

FIELD OF THE INVENTION

The present invention relates to the use of phenylheteroalkylamine derivatives as inhibitors of the enzyme nitric oxide synthase. Certain novel phenylheteroalkylamine derivatives are also disclosed together with processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, Ann. Rep. Med. Chem., 1996, 31, 221–230).

Considerable effort has been expended in efforts to identify compounds that act as specific inhibitors of one or more isoforms of the enzyme nitric oxide synthase. The use of such compounds in therapy has also been widely claimed.

Patent application EP 0 273 658 discloses compounds of formula

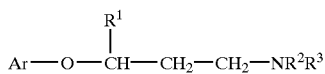

wherein Ar represents phenyl optionally substituted by halogen, C1 to 4 alkyl, C1 to 3 alkoxy or $CF_3$, or optionally substituted naphthyl; $R^1$ represents C5 to 7 cycloalkyl, thienyl, halothienyl, (C1 to 4 alkyl)-substituted-thienyl, furanyl, pyridyl or thiazolyl; and $R^2$ and $R^3$ are each independently H or methyl. Said compounds are potent and selective inhibitors of serotonin and norepinephrine uptake and are thereby stated to be useful in the treatment of human diseases such as anxiety, depression and obesity.

U.S. Pat. No. 4,314,081 discloses compounds of formula

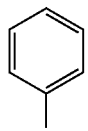

wherein Ar represents phenyl optionally substituted by halogen, C1 to 4 alkyl, C1 to 3 alkoxy or C3 to 4 alkenyl; or Ar represents naphthyl; and $R^1$, $R^2$ and $R^3$ are each independently H or methyl. Said compounds are potent and selective inhibitors of serotonin and norepinephrine uptake and are thereby stated to be useful in the treatment of human diseases such as depression and obesity.

Patent application WO 92/19210 discloses compounds of formula

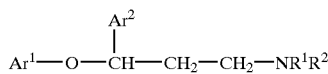

wherein $Ar^1$ and $Ar^2$ independently represent phenyl optionally substituted by various substituents but with the proviso that at least one of $Ar^1$ and $Ar^2$ is substituted by at least one halogen atom; and $R^1$ and $R^2$ are each independently H or C1 to 4 alkyl. Said compounds are stated to be useful for imaging neurotransmitter re-uptake systems in the brain.

Patent application DE 29 07 217 discloses compounds of formula

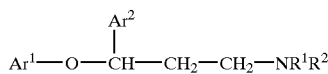

wherein $Ar^1$ represents phenyl substituted by nitro and optionally substituted by a second substituent selected from Cl, Br, $CF_3$, Me or OMe; $Ar^2$ represents phenyl optionally substituted by Cl, Br or F; $R^1$ represents H or C1 to 5 alkyl; and $R^2$ represents C1 to 5 alkyl. The compounds are stated to be useful in the treatment of eating disorders and depression.

Patent application GB 2 060 620 discloses compounds of formula

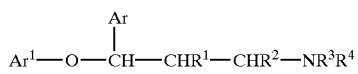

wherein $Ar^1$ represents phenyl optionally substituted by C1 to 6 alkyl, C2 to 6 alkenyl, $CF_3$, halogen, nitro, amino or acylamino; Ar represents phenyl substituted by at least one group selected from C1 to 6 alkyl, C1 to 6 alkoxy, $CF_3$, nitro or amino; $R^1$, $R^2$ and $R^4$ independently represent H or C1 to 6 alkyl; and $R^3$ represents H, C1 to 6 alkyl or benzyl. The compounds are claimed to be useful as antidepressants.

Patent application GB 2 060 621 discloses compounds of formula

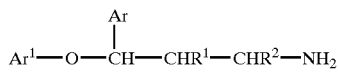

wherein Ar represents phenyl optionally substituted by C1 to 6 alkyl or halogen; $Ar^1$ represents phenyl substituted by $NO_2$, amino or acylamino; $R^1$ and $R^2$ independently represent H or C1 to 6 alkyl. The compounds are claimed to be useful as antidepressants.

Patent application EP 3 18 727 discloses compounds of formula

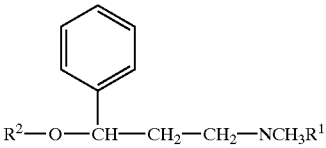

wherein $R^1$ can represent optionally substituted alkyl or cycloalkyl and $R^2$ can represent optionally substituted phenyl. The compounds prevent calcium overload in brain cells and are thus useful in the treatment of anoxia, migraine, ischaemia and epilepsy.

Patent application EP 399 504 discloses compounds of formula

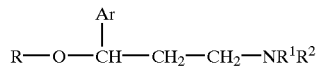

wherein Ar represents optionally substituted phenyl; R can also represent optionally substituted phenyl; and $R^1$ and $R^2$ can represent optionally substituted alkyl or cycloalkyl. The compounds prevent calcium overload in brain cells and are thus useful in the treatment of anoxia, migraine, ischaemia and epilepsy.

Patent application EP 576 766 discloses compounds of formula

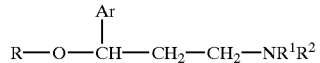

wherein Ar represents optionally substituted phenyl; R can also represent optionally substituted phenyl; $R^1$ and $R^2$ can represent optionally substituted alkyl or cycloalkyl; or the group $NR^1R^2$ represents a 5 to 7 membered ring, optionally further substituted. The compounds prevent calcium overload in brain cells and are thus useful in the treatment of anoxia, traumatic injury, neurodegenerative diseases, migraine, ischaemia and epilepsy.

Patent application EP 571 685 discloses compounds similar to those of EP 576 766 but wherein Ar represents optionally substituted furanyl, thienyl or pyrrolyl.

The present invention relates to the surprising finding that a group of phenylheteroalkylamine derivatives, including some compounds that are within the generic scopes of some of the above background art documents, are inhibitors of the enzyme nitric oxide synthase.

DISCLOSURE OF THE INVENTION

According to the present invention, there is provided the use of a compound of formula (I)

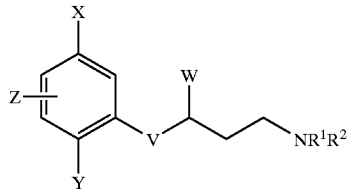

wherein:
X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;
m and p independently represent an integer 0, 1 or 2;
Z represents H or fluoro;
V represents O;
W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;
$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;
or the group $NR^1R^2$ together represents part of a five membered aromatic azacyclic ring optionally incorporating one further N atom;
$R^4$, $R^5$, $R^6$, $R^7$, $R^9$ and $R^{10}$ independently represent H or C1 to 4 alkyl;
$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
$R^{11}$ and $R^{12}$ independently represent H or C1 to 4 alkyl;
or a pharmaceutically acceptable salt, enantiomer or racemate thereof, in the manufacture of a medicament, for the treatment or prophylaxis of diseases or conditions in which inhibition of nitric oxide synthase activity is beneficial.

In another aspect the invention provides the use of a compound of formula (I) or a pharmaceutically acceptable salt, enantiomer or racemate thereof, in the manufacture of a medicament, for the treatment or prophylaxis of diseases or conditions in which inhibition of the inducible isoform of the enzyme nitric oxide synthase activity is beneficial.

A more particular aspect of the invention provides the use of a compound of formula (I) or a pharmaceutically acceptable salt, enantiomer or racemate thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer or racemate thereof.

Further, according to the invention, there is also provided a method of treating, or reducing the risk of, diseases or conditions in which inhibition of the activity of the inducible isoform of the enzyme nitric oxide synthase is beneficial, which comprises administering to a person suffering from or at risk of, said disease or condition, a therapeutically effective amount of a compound of formula (I) or a pharmaceutically acceptable salt, enantiomer or racemate thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer or racemate thereof.

In another aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of diseases or conditions in which inhibition of nitric oxide synthase activity is beneficial.

In another preferred aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of diseases or conditions in which inhibition of the inducible isoform of the enzyme nitric oxide synthase activity is beneficial.

In another more particular aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of inflammatory disease.

The compounds of formula (I) may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer or racemate thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer or racemate thereof in combination with a COX-2 inhibitor.

In one preferred embodiment, X and Y independently represent Br, Cl, $CH_3$, $CF_3$ or CN. It is particularly preferred that X represents Br, Cl or $CF_3$. It is also particularly preferred that Y represents Cl or CN.

Preferably, W represents an optionally substituted five or six membered aromatic heterocyclic ring containing 1 to 3 heteroatoms independently selected from O, S and N. Particular examples are those wherein W represents thienyl, furyl, pyridyl, thiazolyl, oxazolyl, isoxazolyl or pyrimidyl.

Preferably, $R^1$ and $R^2$ independently represent H or C1 to 4 alkyl optionally substituted by C1 to 4 alkoxy or hydroxy. More preferably, $R^1$ and $R^2$ independently represent H or methyl.

The use of the following compounds of formula (I) and pharmaceutically acceptable salts, enantiomers or racemates thereof is specifically included within the invention:

2-(3-amino-1-phenylpropoxy)-4-chlorobenzonitrile;

4-chloro-2-(3-(methylamino)-1-phenylpropoxy) benzonitrile;

4-bromo-2-[(1R)-3-(Methylamino)-1-phenylpropoxy] benzonitrile;

γ-R-(2-bromo-5-chlorophenoxy)-N-methylbenzenepropanamine;

4-chloro-2-{[(1R)-3-chloro-1-phenylpropyl] oxy}benzonitrile;

4-methoxy-2-[3-(methylamino)-1-phenylamino-1-phenylpropoxy]benzonitrile;

4-methyl-2-{[(1R)-3-(methylamino)-1-phenylpropyl] oxy}benzonitrile;

R-γ-(2,5-dichlorophenoxy)-N-methyl-2-thiophenepropanainine;

S-γ-(2,5-dichlorophenoxy)-N-methyl-2-thiophenepropanamine;

2-[[(3R)-3-(2,5-dichlorophenoxy)-3-(2-thienyl)propyl] amino]ethanol;

4-chloro-2-{[(1R)-3-(4-methyl-1-piperazinyl)-1-phenylpropyl]oxy}-benzonitrile;

4-chloro-2-{[(1R)-3-(4-hydroxy-1-piperidinyl)-1-phenylpropyl]oxy}-benzonitrile;

4-chloro-2-{[(1R)-3-[(2-hydroxyethyl)methylamino]-1-phenylpropyl]oxy}-benzonitrile;

4-chloro-2-{[(1R)-3-(4-morpholinyl)-1-phenylpropyl] oxy}-benzonitrile;

4-chloro-2-{[(1R)-3-[(3R)-3-hydroxypyrrolidinyl]-1-phenylpropyl]oxy}-benzonitrile;

4-chloro-2-{[(1R)-3-[(3S)-3-hydrokypyrrolidinyl]-1-phenylpropyl]oxy}-benzonitrile;

2-{[(1R)-3-amino-1-phenylpropyl]oxy}-5-fluoro-4-methylbenzonitrile;

4-chloro-5-fluoro-2-[3-(methylamino)-1-(2-pyrimidinyl) propoxy]benzonitrile;

4-chloro-5-fluoro-2-({(1R)-1-(3-furanyl)-3-[(2-methoxyethyl)amino]propyl}oxy)benzonitrile;

4-methoxy-2-[[(1R)-3-(methylamino)-1-phenylpropyl] oxy]-benzonitrile;

γ-(2-bromo-5-fluorophenoxy)-N-methyl-benzenepropanamine;

(R)-γ-(5-bromo-2-chlorophenoxy)-N-methylbenzenepropanamine;

(R)-γ-(2-bromo-5-nitrophenoxy)-N-methylbenzenepropanamine;

4-chloro-5-fluoro-2-[[(1R)-3-[(2-methoxyethyl)amino]-1-phenylpropyl]oxy]-benzonitrile;
4-chloro-2-{[(1R)-3-(cyclopropylamino)-1-phenylpropyl]oxy}-5-fluorobenzonitrile;
4-chloro-2-{[(1R)-3-(cyclopropylamino)-1-(3-furanyl)propyl]oxy}-5-fluorobenzonitrile;
4-chloro-2-{[(1R)-3-(cyclopropylamino)-1-(3-thienyl)propyl]oxy}-5-fluorobenzonitrile;
4-bromo-2-{[(1R)-3-(cyclopropylamino)-1-(phenyl)propyl]oxy}-5-fluorobenzonitrile;
4-bromo-2-{[(1R)-3-(cyclopropylamino)-1-(3-furanyl)propyl]oxy}-5-fluorobenzonitrile;
4-bromo-2-{[(1R)-3-(cyclopropylamino)-1-(3-thienyl)propyl]oxy}-5-fluorobenzonitrile;
4-chloro-5-fluoro-2-({(1R)-3-[(3-hydroxypropyl)amino]-1-phenylpropyl}oxy)benzonitrile;
4-chloro-5-fluoro-2-[[(1R)-1-(3-furanyl)-3-(3-hydroxypropyl)amino]propyl]oxy}benzonitrile;
4-chloro-5-fluoro-2-{[(1R)-3-[(3-hydroxypropyl)amino]-1-(3-thienyl)propyl]oxy}benzonitrile;
4-bromo-5-fluoro-2-({(1R)-3-[(3-hydroxypropyl)amino]-1-phenylpropyl}oxy)benzonitrile;
4-bromo-5-fluoro-2-({(1R)-1-(3-furanyl)-3-[(3-hydroxypropyl)amino]propyl}oxy)benzonitrile;
4-bromo-5-fluoro-2-{[(1R)-3-[(3-hydroxypropyl)amino]-1-(3-thienyl)propyl]oxy}benzonitrile;
2-[[(1R)-3-amino-1-phenylpropyl]oxy]-4-(trifluoromethyl)benzonitrile;
2-[[(1R)-3-amino-1-phenylpropyl]oxy]-4-chlorobenzonitrile;
4-chloro-5-fluoro-2-[[(1R)-3-(methylamino)-1-phenylpropyl]oxy]benzonitrile;
2-[[(1R)-3-amino-1-phenylpropyl]oxy]-4-chloro-5-fluorobenzonitrile;
γ-[5-chloro-2-(trifluoromethyl)phenoxy]-N-methylbenzenepropanamine;
2-[[(1R)-3-(methylamino)-1-phenylpropyl]oxy]-4-(trifluoromethyl)benzonitrile;
4-chloro-5-fluoro-2-[[(1R)-3-[[(5-methylpyrazinyl)methyl]amino]-1-phenylpropyl]oxy]benzonitrile;
4-chloro-5-fluoro-2-[[(1R)-3-[(1H-imidazol-2-ylmethyl)amino]-1-phenylpropyl]oxy]benzonitrile;
4-chloro-2-[[(1R)-3-[[2-(dimethylamino)ethyl]amino]-1-phenylpropyl]oxy]-5-fluoro benzonitrile;
4-chloro-5-fluoro-2-[[(1R)-3-[[2-(4-morpholinyl)ethyl]amino]-1-phenylpropyl]oxy]benzonitrile;
4-chloro-5-fluoro-2-[[(1R)-3-[[2-(1H-imidazol-1-yl)ethyl]amino]-1-phenylpropyl]oxy]benzonitrile;
4-chloro-5-fluoro-2-[[(1R)-3-[[2-(1H-imidazol-4-yl)ethyl]amino]-1-phenylpropyl]oxy]benzonitrile;
4-chloro-5-fluoro-2-[[(1R)-3-[(2-hydroxyethyl)amino]-1-phenylpropyl]oxy]benzonitrile;
2-[[(1R)-3-[(2-aminoethyl)amino]-1-phenylpropyl]oxy]-4-chloro-5-fluorobenzonitrile;
4-chloro-5-fluoro-2-[[(1R)-1-phenyl-3-[(3,3,3-trifluoropropyl)amino]propyl]oxy]benzonitrile;
2-{[(1R)-3-amino-1-(2-thiazolyl)propyl]oxy}-4-chlorobenzonitrile;
4-chloro-2-{[(1R)-3-(methylamino)-1-(2-thiazolyl)propyl]oxy}benzonitrile;
(R)-γ-(2,5-dichlorophenoxy)-2-thiazolepropanamine;
2-[3-amino-1-(2-oxazolyl)propoxy]-4-chlorobenzonitrile;
γ-(2,5-dichlorophenoxy)-2-oxazolepropanamine;
2-[[-3-amino-1-(3-pyridinyl)propyl]oxy]-4-chloro-5-fluorobenzonitrile;
4-chloro-5-fluoro-2-[3-(methylamino)-1-(3-pyridinyl)propoxy]benzonitrile;
γ-[2-chloro-5-(trifluoromethyl)phenoxy]-3-pyridinepropanamine;
2-[3-amino-1-(6-methoxy-2-pyridinyl)propoxy]-4-chloro-5-fluorobenzonitrile;
2-[3-amino-1-(1,6-dihydro-6-oxo-2-pyrdinyl)propoxy]-4-chloro-5-fluorobenzonitrile;
2-[3-amino-1-(6-bromo-3-pyridinyl)propoxy]-4-chlorobenzonitrile;
2-[[3-amino-1-(5-isoxazolyl)propyl]oxy]-4-chlorobenzonitrile;
4-chloro-2-[3-[(2-hydroxyethyl)amino]-1-(5-isoxazolyl)propoxy]benzonitrile;
(R)-γ-(2,5-dichlorophenoxy)-5-isoxazolepropanamine;
(R)-γ-(2,5-dichlorophenoxy)-N-methyl-benzenepropanamine;
(R)-γ-[2-chloro-5-(trifluoromethyl)phenoxy]-N-methyl-benzenepropanamine;
4-chloro-2-[[(1R)-3-(methylamino)-1-(2-thienyl)propyl]oxy]benzonitrile;
2-[[(1R)-3-amino-1-(3-furanyl)propyl]oxy]-4-chloro-5-fluorobenzonitrile;
4-chloro-5-fluoro-2-[[(1R)-1-(3-furanyl)-3-methylamino)propyl]oxy]-benzonitrile;
4-chloro-5-fluoro-2-[[(1R)-3-(methylamino)-1-(3-thienyl)propyl]oxy]benzonitrile;
4-chloro-5-fluoro-2-[[(1R)-3-[(2-hydroxyethyl)amino]-1-(3-thienyl)propyl]oxy]benzonitrile;
2-[[(1R)-3-[(2-aminoethyl)amino]-1-(3-thienyl)propyl]oxy]-4-chloro-5-fluoro-benzonitrile;
2-[[(1R)-3-amino-1-(3-thienyl)propyl]oxy]-4-chloro-5-fluorobenzonitrile;
4-chloro-2-[3-(methylamino)-1-(2-thiazolyl)propoxy]-benzonitrile;
2-[[(1R)-3-amino-1-(2-thiazolyl)propyl]oxy]-4-chloro-5-fluoro-benzonitrile;
γ-(2-chloro-5-nitrophenoxy)-N-methylbenzenepropanamine;
(R)-γ-(5-chloro-2-nitrophenoxy)-N-methylbenzene)propanamine;
4-chloro-5-fluoro-2-{[(1R)-3-[(2-fluoroethyl)amino]-1-phenylpropyl]oxy}benzonitrile;
2-[[(1R)-3-amino-1-phenylpropyl]oxy]-4-bromo-5-fluorobenzonitrile;
3-[[(3R)-3-(2,5dichlorophenoxy)-3-phenylpropyl]amino]-1-propanol;
1-[(3R)-3-(2,5-dichlorophenoxy)-3-phenylpropyl]-4-piperidinemethanol;
N-[(3R)-3-(2,5-dichlorophenoxy)-3-phenylpropyl]-2-thiophenemethanamine;
N-[(3R)-3-(2,5-dichlorophenoxy)-3-phenylpropyl]-5-methyl-2-furanmethanamine;
4-chloro-2-[[(1R)-1-phenyl-3-(1-piperazinyl)propyl]oxy]benzonitrile;
5-fluoro-2-[[(1R)-3-[(2-hydroxyethyl)amino]-1-(3-isoxazolyl)propyl]oxy]-4-methyl-benzonitrile;

2-[[(1R)-3-amino-1-(3-isoxazolyl)propyl]oxy]-5-fluoro-4-methyl-benzonitrile;

4-chloro-2-[[(1R)-3-[(1,1-dimethylethyl)amino]-1-(3-isoxazolyl)propyl]oxy]benzonitrile;

2-[[(1R)-3-amino-1-(3-isoxazolyl)propyl]oxy]-4-chloro-benzonitrile;

2-[[(1R)-3-amino-1-(3-isoxazolyl)propyl]oxy]-4-chloro-5-fluoro-benzonitrile;

(R)-γ-(2,5-dichlorophenoxy)-3-isoxazolepropanamine;

2-[[(1R)-3-amino-1-(3-isoxazolyl)propyl]oxy]-4-(trifluoromethyl)-benzonitrile;

(R)-γ-[2-chloro-5-(trifluoromethyl)phenoxy]-2-pyridinepropanamine;

2-[[(1R)-3-amino-1-(5-methyl-3-isoxazolyl)propyl]oxy]-4-chloro-5-fluoro-benzonitrile.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

The term "C1 to 6 alkyl" is to be interpreted analogously.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

Examples of a "C1 to 4 alkyl or C1 to 4 alkoxy optionally further substituted by one or more fluorine atoms" include $CF_3$, $CF_3CF_2$, $CF_3CH_2$, $CH_2FCH_2$, $CH_3CF_2$, $CF_3CH_2CH_2$, $OCF_3$ and $OCH_2CF_3$.

Unless otherwise indicated, the term "halogen" referred to herein denotes fluoro, chloro, bromo and iodo.

Examples of a 4 to 8 membered saturated azacyclic ring optionally incorporating one further heteroatom selected from O, S or N include pyrrolidine, piperidine, piperazine, morpholine and perhydroazepine.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include pyrrolidine, tetrahydrofuran, piperidine and piperazine.

Examples of a five membered aromatic azacyclic ring optionally incorporating one further N atom include pyrrole and imidazole.

Certain compounds of formula (I) are novel. Therefore a further aspect of the invention provides a compound of formula (Ia)

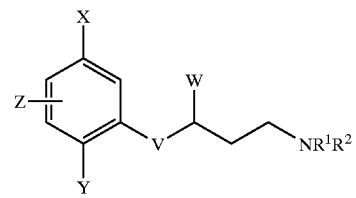

(Ia)

wherein

X and Y independently represent C1 to 4 alkyl, C1 to 4 alkoxy, halogen, $CF_3$, $OCF_3$, CN, C≡CH, $S(O)_m CH_3$, $S(O)_p CF_3$, $NO_2$ or NHCHO;

m and p independently represent an integer 0, 1 or 2;

Z represents H or fluoro;

V represents O;

W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a 4 to 8 membered saturated azacyclic ring optionally incorporating one further heteroatom selected from O, S or $NR^8$; said ring being substituted by OH or by C1 to 4 alkyl substituted by C1 to 4 alkoxy, OH or $NR^9R^{10}$;

or the group $NR^1R^2$ together represents part of a five membered aromatic azacyclic ring optionally incorporating one further N atom;

$R^4$, $R^5$ $R^6$, $R^7$, $R^9$ and $R^{10}$ independently represent H or C1 to 4 alkyl;

$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

$R^{11}$ and $R^{12}$ independently represent H or C1 to 4alkyl;

or a pharmaceutically acceptable salt, enantiomer or racemate thereof, with the proviso that when W represents optionally substituted phenyl, thienyl, furanyl or pyrrolyl and $R^1$ represents H, C1 to 4 alkyl or C3 to 6 cycloalkyl optionally substituted by C1 to 4 alkoxy, then $R^2$ does not represent H, C1 to 4 alkyl or C3 to 6 cycloalkyl optionally substituted by C1 to 4 alkoxy; and with the proviso that when W represents thiazolyl or pyridyl, then either Z represents F; or at least one of X and Y represents CN; or $R^1$ and $R^2$ do not independently represent H or $CH_3$.

In another aspect, the invention concerns compounds of formula (Ia), wherein X, Y, V, W, Z, $R^1$ and $R^2$ are as defined above, with the proviso that when $R^1$ is H, then $R^2$ is not H, C1 to 4 alkyl or benzyl; and with the proviso that when $R^1$ represents C1 to 4 alkyl or C3 to 6 cycloalkyl optionally substituted by C1 to 4 alkoxy, then $R^2$ does not represent C1 to 4 alkyl or C3 to 6 cycloalkyl optionally substituted by C1 to 4 alkoxy.

In one preferred embodiment, X and Y in formula (1a) independently represent Br, Cl, $CH_3$, $CF_3$ or CN. It is particularly preferred that X represents Br, Cl or $CF_3$. It is also particularly preferred that Y represents Cl or CN.

Preferably, W in formula (Ia) represents an optionally substituted five or six membered aromatic heterocyclic ring containing 1 to 3 heteroatoms independently selected from O, S and N. Particular examples are those wherein W represents thienyl, furyl, pyridyl, thiazolyl, oxazolyl, isoxazolyl or pyrimidyl.

Preferably, $R^1$ and $R^2$ in formula (Ia) independently represent H or C1 to 4 alkyl optionally substituted by C1 to 4 alkoxy or hydroxy. More preferably, $R^1$ and $R^2$ independently represent H or methyl.

Particular compounds of formula (Ia) include:

2-[[(3R)-3-(2,5-dichlorophenoxy)-3-(2-thienyl)propyl] amino]ethanol;

4-chloro-2-{[(1R)-3-(4-hydroxy-1-piperidinyl)-1-phenylpropyl]oxy}-benzonitrile;

4-chloro-2-{[(1R)-3-[(2-hydroxyethyl)methylamino]-1-phenylpropyl]oxy}-benzonitrile;

4-chloro-2-{[(1R)-3-[(3R)-3-hydroxypyrrolidinyl]-1-phenylpropyl]oxy}-benzonitrile;

4-chloro-2-{[(1R)-3-[(3S)-3-hydroxypyrrolidinyl]-1-phenylpropyl]oxy}-benzonitrile;

4-chloro-5-fluoro-2-[3-(methylamino)-1-(2-pyrimidinyl) propoxy]benzonitrile;

4-chloro-5-fluoro-2-({(1R)-3-[(3hydroxypropyl)amino]-1-phenylpropyl}oxy)benzonitrile;

4-chloro-5-fluoro-2-[[(1R)-1-(3-furanyl)-3-(3-hydroxypropyl)amino]propyl]oxy}benzonitrile;

4-chloro-5-fluoro-2-{[(1R)-3-[(3-hydroxypropyl)amino]-1-(3-thienyl)propyl]oxy}benzonitrile;

4-bromo-5-fluoro-2-({(1R)-3-[(3-hydroxypropyl)amino]-1-phenylpropyl}oxy)benzonitrile;

4-bromo-5-fluoro-2-({(1R)-1-(3-furanyl)-3-[(3-hydroxypropyl)amino]propyl}oxy)benzonitrile;

4-bromo-5-fluoro-2-{[(1R)-3-[(3-hydroxypropyl)amino]-1-(3-thienyl)propyl]oxy}benzonitrile;

4-chloro-5-fluoro-2-[[(1R)-3-[[(5-methylpyrazinyl) methyl]amino]-1-phenylpropyl]oxy]benzonitrile;

4-chloro-5-fluoro-2-[[(1R)-3-[(1H-imidazol-2-ylmethyl) amino]-1-phenylpropyl]oxy]benzonitrile;

4-chloro-2-[[(1R)-3-[[2-(dimethylamino)ethyl]amino]-1-phenylpropyl]oxy]-5-fluoro benzonitrile;

4-chloro-5-fluoro-2-[[(1R)-3-[[2-(4-morpholinyl)ethyl] amino]-1-phenylpropyl]oxy]benzonitrile;

4-chloro-5-fluoro-2-[[(1R)-3-[[2-(1H-imidazol-1-yl) ethyl]amino]-1-phenylpropyl]oxy]benzonitrile;

4-chloro-5-fluoro-2-[[(1R)-3-[[2-(1H-imidazol-4-yl) ethyl]amino]-1-phenylpropyl]oxy]benzonitrile 4-chloro-5-fluoro-2-[[(1R)-3-[(2-hydroxyethyl)amino]-1-phenylpropyl]oxy]benzonitrile;

2-[[(1R)-3-[(2-aminoethyl)amino]-1-phenylpropyl]oxy]-4-chloro-5-fluorobenzonitrile;

4-chloro-5-fluoro-2-[[(1R)-1-phenyl-3-[(3,3,3-trifluoropropyl)amino]propyl]oxy]benzonitrile;

2-{[(1R)-3-amino-1-(2-thiazolyl)propyl]oxy}-4-chlorobenzonitrile;

4-chloro-2-{[(1R)-3-(methylamino)-1-(2-thiazolyl) propyl]oxy}benzonitrile;

2-[3-amino-1-(2-oxazolyl)propoxy]-4-chlorobenzonitrile;

γ-(2,5-dichlorophenoxy)-2-oxazolepropanamine;

2-[[-3-amino-1-(3-pyridinyl)propyl]oxy]-4-chloro-5-fluorobenzonitrile;

4-chloro-5-fluoro-2-[3-(methylamino)-1-(3-pyridinyl) propoxy]benzonitrile;

2-[3-amino-1-(6-methoxy-2-pyridinyl)propoxy]-4-chloro-5-fluorobenzonitrile;

2-[3-amino-1-(1,6-dihydro-6-oxo-2-pyridinyl)propoxy]-4-chloro-5-fluorobenzonitrile;

2-[3-amino-1-(6-bromo-3-pyridinyl)propoxy]-4-chlorobenzonitrile;

2-[[3-amino-1-(5-isoxazolyl)propyl]oxy]-4-chlorobenzonitrile;

4-chloro-2-[3-[(2-hydroxyethyl)amino]-1-(5-isoxazolyl) propoxy]benzonitrile;

(R)-γ-(2,5-dichlorophenoxy)-5-isoxazolepropanamine;

4-chloro-5-fluoro-2-[[(1R)-3-[(2-hydroxyethyl)amino]-1-(3-thienyl)propyl]oxy]benzonitrile;

2-[[(1R)-3-[(2-aminoethyl)amino]-1-(3-thienyl)propyl] oxy]-4-chloro-5-fluoro-benzonitrile;

4-chloro-2-[3-(methylamino)-1-(2-thiazolyl)propoxy]-benzonitrile;

2-[[(1R)-3-amino-1-(2-thiazolyl)propyl]oxy]-4-chloro-5-fluoro-benzonitrile;

4-chloro-5-fluoro-2-{[(1R)-3-[(2-fluoroethyl)amino]-1-phenylpropyl]oxy}benzonitrile;

3-[[(3R)-3-(2,5-dichlorophenoxy)-3-phenylpropyl] amino]-1-propanol;

1-[(3R)-3-(2,5-dichlorophenoxy)-3-phenylpropyl]-4-piperidinemethanol;

N-[(3R)-3-(2,5-dichlorophenoxy)-3-phenylpropyl]-2-thiophenemethanamine;

N-[(3R)-3-(2,5-dichlorophenoxy)-3-phenylpropyl]-5-methyl-2-furanmethanamine;

5-fluoro-2-[[(1R)-3-[(2-hydroxyethyl)amino]-1-(3-isoxazolyl)propyl]oxy]-4-methyl-benzonitrile;

2-[[(1R)-3-amino-1-(3-isoxazolyl)propyl]oxy]-5-fluoro-4-methyl-benzonitrile;

4-chloro-2-[[(1R)-3-[(1,1-dimethylethyl)amino]-1-(3-isoxazolyl)propyl]oxy]benzonitrile;

2-[[(1R)-3-amino-1-(3-isoxazolyl)propyl]oxy]-4-chloro-benzonitrile;

2-[[(1R)-3-amino-1-(3-isoxazolyl)propyl]oxy]-4-chloro-5-fluoro-benzonitrile;

(R)-γ-(2,5-dichlorophenoxy)-3-isoxazolepropanamine;

2-[[(1R)-3-amino-1-(3-isoxazolyl)propyl]oxy]-4-(trifluoromethyl)-benzonitrile;

2-[[(1R)-3-amino-1-(5-methyl-3-isoxazolyl)propyl]oxy]-4-chloro-5-fluoro-benzonitrile;

and pharmaceutically acceptable salts, enantiomers or racemates thereof.

According to the invention there is also provided a compound of formula (Ia), or a pharmaceutically acceptable salt, enantiomer or racemate thereof, for use as a medicament.

According to the invention, we further provide a process for the preparation of compounds of formula (Ia), or a pharmaceutically acceptable salt, enantiomer or racemate thereof which comprises:

(a) reaction of a compound of formula (II)

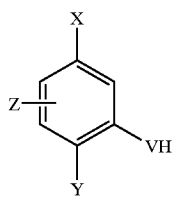
(II)

wherein X, Y, V and Z are as defined in formula (Ia), with a compound of formula (III)

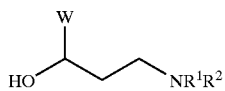
(III)

wherein W, $R^1$ and $R^2$ are as defined in formula (Ia); or (b) reaction of a compound of formula (IV)

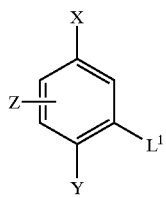
(IV)

wherein X, Y and Z are as defined in formula (Ia) and $L^1$ represents a leaving group, with a compound of formula (V)

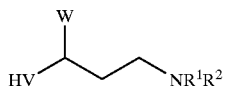
(V)

wherein $R^1$, $R^2$, V and W are as defined in formula (Ia); or (c) reaction of a compound of formula (VI)

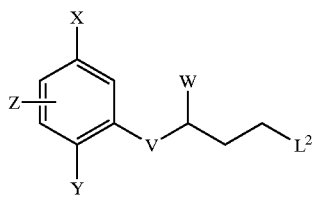
(VI)

wherein X, Y, V, W and Z are as defined in formula (Ia) and $L^2$ is a leaving group, with a compound of formula (VII)

HNR$^1$R$^2$ (VII)

wherein $R^1$ and $R^2$ are as defined in formula (Ia); or (d) reaction of a compound of formula (II)

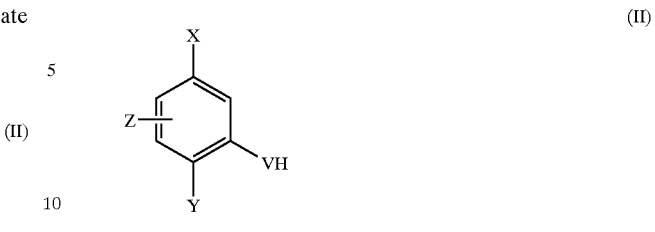
(II)

wherein X, Y, V and Z are as defined in formula (Ia), with a compound of formula (VIII)

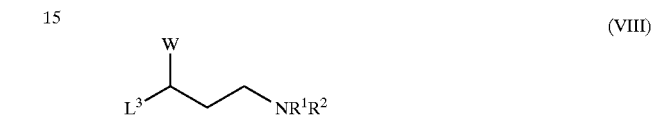
(VIII)

wherein $R^1$, $R^2$ and W are as defined in formula (Ia) and $L^3$ is a leaving group; or (e) reduction of a compound of formula (IX)

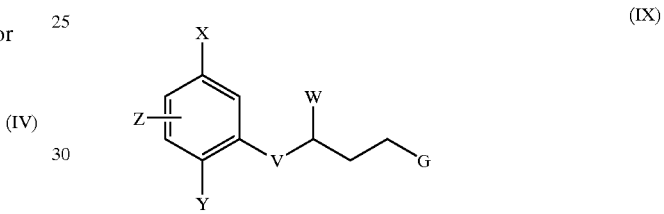
(IX)

wherein X, Y, V, W and Z are as defined in formula (Ia) and G represents a group that upon reduction is converted into a group $NR^1R^2$;

and where necessary converting the resultant compound of formula (Ia), or another salt thereof, into a pharmaceutically acceptable salt thereof; or converting the resultant compound of formula (Ia) into a further compound of formula (Ia); and where desired converting the resultant compound of formula (Ia) into an optical isomer thereof.

In process (a), the reactants (II) and (III) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine.

In process (b), the reaction is performed by treating a nucleophile of formula (V) with an electrophile of formula (IV) in an inert solvent. Suitable leaving groups $L^1$ include halides, particularly fluoride. The reaction is generally performed in the presence of a non-nucleophilic base such as sodium hydride. Suitable organic solvents are those such as N-methyl-2-pyrrolidinone, tetrahydrofuran, C1 to 4 alcohols and dimethylsulfoxide. The reaction is generally conducted at a temperature between 0° C. and the boiling point of the solvent.

Alternatively, in process (b), the reaction will take place using an appropriate palladium source such as palladium (II) acetate in the presence of a suitable phosphine ligand such as BINAP.

In process (c), the amination reaction is performed by reacting a compound of formula (VI) with an amine (VII) in an inert solvent. Suitable leaving groups $L^2$ include sulfonate, trifluorosulfonate, tosylate and halides selected from the group chloride, bromide or iodide. The nucleophile can be a primary or secondary amine in the presence of a base. This base can be either an excess of the amine nucleophile or can be an additive to the reaction mixture. Potential basic additives are metal carbonate, especially alkali metal carbonates, metal oxides and hydroxides, and tertiary amine bases. Suitable organic solvents are those such as acetonitrile, dioxan, N,N-dimethylformamide, N-methyl-2-pyrrolidinone, tetrahydrofuran, dimethylsulfoxide, sulfolane and C1 to 4 alcohols.

In process (d), the reaction is performed by treating a nucleophile of formula (II) with an electrophile of formula (VIII) in an inert solvent. Suitable leaving groups $L^3$ include halides, particularly chloride or bromide. The reaction is generally performed in the presence of a non-nucleophilic base such as sodium hydride. Suitable organic solvents are those such as N-methyl-2-pyrrolidinone, tetrahydrofuran, C1 to 4 alcohols and dimethylsulfoxide. The reaction is generally conducted at a temperature between 0° C. and the boiling point of the solvent.

In process (e), G preferably represents an azido ($N_3$) group. The required reduction may then be achieved by treating a compound of formula (IX) with a suitable reducing agent such as Sn(II) or triphenylphosphine. Preferably the reducing agent is triphenylphosphine and the reduction is carried out in a suitable inert solvent such as tetrahydrofuran.

It will be apparent to a person skilled in the art that in the above processes it may be desirable or necessary to protect an amine, hydroxyl or other potentially reactive group.

Suitable protecting groups and details of processes for adding and removing such groups may be found by reference to the standard text "Protecting Groups in Organic Synthesis", 2nd Edition (1991) by Greene and Wuts. In one preferred embodiment, amine groups are protected as carbamate derivatives, for example, as t-butyloxycarbamates. Thus, compounds of formula (Ia) in which $R^1$ is H are conveniently prepared by removal of a carbamate protecting group from a corresponding compound of formula (Ia) wherein $R^1$ is a carbamate group, especially a t-butyloxycarbamate group. Removal of the carbamate group is conveniently effected using hydrogen chloride in dioxan.

The present invention includes compounds of formula (Ia) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (Ia) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Certain novel intermediates of formulae (III), (V), (VI), (VIII) and (IX) form another aspect of the invention.

Compounds of formula (III) may be prepared by reaction of a compound of formula (IX)

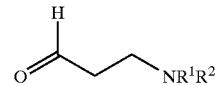

(IX)

wherein $R^1$ and $R^2$ are as defined in formula (Ia),
with an organometallic derivative, W—M, wherein W is as defined in formula (Ia) and M represents a metallic residue such as lithium or magnesium-halide.

Compounds of formula (IX) may be prepared by:
(a) reacting a compound of formula (II), as defined above, with a compound of formula (XI)

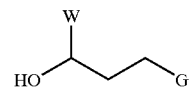

(XI)

wherein W and G are as defined above; or
(b) reacting a compound of formula (IV), as defined above, with a compound of formula (XII)

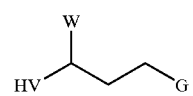

(XII)

wherein V, W and G are as defined above.

Compounds of formulae (II), (IV), (VII), (X), (XI) and (XII) are either known or may be prepared using known methods. Some such methods are illustrated within the Examples that are included herein. Other suitable methods will be readily apparent to the man skilled in the art.

Intermediate compounds may be used as such or in protected form. Protecting groups and details of processes for their removal may be found by reference to the standard text "Protecting groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula (Ia) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (Ia), and their pharmaceutically acceptable salts, enantiomers and racemates, are useful because they possess pharmacological activity in animals. In particular, the compounds of formulae (I) and (Ia) are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. They may also have utility as inhibitors of the neuronal isoform of the enzyme nitric oxide synthase.

The compounds of formulae (I) and (Ia) and their pharmaceutically acceptable salts, enantiomers and racemates are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:

osteoarhritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis, glaucoma and conjunctivitis;

lung disorders in which inflammation is involved, for example, asthma, bronchitis, chronic obstructive pulmonary disease, pigeon fancier's disease, farmer's lung, acute respiratory distress syndrome;

bacteraemia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

By virtue of their pharmacological activity as inhibitors of the enzyme nitric oxide synthase, the compounds will also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease and pain.

The compounds of formulae (I) and (Ia) and their pharmaceutically acceptable salts, enantiomers and racemates may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formulae (I) and (Ia) may also be useful in the treatment of hypoxia, for example in cases of cardiac arrest and stroke, neurodegenerative disorders including nerve degeneration and/or nerve necrosis in disorders such as ischaeria, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, Korsakoff's disease, imbecility relating to a cerebral vessel disorder, sleeping disorders, schizophrenia, autism, seasonal affective disorder, jet-lag and septic shock. Compounds of formulae (I) and (Ia) may also be expected to show activity in the prevention and reversal of drug addiction or tolerance such as tolerance to opiates and diazepines, treatment of migraine and other vascular headaches, neurogenic inflammation, in the treatment of gastrointestinal motility disorders, cancer and in the induction of labour.

We are particularly interested in the conditions stroke, Alzheimer's disease, Parkinson's disease, multiple sclerosis, schizophrenia, migraine, cancer and septic shock.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (Ia), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (Ia), or a pharmaceutically acceptable salt, enantiomer or racemate thereof.

There is also provided a process for the preparation of such a pharmaceutical composition which comprises mixing the ingredients.

The compounds of formulae (I) and (Ia), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

2-(3-Amino-1-phenylpropoxy)-4-chlorobenzonitrile hydrochloride a) (3-Hydroxy-3-phenylpropyl)carbamic acid 1,1-dimethylethyl ester α-(2-Aminoethyl)benzenemethanol (1.21 g, 8 mmol) was dissolved in dry tetrahydrofuran (50 ml) and treated with di-tert-butyl dicarbonate (1.92 g, 8.8 mmol) followed by triethylamine (1.34 ml, 9.6 mmol) and the mixture stirred for 18 h. The reaction mixture was evaporated and the residue eluted down a flash chromatography column using ether/isohexane (1:1) as eluent to give the product (974 mg, 48%) as a viscous yellow oil.

¹H NMR 300 MHz (CDCl₃) 7.35 (4H, m), 7.26 (1H, m), 4.89 (1H, br s), 4.75 (1H, m), 3.49 (1H, br m), 3.17 (2H, m), 1.86 (2H, m), 1.45 (9H, s).

b) 2-(3-Amino-1-phenylpronoxy)-4-chlorobenzonitrile hydrochloride

Triphenylphosphine (67 mg, 2.56 mmol) was dissolved in toluene (50 ml) and the solution cooled to 0° C. Diethyl diazodicarboxylate (45 mg, 2.56 mmol) was added dropwise and the solution stirred for 20 min. 4-Chloro-2-hydroxybenzonitrile (36 mg, 2.34 mmol) in toluene (25 ml) and tetrahydrofuran (10 ml) was added dropwise followed by (3-hydroxy-3-phenylpropyl)carbamic acid 1,1-dimethylethyl ester (59 mg, 2.34 mmol) in toluene (25 ml). The reaction mixture was allowed to warm to room temperature over the weekend, evaporated, and the residue eluted down a flash chromatography column using 10% ether/isohexane as eluent to give the required product protected as the t-butyl carbamate. This material was stirred with 4M hydrogen chloride in dioxan (8 ml) for 2 h, the solvent evaporated, and the residue triturated with dry ether to give the title compound (64 mg, 8.5%) as a colourless solid.

MS APCI+ve $^m/z$ 287 ([M+H]⁺).

¹H NMR 300 MHz (d₆-DMSO) 8.02 (3H, br s), 7.79 (1H, d), 7.44–7.29 (5H, m), 7.22 (1H, d), 7.16 (1H, d of d), 5.88 (1H, m), 2.93 (2H, br m), 2.32 (1H, m), 2.19 (1H, m).

EXAMPLE 2

4-Chloro-2-(3-(methylamino)-1-phenylpropoxy) benzonitrile hydrochloride a) 3-Hydroxy-3-phenylpropyl)methylcarbamic acid 1,1-dimethylethyl ester

[2-(Methylamino)ethyl]benzenemethanol (10.8 g, 65.5 mmol) in methanol (150 ml) was treated with di-tert-butyl dicarbonate (14.7 g, 67.4 mmol) followed by triethylamine (19.0 ml, 136 mmol) and the reaction mixture stirred for 4 h. The solvent was evaporated and the residue eluted down a flash chromatography column using ether/isohexane (1:1) as eluent to give the required product (15.7 g, 90%) as a viscous oil.

GC/MS $^m/z$ 165 (M−100)⁺.

b) 4-Chloro-2-[3-(methylamino)-1-phenylpropoxy] benzonitrile hydrochloride

To triphenylphosphine (0.38 g, 1.46 mmol) in dry tetrahydrofuran (10 ml) under nitrogen was added diisopropyl azodicarboxylate (0.29 ml, 1.46 mmol) dropwise over 2 min. with stirring. The reaction mixture was stirred for 20 min. and then 4-chloro-2-hydroxybenzonitrile (0.22 g, 1.46 mmol) in dry tetrahydrofuran (5 ml) was added, followed 5 minutes later by 3-hydroxy-3-phenylpropyl)methylcarbamic acid 1,1-dimethylethyl ester (0.39 g, 1.46 mmol) in dry tetrahydrofuran (5 ml) and the reaction mixture stirred overnight. The mixture was diluted with ethyl acetate, washed with 10% aqueous sodium carbonate (2×50 ml), then brine and dried over magnesium carbonate. The solvent was evaporated and the residue eluted down a flash chromatography column initially with ether/isohexane (1:1) then re-eluting the cleaner fractions with ether/isohexane (3:7) to give the amide protected product. This was stirred with 4M hydrogen chloride in dioxan (5 ml) for 1 h, evaporated, and the residue triturated with ether to give the title compound (96 mg, 20%) as a colourless solid.

MS APCI+ve $^m/z$ 301 ([M+H]⁺).

¹H NMR 300 MHz (d₆-DMSO) 7.78 (1H, d), 8.93 (2H, br s), 7.44–7.31 (5H, m), 7.27 (1H, d), 7.16 (1H, d of d), 5.91 (1H, m), 2.98 (2H, m), 2.57 (3H, s), 2.41–2.15 (2H, m).

EXAMPLE 3

4-Bromo-2-[(1R)-3-(Methylamino)-1-phenylpropoxy] benzonitrile hydrochloride a) [(3R)-3-Hydroxy-3-phenylpropyl]methylcarbamic acid 1,1-dimethylethyl ester Prepared as for Example 2(a), to give the required product (6.0 g, 78%) as a viscous oil.

MS APCI+ve $^m/z$ 166 ([M−100+H]⁺).

b) [(3R)-3-(5-Bromo-2-cyanophenoxy)-3-phenylpropyl] methylcarbamic acid 1,1-dimethyl ester.

[(3R)-3-Hydroxy-3-phenylpropyl]methylcarbamic acid 1,1-dimethylethyl ester (0.4 g, 1.5 mmol) and 4-bromo-2-fluorobenzonitrile (0.3 g, 1.5 mmol) were dissolved in tetrahydrofuran (10 ml). 60% Sodium hydride (0.08 g, 2.0 mmol) was added and the mixture was stirred for 4 h. The reaction mixture was then quenched with water, extracted with ethyl acetate, dried over magnesium sulphate, filtered and rotary evaporated. Purification by flash chromatography with 20% ethyl acetate/hexane as eluent gave the required product (0.49 g, 73%) as a colourless oil.

MS APCI+ve $^m/z$ 345/7 ([M−100+H]⁺).

c) 4-Bromo 2-[(1R)-3-(methylamino)-1-phenylpropoxy] benzonitrile hydrochloride [(3R)-3-(5-Bromo-2-cyanophenoxy)-3-phenylpropyl]methylcarbamic acid 1,1-dimethyl ester (0.45 g, 1 mmol) was stirred in 4M hydrogen chloride in dioxan (10 ml) for 4 h. The solvent was evaporated and the residue treated with ether to give the required product (0.34 g, 89%) as a white solid.

MS APCI+ve $^m/z$ 345/7 ([M+H]+).

¹H NMR 300 MHz (d₆-DMSO) 9.03 (2H, s), 7.71 (1H, d), 7.41–7.45 (5H, m) 7.36 (1H, m), 7.27 (1H, d), 5.94 (1H, m), 2.94–3.04 (2H, m), 2.56 (3H, s), 2.31–2.40 (1H, m), 2.19–2.26 (1H, m).

EXAMPLE 4

γ-R-(2-Bromo-5-chlorophenoxy)-N-methylbenzenepropanamine hydrochloride

α-[2-(Methylamino)ethyl]-(α1R)-benzenemethanol (0.395 g, 2.39 mmol) was dissolved in dimethylsulphoxide (3 ml) and 60% sodium hydride (0.19 g, 4.78 mmol) added. The mixture was heated at 40° C. for 30 min, 1-bromo-4-chloro-2-fluorobenzene (0.5 g, 2.39 mmol) was added and the mixture was stirred at 50° C. for 20 h. The mixture was cooled to room temperature, quenched with water, extracted with ethyl acetate, dried over magnesium sulphate, filtered and evaporated. The residue was purified by flash chromatography with 5% 7M ammonia-methanol in dichloromethane as eluent to give the required product (0.47 g, 50%) as a white solid.

MS APCI+ve $^m/z$ 354/5/6/7/8 ([M+H]⁺).

¹H NMR 300 MHz (d₆-DMSO) 9.05 (2H, s), 7.59 (1H, d), 7.39–7.42 (5H, m), 7.31–7.34 (1H, m), 6.92 (1H, d), 5.82 (1H, m), 2.95–3.00 (2H, m), 2.56 (3H, s), 2.28–2.37 (1H, m), 2.19–2.25 (1H, m).

EXAMPLE 5

4-Chloro-2-{[(1R)-3-chloro-1-phenylpropyl] oxy}benzonitrile hydrochloride a) 4-Chloro-2-{[(1R)-3-chloro-1-phenylpropyl] oxy}benzonitrile (S)-α-(2-Chloroethyl)benzenemethanol (170 mg, 1.0 mmol), 4-chloro-2-hydroxybenzonitrile (154 mg, 1.0 mmol.) and triphenylphosphine (260 mg, 1.0 mmol.) in dry tetrahydrofuran (5 ml) were stirred in an ice bath under nitrogen whilst diethyl azodicarboxylate (0.16 ml, 1.0 mmol.) was added. The reaction mixture was allowed to warm to room temperature and stirred for 3 days. The solvent was evaporated and the residue dissolved in toluene, added to the top of a flash chromatography column and eluted with 10% ether/isohexane to give the product (220 mg, 72%) as a viscous oil.

¹H NMR 300 MHz (CDCl₃) 7.21 (1H, d), 7.24–7.33 (5H, m), 6.92 (1H, d of d), 6.75 (1H, d), 5.43 (1H, m), 3.80 (1H, m), 3.56 (1H, m), 2.50 (1H, m), 2.18 (1H, m).

b) 4-Chloro-2-{[(1R)-3-iodo-1-phenylpropyl]oxy}benzonitrile

4-Chloro-2-{[(1R)-3-chloro-1-phenylpropyl]oxy}benzonitrile (220mg, 0.718 mmol) was dissolved in acetone (20 ml) which had previously been saturated with sodium iodide and the solution was heated under reflux for 18 h. The reaction mixture was cooled, filtered, evaporated and the residue partitioned between water and ethyl acetate. The organic layer was separated, washed twice with water and dried (magnesium sulphate). The solvent was evaporated to leave 0.24 g (84%) of the product as a yellow oil. This was used without purification for the next step.

c) 4-Chloro-2-{[1R)-3-(methylamino)-1-phenylpropyl]oxy}benzonitrile hydrochloride 4-Chloro-2-{[(1R)-3-iodo-1-phenylpropyl]oxy}benzonitrile (240 mg, 0.604 mmol.) was dissolved in tetrahydrofuran (10 ml), treated with 40% aqueous methylamine (5 ml) and stirred for 5 h at room temperature. The solvents were removed in vacuo and the residue dissolved in water and extracted into ethyl acetate which was dried (magnesium sulphate). The solvent was evaporated and the residue stirred with 4M hydrogen chloride in dioxan (5 ml) for 1 h. The solvent was evaporated and the residue azeotroped twice with ether and finally triturated with ether to give the required product (155 mg, 76%) as a fawn coloured solid.

MS APCI+ve $^m/z$ 301 ([M+H]⁺).

¹H NMR 300 MHz (d₆-DMSO) 8.86 (2H, br s), 7.79 (1H, d), 7.44–7.31 (5H, m), 7.26 (1H, d), 7.16 (1H, d of d), 5.90 (1H, m), 3.01 (2H, br m), 2.57 (3H, t,) 2.41–2.15 (2H, m).

EXAMPLE 6

4-Methoxy-2-[3-(methylamino)-1-phenylamino-1-phenylpropoxy]benzonitrile hydrochloride The title compound was prepared by the method of Example 2(b) using 2-hydroxy-4-methoxy-benzonitrile to give 0.13 g (27%) of the product as a glassy solid.

MS APCI+ve $^m/z$ 297 ([M+H]⁺).

¹H NMR 300 MHz (d₆-DMSO) 8.92 (2H, br s), 7.64 (1H, d), 7.46–7.30 (5H, m), 6.66 (1H, d), 6.63 (1H, d of d), 5.85 (1H, m), 3.73 (3H, s), 300 (2H, br m), 2.57 (3H, s), 2.37–2.18 (2H, m).

EXAMPLE 7

4-Methyl-2-{[(1R)-3-(methylamino)-1-phenylpropyl]oxy}benzonitrile hydrochloride

The title compound was prepared by the method of Example 1(b) using initially [(3R)-3-hydroxy-3-phenylpropyl]methylcarbamic acid 1,1-dimethylethyl ester and 2-hydroxy-4-methylbenzonitrile to give 0.35 g (73%) of the product as a colourless solid.

MS APCI+ve $^m/z$ 281 ([M+H]⁺).

¹H NMR 300 MHz (d₆-DMSO) 9.09 (2H, br), 7.58 (1H, d), 7.39–7.46 (4H, m), 7.32 (1H, m), 7.02 (1H, s), 6.87 (1H, d), 5.84 (1H, m), 3.00 (2H, m) 255 (3H, s), 2.30–2.39 (1H, m), 2.19–2.25 (1H, m), 2.25 (3H, s).

EXAMPLE 8

R-γ-(2,5-Dichlorophenoxy)-N-methyl-2-thiophenepropanamine a) 2-[(1R)-3-Chloro-1-(2,5-dichlorophenoxy)propyl]thiophene A solution of diethyl azodicarboxlate (0.7 ml) was added to a solution of S-α-(2-chloroethyl)-2-thiophenemethanol (657 mg), 2,5-dichlorophenol (607 mg) and triphenylphosphine (1.17 g) in toluene (10 ml) at 0° C. and the mixture was stirred at 0° C. for 3 h and at 20° C. for 14 h. The solvent was removed in vacuo and the residue purified by chromatography on silica eluting with petrol—diethyl ether (9:1) to give the title compound as a colourless oil (788 mg).

¹H NMR (CDCl₃) 7.32–6.84 (6H, m), 5.72–5.65 (1H, m), 3.87–3.81 (1H, m), 3.68–3.60 (1H, m), 2.69–2.58 (1H, m), 2.41–2.32 (2H, m).

b) 2-[(1R)-1-(2,5-Dichlorophenoxy)-3-iodopropyl]thiophene

A solution of the product from step (a) (788 mg) and sodium iodide (4.5 g) in acetone (30 ml) was heated under reflux for 18 h. The solvent was removed in vacuo, water added and the mixture was extracted twice with ether. The organic layers were dried (magnesium sulphate), evaporated and purified by chromatography on silica eluting with petrol—diethyl ether (19:1) to give the title compound as a pale yellow oil (742 mg).

¹H NMR (CDCl₃) 7.30–7.23 (2H, m), 7.09 (1H, d), 6.99–6.86 (3H, m), 5.59–5.53 (1H, m), 3.47–3.39 (1H, m), 3.29–3.21 (1H, m), 2.72–2.60 (1H, m), 2.47–2.36 (1H, m).

c) R-γ-(2,5-Dichlorophenoxy)-N-methyl-2-thiophenepropanamine fumarate

A solution of the product from step (b) (217 mg) in 40% aqueous methylamine (5 ml) and tetrahydrofuran (5 ml) was stirred for 2.5 days. The solvent was removed in vacuo, water added and the mixture was extracted three times with ethyl acetate. The organic layers were dried (sodium sulphate), evaporated and purified by chromatography on silica eluting with dichloromethane—7M ammonia in methanol (19:1) to give an oil (116 mg). To a solution of this oil in ethyl acetate was added a solution of fumaric acid (43 mg) in methanol. The precipitate was collected and dried to give the title compound as a fine white solid (127 mg).

MS (APCI) $^m/z$ 316 [(M+H)⁺].

¹H NMR 300 MHz (d₆-DMSO) 7.53 (1H, d), 7.44 (1H, d), 7.30 (1H, s), 7.21 (1H, d), 7.04–6.95 (2H, m), 6.43 (2H, s), 6.05 (1H, dd), 2.97–2.85 (2H, m), 2.49 (3H, s), 2.44–2.16 (2H, m).

EXAMPLE 9

S-γ-(2,5-Dichlorophenoxy)-N-methyl-2-thiophenepropanamine a) 2-[(1S)-3-Chloro-1-(2,5-dichlorophenoxy)propyl]thiophene The title compound was prepared according to the method of Example 8(a) using R-α-(2-chloroethyl)-2-thiophenemethanol.

¹H NMR 300 MHz (CDCl₃) 7.32–6.84 (6H, m), 5.72–5.65 (1H, m), 3.87–3.81 (1H, m), 3.68–3.60 (1H, m), 2.69–2.58 (1H, m), 2.41–2.32 (1H, m).

b) 2-[(1S)-1-(2,5-Dichlorophenoxy)-3-iodopropyl]thiophene

The title compound was prepared according to the method of Example 8(b) using the product from step (a).

¹H NMR 300 MHz (CDCl₃) 7.30–7.23 (2H, m), 7.09 (1H, d), 6.99–6.86 (3H, m), 5.59–5.53 (1H, m), 3.47–3.39 (1H, m), 3.29–3.21 (1H, m), 2.72–2.60 (1H, m), 2.47–2.36 (1H, m).

c) S-γ-(2.5-Dichlorophenoxy)-N-methyl-2-thiophenepropanamine fumarate

The title compound was prepared according to the method of Example 8(c) using the product from step (b).

MS (APCI) $^m$/z 316 [(M+H)$^+$].

$^1$H NMR 300 MHz (d$_6$-DMSO) 7.53 (1H, d), 7.44 (1H, d), 7.30 (1H, s), 7.21 (1H, d), 7.04–6.95 (2H, m), 6.43 (2H, s), 6.04–6.60 (1H, m), 2.95–2.84 (2H, m), 2.48 (3H, s), 2.43–2.29 (1H, m), 223–2.13 (1H, m).

EXAMPLE 10

2-[[(3R)-3-(2,5-Dichlorophenoxy)-3-(2-thienyl)propyl]amino]ethanol fumarate

A solution of the product from Example 8(b) (214 mg) and ethanolamine (0.1 ml) in tetrahydrofuran (5 ml) was stirred for 2.5 days. The solvent was removed in vacuo, water added and the mixture was extracted three times with ethyl acetate. The organic layers were dried (sodium sulphate), evaporated and purified by chromatography on silica eluting with dichloromethane—7M ammonia in methanol (19:1) to give an oil (116 mg). To a solution of this material in ethyl acetate was added a solution of fumaric acid (43 mg) in methanol. The precipitate was collected and dried to give the title compound as a fine white solid (127 mg).

MS (APCI) $^m$/z 346 [(M+H)$^+$].

$^1$H NMR 300 MHz (d$_6$-DMSO) 7.51 (1H, d), 7.43 (1H, d), 7.32 (1H, s), 7.20 (1H, d), 7.01–6.98 (2H, m), 6.43 (2H, s), 6.01 (1H, t), 3.53 (2H, t), 2.84–2.74 (4H, m), 2.38–2.28 (1H, m), 2.18–2.1 (1H, m).

EXAMPLE 11

4-Chloro-2-{[(1R)-3-(4-methyl-1-piperazinyl)-1-phenylpropyl]oxy}-benzonitrile dihydrochloride 4-Chloro-2-{[(1R)-3-chloro-1 phenylpropyl]oxy}-benzonitrile (0.17 g), 4-methylpiperazine (0.2 g), potassium iodide (0.02 g) in N-methylpyrrolidone (5 ml) were heated at 100° C. for 3 h. The reaction mixture was allowed to cool to ambient temperature and poured into water and the product extracted into ethyl acetate. The ethyl acetate solution was washed with water, brine, dried over magnesium sulphate and evaporated to dryness to afford an oil. The oil was triturated with 1 M hydrogen chloride in ether to afford the product as the dihydrochloride salt (0.135 g).

MS APCI+ve$^m$/z 370 [(M+H)$^+$].

$^1$H NMR (d$_6$-DMSO) 7.78 (1H, dd), 7.33–7.48 (5H, m), 7.29 (1H, s), 7.16 (1H, dd), 5.89 (1H, m), 3.2–4.8 (10H, m), 2.82 (3H, s), 2.45–2.50 (2H, m).

EXAMPLE 12

4-Chloro-2-{[(1R)-3-(4-hydroxy-1-piperidinyl)-1-phenylpropyl]oxy}-benzonitrile fumarate 4-Chloro-2-{[(1R)-3-chloro-1-phenylpropyl]oxy}-benzonitrile and 4-hydroxy-piperidine were reacted as described in Example 11 to afford the title compound. This was converted into the fumarate salt by trituration with one equivalent of fumaric acid in methanol.

MS APCI+ve$^m$/z 371 [(M+H)$^+$].

$^1$H NMR (d$_6$-DMSO) 7.51 (1H, d), 7.26–7.38 (5H, m), 6.97 (1H, d), 6.9 (1H, s), 6.70 (2H, s), 5.50 (1H, m), 3.65–3.75 (1H, m), 2.85–2.95 (2H, m), 2.6–2.82 (2H, m), 2.35–2.50 (2H, m), 2.2–2.3 (1H, m), 2.05–2.01 (1H, m), 1.86–2.0 (2H, m), 1.6–1.7 (2H, m).

EXAMPLE 13

4-Chloro-2-{[(1R)-3-[(2-hydroxyethyl)methylamino]-1-phenylpropyl]oxy}-benzonitrile hydrochloride 4-Chloro-2-{[(1R)-3-chloro-1-phenylpropyl]oxy}-benzonitrile and (2-methylamino)-ethanol were reacted as described in Example 11 to afford the title compound.

MS APCI+ve$^m$/z 345 [(M+H)$^+$].

$^1$H NMR (CDCl$_3$) 7.48 (1H, d), 7.31–7.45 (5H, m), 7.00 (1H, dd), 6.88 (1H, d), 5.66 (1H, dd), 5.01 (1H, bs), 4.00 (2H, m), 3.27 (1H, bs), 2.92 (3H, s), 2.53–2.60 (6H, m).

EXAMPLE 14

4-Chloro-2-{[(1R)-3-(4-morpholinyl)-1-phenylpropyl]oxy}-benzonitrile fumarate

4-Chloro-2-{[(1R)-3-chloro-1-phenylpropyl]oxy}-benzonitrile and morpholine were reacted as described in Example 11 to afford the title compound. This was converted into the fumarate salt by trituration with one equivalent of fumaric acid in methanol.

MS APCI+ve$^m$/z 357 [(M+H)$^+$].

$^1$H NMR (d$_6$-DMSO) 7.49 (1H, dd), 7.29–7.38 (5H, m), 7.29 (1H, dd), 6.92 (1H, d), 6.76 (2H, s), 5.42 (1H, m), 3.71 (4H, m), 2.5–2.7 (2H, m), 2.43–2.49 (4H, m), 2.24–2.31 (1H, m), 2.02–2.22 (1H, m).

EXAMPLE 15

4-Chloro-2-{[(1R)-3-[(3R)-3-hydroxypyrrolidinyl]-1-phenylpropyl]oxy}-benzonitrile fumarate 4-Chloro-2-{[(1R)-3-chloro-1-phenylpropyl]oxy}-benzonitrile and (3R)-3-hydroxypyrrolidine were reacted as described in Example 11 to afford the title compound. This was converted into the fumarate salt by trituration with one equivalent of fumaric acid in methanol.

MS APCI+ve$^m$/z 357/359 [(M+H)$^+$].

$^1$H NMR (d$_6$-DMSO) 7.76 (1H, d), 7.25–7.45 (5H, m), 7.20 (1H, s), 7.10 (1H, dd), 6.55 (2H, s) 5.75 (1H, m), 4.24 (1H, m), 2.95 (1H, m), 2.91 (1H, m), 2.82 (2H, m), 2.51 (2H, m) 2.18–2.3 (1H, m), 1.97–2.05 (2H, m), 1.62–1.64 (1H, m).

EXAMPLE 16

4-Chloro-2-{[(1R)-3-[(3S)-3-hydroxypyrrolidinyl]-1-phenylpropyl]oxy}-benzonitrile fumarate 4-Chloro-2-{[(1R)-3-chloro-1-phenylpropyl]oxy}-benzonitrile and (3S)-3-hydroxypyrrolidine were reacted as described in Example 11 to afford the title compound. This was converted into the fumarate salt by trituration with one equivalent of fumaric acid in methanol.

MS APCI+ve$^m$/z 357/359 [(M+H)$^+$].

$^1$H NMR (d$_6$-DMSO) 7.76 (1H, d), 7.25–7.45 (5H, m), 7.20 (1H, s), 7.10 (1H, dd), 6.55 (2H, s) 5.75 (1H, m), 4.24 (1H, m), 2.95 (1H, m), 2.91 (1H, m), 2.82 (2H, m), 2.51 (2H, m), 2.18–2.3 (1H, m), 1.97–2.05 (2H, m), 1.62–1.64 (1H, m).

EXAMPLE 17

2-{[(1R)-3-Amino-1-phenylpropyl]oxy}-5-fluoro-4-methylbenzonitrile Fumarate a) 5-Fluoro-2-hydroxy-4-methylbenzonitrile To a IM solution of boron trichloride in dichloromethane (48 ml, 48 mmol) was added, in sequence, a solution of 4-fluoro-3-methylphenol (4.44 ml, 40 mmol) in dichloromethane (40 ml), methyl thiocyanate (3.3 ml, 48 mmol) and anhydrous aluminium chloride (5.4 g, 40 mmol) at 0° C. with stirring. The reaction mixture was heated under reflux for 3 h, and stirred at room temperature overnight. The solvent was evaporated, replaced by dichloroethane and added to ice and 4N sodium hydroxide (132 ml). The mixture was heated at reflux for 0.5 h with stirring, cooled to room temperature, the organic layer separated, and the aqueous layer further washed with dichloroethane. The aqueous layer was acidified with 2M hydrochloric acid and the solid that had precipitated collected by filtration, and washed well with water. The solid was dissolved in ethyl acetate, dried over magnesium sulphate, evaporated and the residue triturated with isohexane with ice cooling to give 3.5 g (58%) of the sub title compound as a colourless solid.

$^1$H NMR 300 MHz (d$_6$-DMSO) 7.12 (1H, d), 6.81 (1H, d), 2.29(3H, s).

b) 2-[[(1R)-3-Chloro-1-phenylpropyl]oxy]-5-fluoro-4-methylbenzonitrile

The subtitle compound was prepared by the method of Example 5(a) using 5-fluoro-2-hydroxy-4-methylbenzonitrile and S-α-(2-chloroethyl)benzenemethanol.

$^1$H NMR 300 MHz (CDCl$_3$) 7.41–7.29 (5H, m), 7.16 (1H, d), 6.63 (1H, d), 5.45 (1H, m), 3.89 (1H, m), 3.63 (1H, m), 2.55 (1H, ), 2.24 (1H, m), 2.17 (3H, s).

c) 5-Fluoro-2-[[(1R)-3-iodo-1-phenylpropyl]oxy]-4-methylbenzonitrile

The subtitle compound was prepared by the method of Example 5(b) using 5-fluoro-2-[[(1R)-3-chloro-1-phenylpropyl]oxy]-5-fluoro-4-methylbenzonitrile.

$^1$H NMR 300 MHz (CDCl$_3$) 7.39–7.31 (5H, m), 7.16 (1 H, d), 6.64 (1H, d), 5.33 (1H, m), 3.47 (1H, m), 3.28 (1H, m), 2.54 (1H, m), 2.31 (1H, m), 2.18 (3H, s).

d) 2-[[(1R)-3-azido-1-phenylpropyl]oxy]-5-fluoro-4-methylbenzonitrile

The iodo compound 17 (c) (504 mg, 1.28 mmol) and sodium azide (124 mg, 1.91 mmol) in dimethylsulphoxide (5 ml) and water (2 drops) were stirred for 3 h. The reaction mixture was poured into water, and extracted with ethyl acetate which was then washed with brine and dried over anhydrous magnesium sulphate. The solvent was evaporated to give 361 mg (91%) of a pale yellow oil.

$^1$H NMR 300 MHz (CDCl$_3$) 7.39–7.29 (5H, m), 7.16 (1H, d), 6.59 (1H, d), 5.30 (1H, m), 3.67 (1H, m), 3.46 (1H, m), 2.31 (1H, m), 2.17 (3H, t), 2.08 (1H, m).

e) 2-{[(1R)-3-Amino-1-phenylpropyl]oxy}-5-fluoro-4-methylbenzonitrile Fumarate

The azide 17(d) in tetrahydrofuran (15 ml) was treated with triphenylphosphine (512 mg, 1.95 mmol) followed by water (1.5 ml). The reaction mixture was heated under reflux with stirring for 2 h, evaporated and the residue eluted down a flash chromatography column, initially using ethyl acetate and then 5% 7M ammonia in methanol/dichloromethane as eluent to give 186 mg of a viscous oil. This was dissolved in the minimum of ethanol, treated with fumaric acid (75.7 mg, 0.652 mmol), warmed to complete solution and treated with ether until turbid. After standing for 1 h the crystals were collected by filtration, washed with a little acetonitrile and dried at 40° C. in vacuo to give 159 mg (30%) of the title compound as a colourless solid.

MS APCI+ve$^m$/z285 C(M+H)$^+$].

$^1$H NMR 300 MHz (d$_6$-DMSO) 7.63 (1H, d), 7.43–7.28 (5H, m), 7.08 (1H, d), 6.39 (2H, s), 5.73 (1H, m), 2.87 (2H, t), 2.30–2.03 (2H, m), 2.17 (3H, s).

EXAMPLE 18

4-Chloro-5-fluoro-2-[3-(methylamino)-1-(2-pyrimidinyl)propoxy]benzonitrile hydrochloride a) [3-Hydroxy-3-(2-pyrimidinyl)propyl]methylcarbamic acid, 1,1-dimethylethyl ester To 2-(tributylstannyl)pyrimidine (690 mg, 1.87 mmol) dissolved in dry tetrahydrofuran (10 ml) cooled to −78° C. was added 2.4M n-butyl lithium in hexanes (0.8 ml, 1.87 mmol) under nitrogen. After stirring for a further 0.5 h, methyl(3-oxopropyl)carbamic acid, 1,1-dimethylethyl ester in dry tetrahydrofuran (10 ml) was added rapidly at −78° C. The reaction mixture was allowed to warm to ambient, treated with aqueous saturated ammonium chloride solution and extracted with ethyl acetate which was washed with brine and dried over anhydrous magnesium sulphate. The solvent was evaporated and the residue eluted down a flash chromatography column using initially 10% ethyl acetate/dichloromethane, then 10% methanol/dichloromethane to give 260 mg (43%) of the subtitle compound as a viscous yellow oil.

MS APCI+ve$^m$/z 268 [(M+H)$^+$].

b) [3-(5-Chloro-2-cyano-4-fluorophenoxy)-3-(2-pyrimidinyl)propyl]methylcarbamic acid, 1,1-dimethylethyl ester The alcohol 18 (a) (255 mg, 0.955 mmol) in dry N,N-dimethylformamide (15 ml) was treated with sodium hydride (60% in mineral oil, 40 mg, 0.955 mmol) and the reaction mixture stirred under nitrogen until effervescence had ceased. 4-Chloro-2,5-difluorobenzonitrile (166 mg, 0.955 mmol) was added and the reaction mixture heated at 40° C. under nitrogen for 1 h. The reaction was cooled, partitioned between brine and ethyl acetate, the organic layer separated, washed with water (5x), then brine and dried over anhydrous magnesium sulphate. The solvent was evaporated and the residue eluted down a flash chromatography column using 30% ethyl acetate/isohexane as eluent to give 140 mg (35%) of the subtitle compound as a viscous oil.

$^1$H NMR 300 MHz (CDCl$_3$) 8.76 (2H, d), 7.33 (1H, d), 7.26 (1H, m), 6.92 (1H, br m), 5.33 (1H, br m), 3.65 (1H, br m), 3.41 (1H, m), 2.89 (3H, s), 2.45–2.30 (2H m), 1.38 (9H, s).

c) 4-Chloro-5-fluoro-2-[3-(methylamino)-1-(2-pyrimidinyl)propoxy]benzonitrile hydrochloride The carbamate 18 (b) (140 mg, 0.333 mmol) was treated with 4M HCl in dioxan (10 ml) and stirred for 1 h. The solid which had precipitated was collected by. filtration washed with ether and dried to give 97 mg (80%) of the required product as a colourless solid.

MS APCI+ve$^m$/z 321 [(M+H)$^+$].

$^1$H NMR 300 MHz (d$_6$-DMSO) 8.98 (2H, br m), 8.88 (2H, d), 8.04 (1H, d), 7.52 (1H, t), 7.41 (1H, d), 5.90 (1H, t), 3.12 (2H, m), 2.58 (2H, t), 2.49 (3H, s).

EXAMPLE 19

4-Chloro-5-fluoro-2-({(1R)-1-(3-furanyl)-3-[(2-methoxyethyl)amino]propyl}oxy)benzonitrile oxalate a) (R)-α-(2-Chloroethyl)-3-furanmethanol This was prepared in a two step sequence as for the preparation of Example 74(d) starting from 1-(3-furanyl)-2-propen-1-one, to give a colourless oil.

$^1$H NMR 300 MHz (CDCl$_3$) 7.43–7.41 (2H, m), 6.42 (1H, s), 4.98–4.92 (1H, m), 3.79–3.73 (2H, m), 2.30–2.10 (2H, m).

b) 4-Chloro-5-fluoro-2-({(1R)-1-(3-furanyl)-3-[(2-methoxyethyl)amino]propyl}oxy)benzonitrile oxalate (R)-α-(2-Chloroethyl)-3-furanmethanol (100 mg, 0.62 mmol) was dissolved in tetrahydrofuran (5 ml) at room temperature. To this solution was added sodium hydride as a 60% suspension in mineral oil (37 mg, 0.93 mmol) and the mixture was stirred for 10 minutes before solid 4-chloro-2,5-difluorobenzonitrile (107.6 mg, 0.62 mmol) was added in one portion. The resultant mixture was stirred for 1 h before water (2 ml) was added and the mixture concentrated in vacuo. The residues were partitioned between dichloromethane and water. The organics were collected, dried over magnesium sulphate, filtered and concentrated to dryness in vacuo. The resultant residue was dissolved in N,N-dimethylformamide (2 ml) and treated with sodium iodide (93 mg, 0.62 mmol), triethylamine (172 μl, 1.24 mmol) and 2-methoxyethanamine (107 μl, 1.24 mmol) before being heated to 60° C. for 72 h. After being allowed to cool the mixture was filtered and purified via reverse phase HPLC to give the title compound as a free base which was treated with a 50% saturated solution of oxalic acid in ether. The resultant white solid was collected via filtration to yield the title compound (61 mg, 28%).

MS APCI+ve$^m$/z 353/355 [(M+H)$^+$].

$^1$H NMR 300 MHz (d$_6$-DMSO) 8.02 (1H, d), 7.82 (1H, s), 7.70 (1H, s), 7.59 (1H, s), 5.72 (2H, t), 3.57 (2H, m), 3.31 (3H, s), 3.16 (2H, m), 3.09–2.98 (2H, b), 2.37 (1H, bm), 2.27 (1H br m).

EXAMPLE 20

4-Methoxy-2-[[(1R)-3-(methylamino)-1-phenylpropyl]oxy]-benzonitrile hydrochloride (a) [(3R)-3-(2-Cyano-5-methoxyphenoxy)-3-phenylpropyl]methylcarbamic acid, 1,1-dimethylethyl ester To a stirred mixture of 2-cyano-5-methoxyphenol (149 mg, 1.00 mmol) and [(3S)-3-hydroxy-3-phenylpropyl]methylcarbamic acid 1,1-dimethylethyl ester (265 mg, 1.00 mmol) in tetrahydrofuran (10 ml) under nitrogen was added triphenylphosphine (290 mg, 1.10 mmol) followed by diethyl diazodicarboxylate (192 mg, 1.10 mmol). The reaction mixture was stirred at room temperature for 24 h, then evaporated to dryness. The residue was eluted down a flash chromatography column using 30% ethyl acetate/isohexane as eluent to give 275 mg (69%) of the subtitle compound as an oil.

$^1$H NMR 300 MHz (CDCl$_3$) 7.26–7.45 (6H, m), 6.43 (1H, dd), 6.25 (1H, s), 5.19 (1H, bs), 3.67 (3H, s), 3.50 (2H, bs), 2.87 (3H, s), 2.25 (1H, bs), 2.10 (1H, m), 1.38 (9H, s).

b) 4-Methoxy-2-[[(1R)-3-(methylamino)-1-phenylpropyl]oxy]-benzonitrile fumarate

[(3R)-3-(2-Cyano-5-methoxyphenoxy)-3-phenylpropyl]methylcarbamic acid, 1,1-dimethylethyl ester (270 mg, 0.682 mmol) was dissolved in 4M hydrogen chloride in dioxane (8 ml). The resulting solution was stirred at room temperature for 20 h, then diluted with sodium bicarbonate solution containing ammonia and extracted three times with dichloromethane. The combined organic fractions were washed with brine then dried over magnesium sulphate. The solvent was evaporated and the residue dissolved in ethanol.

To this solution was added fumaric acid in ethanol and the solvent evaporated. The residue was recrystallised from ethanol/diethyl ether to give 128 mg (46%) of the title compound as a white solid.

MS APCI+ve$^m$/z 297 [(M+H)$^+$].

$^1$H NMR 300 MHz (d$_6$-DMSO) 7.62 (1H, d), 7.29–7.44 (5H, m), 6.61 (2H, m), 6.44 (2H, s), 5.74 (1H, dd), 3.71 (3H, s), 2.89 (2H, t), 2.50 (3H, s), 2.22 (1H, m), 2.11 (1H, m).

EXAMPLE 21

γ-(2-Bromo-5-fluorophenoxy)-N-methyl-benzenepropanamine fumarate

Prepared by the method of Example 2 (b) using (3-hydroxy-3-phenylpropyl)methylcarbamic acid 1,1-dimethylethyl ester and 2-bromo-5-fluorophenol and converted into the title compound as a fumarate salt (white solid) (11.3 mg, 3.2%).

MS APCI+ve$^m$/z 338 [(M+H)$^+$].

$^1$H NMR 300 MHz (d$_6$-DMSO) 7.61–7.56 (1H, dd), 7.40–7.30 (5H, m), 6.90–6.86 (1H, dd), 6.75–6.69 (1H, dt), 6.43 (2H, s), 5.69–5.65 (1H, m), 3.35 (3H, s), 2.90–2.845 (2H, t), 2.27–2.06 (2H, m).

EXAMPLE 22

(R)-γ-(5-Bromo-2-chlorophenoxy)-N-methylbenzenepropanamine fumarate

[(3S)-3-Hydroxy-3-phenylpropyl]methylcarbamic acid 1,1-dimethylethyl ester was reacted with 5-bromo-2-chlorophenol, in a similar method to that described in Example 2 (b) to give the title compound as a fumarate salt (white solid) (449 mg, 52%).

$^1$H NMR 400 MHz (d$_6$-DMSO) 7.40–7.36 (5H, m), 7.34–7.29 (1H, m), 7.19–7.19 (1H, d). 7.10–7.08 (1H, dd), 6.44 (2H, s), 5.72–5.70 (1H, m), 2.90–2.86 (2H, t), 2.52–2.48 (3H, s), 2.29–2.05 (2H, m).

EXAMPLE 23

(R)-γ-(2-Bromo-5-nitrophenoxy)-N-methylbenzenepropanamine fumarate

[(3S)-3-Hydroxy-3-phenylpropyl]methylcarbamic acid 1,1-dimethylethyl ester was reacted with 2-bromo-5-nitrophenol in a similar method to that described in Example 2(b) to give the title compound as a fumarate salt (yellow solid) (278 mg, 49.8%).

MS APCI+ve$^m$/z 365 [(M+H)$^+$].

$^1$H NMR 300 MHz (d$_6$-DMSO) 7.91–7.88 (1h, d), 7.72–7.67 (2H, m), 7.46–7.28 (5H, m), 6.43 (2H, s), 5.88–5.84 (1H, dd), 2.93–2.89 (2H, t), 2.53–2.43 (3H, s), 2.38–2.10 (2H, m).

EXAMPLE 24

4-Chloro-5-fluoro-2-[[(1R)-3[(2-methoxyethyl)amino]-1-phenylpropyl]oxy]-benzonitrile oxalate 4-Chloro-5-fluoro-2-[[(1R)-3-iodo-1-phenylpropyl]oxy]-benzonitrile (0.481 mmol, made by method of Example 43 (b)) was dissolved in 2-methoxyethylamine (2.4 mmol) and the resulting yellow solution stirred at room temperature for 24 h. Excess amine was evaporated and the residue partitioned between aqueous sodium hydrogen carbonate and ethyl acetate. The crude product was extracted into ethyl acetate which was then dried over anhydrous sodium sulphate. Filtration followed by evaporation gave an oil which was purified by the use of chromotography and reverse phase HPLC. The residue was converted into an oxalate salt using oxalic acid and methanol to give 48 mg (22%) of the title compound.

MS APCI+ve$^m$/z 363 [(M+H)$^+$].

$^1$H NMR 400 MHz (d$_6$-DMSO) 8.03–8.01 (1H, d), 7.45–7.41 (5H, m), 7.37–7.32 (1H, m), 5.79–5.76 (1H, m), 3.55–3.52 (2H, t), 3.29 (3H, s), 3.11–2.97 (2H, m), 2.52–2.49 (2H, m), 2.34–2.17 (2H, m).

EXAMPLE 25

4-Chloro-2-{[(1R)-3-(cyclopropylamino)-1-phenylpropyl]oxy}-5-fluorobenzonitrile oxalate (R)-α-(2-Chloroethyl)benzenemethanol (341 mg, 2 mmol) was dissolved in tetrahydrofuran (10 ml) and treated with sodium hydride as a 60% suspension in mineral oil (480 mg, 3 mmol) followed after 10 minutes by 4-chloro-2,5-difluorobenzonitrile (347 mg, 2 mmol). The mixture was stirred at room temperature for 18 h before being treated with methanol (1 ml) and then water (10 ml). The tetrahydrofuran was then removed via heating the vessel to 80° C. and applying a nitrogen stream. Once the tetrahydrofuran was evaporated the residue was extracted into dichloromethane, dried over magnesium sulphate and concentrated in vacuo. The resultant material was re-dissolved into dimethylformamide (8 ml) and treated with sodium iodide (305 mg, 2.03 mmol), triethylamine (565 μl, 4.06 mmol) and cyclopropylamine (114 mg, 2 mmol) before being heated to 60° C. for 5 days. The mixture was filtered and purified via RPHPLC on the crude reaction material. The purified compound was then treated with 50% saturated oxalic acid in ether to produce 74 mg of a white powder that was collected via filtration.

MS APCI+ve$^m$/z 345/347 [(M+H)$^+$].

$^1$H NMR 400 MHz (d$_6$-DMSO) 7.97–7.87 (m, 1H), 7.53–7.25 (m, 6H), 5.69 (m, 1H), 3.28–3.07 (m, 2H), 2.80–2.68 (m, 1H), 2.45–2.29 (m, 1H), 2.29–2.12 (m, 1H), 0.85–0.74 (m, 4H).

EXAMPLE 26
4-Chloro-2-{[(1R)-3-(cyclopropylamino)-1-(3-furanyl)propyl]oxy}-5-fluorobenzonitrile oxalate Prepared by the method of Example 25 using (R)-α-(2-chloroethyl)-3-furanmethanol (321 mg, 2 mmols) and 4-chloro-2,5-difluorobenzonitrile (347 mg, 2 mmols) initially before converting into the title compound via in situ conversion to the iodo compound and treatment with cyclopropylamine. The free base was treated with a 50% saturated solution of oxalic acid in ether. The resultant white solid was collected via filtration to yield the title compound (14 mg, 1.6%).

MS APCI+ve$^m$/z 335/337 [(M+H)$^+$].

$^1$H NMR 400 MHz (d$_6$-DMSO) 8.01 (d, 1H), 7.70 (s, 1H), 7.70 (s, 1H), 7.59 (d, 1H), 6.53 (s, 1H), 5.72 (t, 1H), 3.15–2.99 (m, 2H), 2.97–2.87 (m, 1H), 2.40–2.26 (m, 1H), 2.24–2.09 (m, 1H), 0.78–0.66 (m, 4H).

EXAMPLE 27
4-Chloro-2-{[(1R)-3-(cyclopropylamino)-1-(3-thienyl)propyl]oxy}-5-fluorobenzonitrile oxalate Prepared by the method of Example 25 using (R)-α-(2-chloroethyl)-3-thiophenemethanol (Example 74 (d)) and 4-chloro-2,5-difluorobenzonitrile initially before converting into the title compound via in situ conversion to the iodo compound and treatment with cyclopropylamine The free base was treated with a 50% saturated solution of oxalic acid in ether. The resultant white solid was collected via filtration to yield the title compound (24 mg, 3%).

MS APCI+ve$^m$/z 351 [(M+H)$^+$].

$^1$H NMR 400 MHz (d$_6$-DMSO) 8.02 (d, 1H), 7.60 (s, 2H), 7.50 (d, 1H), 7.14 (d, 1H), 5.83 (t, 1H), 3.14–2.99 (m, 2H), 2.76–2.62 (m, 1H), 2.42–2.29 (m, 2H), 2.27–2.13 (m, 2H), 0.84–0.63 (m, 4H).

EXAMPLE 28
4-Bromo-2-{[(1R)-3-(cyclopropylamino)-1-(phenyl)propyl]oxy}-5-fluorobenzonitrile oxalate Prepared by the method of Example 25 using (R)-α-(2-chloroethyl)benzenemethanol and 4-bromo-2,5-difluorobenzonitrile initially before converting into the title compound via in situ conversion to the iodo compound and treatment with cyclopropylamine. The free base was treated with a 50% saturated solution of oxalic acid in ether. The resultant white solid was collected via filtration to yield the title compound (41 mg, 4.2%).

MS APCI+ve$^m$/z 390 [(M+H)$^+$].

$^1$H NMR 400 MHz (d$_6$-DMSO) δ 7.96 (d, 1H), 7.49 (d, 1H), 7.45–7.39 (m, 3H), 7.39–7.31 (m, 2H), 5.82–5.74 (m, 1H), 3.16–3.00 (m, 2H), 2.74–2.64 (m, 1H), 2.38–2.25 (m, 1H), 2.24–2.11 (m, 1H), 0.79–0.64 (m, 4H).

EXAMPLE 29
4-Bromo-2-{[(1R)-3-(cyclopropylamino)-1-(3-furanyl)propyloxy}-5-fluorobenzonitrile oxalate Prepared by the method of Example 25 using (R)-α-(2-chloroethyl)benzenemethanol and 4-bromo-2,5-difluorobenzonitrile initially before converting into the title compound via in situ conversion to the iodo compound and treatment with cyclopropylamine. The free base was treated with a 50% saturated solution of oxalic acid in ether. The resultant white solid was collected via filtration to yield the title compound (41 mg, 4.2%).

MS APCI+ve$^m$/z 380 [(M+H)$^+$].

$^1$H NMR 400 MHz (d$_6$-DMSO) 7.95 (d, 1H), 7.81 (s, 1H), 7.71–7.66 (m, 2H), 6.53 (s, 1H), 5.77–5.69 (m, 1H), 3.15–2.99 (m, 2H), 2.73–2.65 (m, 1H), 2.41–2.29 (m, 1H), 2.25–2.12 (m, 1H), 0.80–0.67 (m, 4H).

EXAMPLE 30
4-Bromo-2-{[(1R)-3-(cyclopropylamino)-1-(3-thienyl)propyl]oxy}-5-fluorobenzonitrile oxalate Prepared by the method of Example 25 using (R)-α-2-chloroethyl)-3-thiphenemethanol and 4-bromo-2,5 difluorobenzonitrile initially before converting into the title compound via in situ conversion to the iodo compound and treatment with cyclopropylamine. The free base was treated with a 50% saturated solution of oxalic acid in ether to yield the title compound (47 mg, 4.8%).

MS APCI+ve$^m$/z 396 [(M+H)$^+$].

$^1$H NMR 400 MHz (d$_6$-DMSO) 7.95 (d, 1H), 7.63–7.57 (m, 3H), 7.14 (d, 1H), 5.83 (t, 1H), 3.14–3.00 (m, 2H), 2.73–2.65 (m, 1H), 2.40–2.30 (m, 1H), 2.26–2.15 (m, 1H), 0.78–0.67 (m, 4H).

EXAMPLE 31
4-Chloro-5-fluoro-2-({(1R)-3-[(3-hydroxypropyl)amino]-1-phenylpropyl}oxy)benzonitrile oxalate Prepared by the method of Example 25 but treating the intermediate iodo compound with 3-amino-1-propanol (150 mg, 2 mmol) to yield the title compound (67 mg, 7.4%).

MS APCI+ve$^m$/z 363/365 [(M+H)$^+$].

$^1$H NMR 400 MHz (d$_6$-DMSO) 8.03 (d, 1H), 7.43 (m, 4H), 7.40 (d, 1H), 7.35 (m, 1H), 5.81–5.74 (m, 1H), 3.47 (t, 2H), 3.13–3.00 (m, 2H), 3.02–2.95 (m, 2H), 2.39–2.27 (m, 1H), 2.23–2.12 (m, 1H), 1.77–1.67 (m, 2H).

EXAMPLE 32
4-Chloro-5-fluoro-2-[[(1R)-1-(3-furanyl)-3-(3-hydroxypropyl)amino]propyl]oxy}benzonitrile oxalate Prepared by the method of Example 26 but treating the intermediate iodo compound with 3-amino-1-propanol (150 m, 2mmol) to yield the title compound (49 mg, 5.5%).

MS APCI+ve$^m$/z 353/355 [(M+H)$^+$].

1H NMR 400 MHz (d$_6$-DMSO) 8.01 (d, 1H), 7.81 (s, 1H), 7.70–7.69 (m, 1H), 7.59 (d, 1H), 6.54–6.53 (m, 1H), 5.76–5.71 (m, 1H), 3.48 (t, 2H), 3.07–3.01 (m, 2H), 3.02–2.97 (m, 2H), 2.41–2.31 (m, 1H), 2.26–2.15 (m, 1H), 1.78–1.69 (m, 2H).

EXAMPLE 33
4-Chloro-5-fluoro-2-{[(1R)-3-[(3-hydroxypropyl)amino]-1-(3-thienyl)propyl]oxy}benzonitrile oxalate Prepared by the method of Example 27 but treating the intermediate iodo compound with 3-amino-1-propanol (150 mg, 2 mmol) to yield the title compound (74 mg, 8%).

MS APCI+ve$^m$/z 369 [(M+H)$^+$].

$^1$H NMR 400 MHz (d$_6$-DMSO) 8.02 (d, 1H), 7.62–7.60 (m, 2H), 7.50 (d, 1H), 7.16–7.13 (m, 1H), 5.87–5.82 (m, 1H), 3.47 (t, 2H), 3.09–3.02 (m, 2H), 3.02–2.96 (m, 2H), 2.42–2.32 (m, 1H), 2.27–2.16 (m, 1H), 1.77–1.68 (m, 2H).

EXAMPLE 34
4-Bromo-5-fluoro-2-({(1R)-3-[(3-hydroxypropyl)amino]-1-phenylpropyl}oxy)benzonitrile oxalate Prepared by the method of Example 28 but treating the intermediate iodo compound with 3-amino-1-propanol (150 mg, 2 mmol) to yield the title compound (25 mg, 2.5%).

MS APCI+ve$^m$/z 407/409 [(M+H)$^+$].

$^1$H NMR 400 MHz (d$_6$-DMSO) 7.97 (d, 1H), 7.49 (d, 1H), 7.45–7.40 (m, 4H), 7.39–7.32 (m, 2H), 5.80–5.74 (m, 1H), 3.47 (t, 2H), 3.13–3.03 (m, 2H), 3.02–2.96 (m, 2H), 2.38–2.28 (m, 1H), 2.23–2.14 (m, 1H), 1.77–1.68 (m, 2H).

EXAMPLE 35
4-Bromo-5-fluoro-2-({(1R)-1-(3-furanyl)-3-[(3-hydroxypropyl)amino]propyl}oxy)benzonitrile oxalate Prepared by the method of Example 29 but treating the intermediate iodo compound with 3-amino-1-propanol (150 mg, 2 mmol) to yield the title compound (42 mg, 4.3%).

MS APCI+ve $^m$/z 399/401 [(M+H)$^+$].

$^1$H NMR 400 MHz (d$_6$-DMSO) 7.94 (d, 1H), 7.81–7.80 (m, 1H), 7.71–7.67 (m, 2H), 6.54–6.52 (m, 1H), 5.74 (t, 1H), 3.48 (t, 2H), 3.10–3.01 (m, 2H), 3.02–2.97 (m, 2H), 2.42–2.31 (m, 1H), 2.26–2.16 (m, 1H), 1.78–1.70 (m, 2H).

EXAMPLE 36

4-Bromo-5-fluoro-2-{[(1R)-3-[(3-hydroxypropyl)amino]-1-(3-thienyl)propyl]oxy}benzonitrile oxalate Prepared by the method of Example 30 but treating the intermediate iodo compound with 3-amino-1-propanol (150 mg, 2 mmol) to yield the title compound (42 mg, 4.3%).

MS APCI+ve $^m$/z 414/416 [(M+H)$^+$].

$^1$H NMR 400 MHz (d$_6$-DMSO) 7.95 (d, 1H), 7.64–7.57 (m, 3H), 7.16–7.12 (m, 1H), 5.88–5.81 (m, 1H), 3.47 (t, 2H), 3.10–3.01 (m, 2H), 3.02–2.97 (m, 2H), 2.42–2.30 (m, 1H), 2.28–2.16 (m, 1H), 1.78–1.68 (m, 2H).

EXAMPLE 37

2-[[(1R)-3-Amino-1-phenylpropyl]oxy]-4-(trifluoromethyl)benzonitrile oxalate a) (R)-α-(2-Azidoethyl)benzenemethanol (R)-α-(2-Chloroethyl)benzenemethanol (0.73 g, 4.3 mmol) and sodium azide (417 mg, 1.5 eq.) in DMSO (3 ml) was stirred and heated at 40° C. for 1.5 h. The reaction mixture was diluted with water (50 ml) and the products extracted into ethyl acetate(2×75 ml). The combined extracts were dried (magnesium sulphate) and concentrated to an oil. Purification was achieved on silica gel eluting with 50% diethyl ether/isohexane to afford the azide as a colourless oil (0.6 g, 79%).

$^1$H NMR 300 MHz (CDCl$_3$) 7.61–7.27 (5H, m), 4.88–4.82 (1H, m), 3.55–3.35 (2H, m), 2.11–1.89 (2H, m).

b) 2-[[(1R)-3-Azido-1-phenylpropyl]oxy]-4-(trifluoromethyl)benzonitrile

A mixture of the azido alcohol 37 (a) (0.49 g, 2.77 mmol) and 2-fluoro-4-(trifluoromethyl)benzonitrile (0.523 g, 2.77 mmol) in dry tetrahydrofuran (30 ml) under a nitrogen atmosphere was treated with sodium hydride (60% dispersion, 111 mg, 2.77 mmol). The mixture was stirred and heated 60° C. for 1.5 h, then quenched with water (150 ml). The products were extracted into diethyl ether (2×100 ml). The combined extracts were dried over magnesium sulphate, filtered and concentrated to. an oil. The crude material was purified on silica gel using 10% ether/isohexane to afford the title compound as a colourless oil (770 mg, 80%).

MS APCI+ve $^m$/z 319 [(M+H–28)].

c) 2-[[(1R)-3-Amino-1-phenylpropyl]oxy]-4-(trifluoromethyl)benzonitrile oxalate

A solution of 2-[[(1R)-3-azido-1-phenylpropyl]oxy]-4-(trifluoromethyl)benzonitrile (7.70 mg, 2.2 mmol) in tetrahydrofuran (50 ml) was treated with triphenylphosphine (1.5 eq.) and water (0.5 ml). The mixture was stirred at ambient temperature for 24 h then concentrated to an oil. The crude amine was purified on silica gel eluting with ethyl acetate, then 10% 7N ammonia in methanol/dichloromethane. The oil obtained was converted into an oxalate salt using 1 equivalent of oxalic acid in ethanol to afford the title compound as a colourless solid (510 mg, 56%).

MS APCI+ve $^m$/z 321 [(M+H)$^+$].

$^1$H NMR 300 MHz (d$_6$-DMSO) 8.0 (1H, d), 7.44–7.31 (7H, m), 5.93 (1H, dd), 3.04–2.9 (2H, m), 2.4–2.1 (2H, m).

EXAMPLE 38

2-[[(1R)-3-Amino-1-phenylpropyl]oxy]-4-chlorobenzonitrile a) 2-[[(1R)-3-Azido-1-phenylpropyl]oxy]-4-chlorobenzonitrile The sub title compound was prepared by the method of Example 37 (b) but using 4-chloro-2-fluorobenzonitrile.

$^1$H NMR 400 MHz (CDCl$_3$) 7.48–7.32 (6H, m), 6.95 (1H, dd), 6.79 (1H, d), 5.34 (1H, dd), 3.69–3.63 (1H, m), 3.5–3.44 (1H, m), 2.39–2.32 (1H, m), 2.14–2.05 (1H, m).

b) 2-[[(1R)-3-Amino-1-phenylpropyl]oxy]-4-chlorobenzonitrile oxalate

The sub title compound was prepared by the method of Example 37 (c) but using 2-[[(1R)-3-azido-1-phenylpropyl]oxy]-4-chlorobenzonitrile.

MS APCI+ve $^m$/z 287/9 [(M+H)$^+$].

$^1$H NMR 400 MHz (d$_6$-DMSO) 7.79 (1H, d), 7.46–731 (5H, m), 7.19–7.14 (2H, m), 5.81 (1H, dd), 3.01–2.74 (2H, m), 2.35–2.08 (2H, m).

EXAMPLE 39

4-Chloro-5-fluoro-2-[[(1R)-3-(methylamino)-1-phenylpropyl]oxy]benzonitrile a) [(3R)-3-(5-Chloro-2-cyano-4-fluorophenoxy)-3-phenylpropyl]methyl carbamic acid 1,1-dimethylethyl ester The sub title compound was prepared by the method of Example 3 (b) using 4-chloro-2,5-difluorobenzonitrile and dimethylformamide as solvent.

MS APCI+ve $^m$/z 319/21 [(M–(C$_4$H$_9$)+H)$^+$].

b) 4-Chloro-5-fluoro-2-[[(1R)-3-(methylamino)-1-phenylpropyl]oxy]benzonitrile oxalate

[(3R)-3-(5-Chloro-2-cyano-4-fluorophenoxy)-3-phenylpropyl]methyl carbamic acid 1,1-dimethylethyl ester (220 mg, 0.525 mmol) was stirred in a 4N solution of hydrogen chloride in dioxan (20 ml) for 20 minutes. The hydrochloride salt was,applied to a silica gel column and eluted with 10% 7N ammonia in methanol/dichloromethane. The free base was then converted into an oxalate salt with 1 equivalent of oxalic acid in ethanol. The title compound was obtained as a colourless solid (175 mg, 82%).

MS APCI+ve $^m$/z 319/321[(M+H)$^+$].

$^1$H NMR 300 MHz (d$_6$-DMSO) 8.02 (1H, d), 7.43–7.31 (6H, m), 5.79 (1H, dd), 3.09–2.93 (2H, m), 2.53 (3H, s), 2.4–2.1 (2H, m).

EXAMPLE 40

2-[[(1R)-3-Amino-1-phenylpropyl]oxy]-4-chloro-5-fluorobenzonitrile oxalate a) 2-[[(1R)-3-Azido-1-phenylpropyl]oxy]-4-chloro-5-fluorobenzonitrile A mixture of the azido alcohol 37 (a) (8 g, 0.045 mol) and 4-chloro-2,5-difluorobenzonitrile (7.83 g, 0.045 mol) in dry dimethylformamide (70 ml) under nitrogen atmosphere was treated with sodium hydride (60% dispersion, 1.81 g, 0.045 mol). The mixture was stirred and heated to 60° C. for 2 h, then quenched with water (500 ml). The products were extracted into diethyl ether (2×300 ml). The combined extracts were dried over magnesium sulphate, filtered and concentrated to an oil. The crude material was purified on silica gel using 20% ether/isohexane to afford the title compound as a colourless oil (9.4 g, 80%).

$^1$H NMR 300 MHz (CDCl$_3$) 7.43–7.3 (6H, m), 6.84 (1H, dd), 5.29 (1H, dd), 3.7–3.42 (2H, m), 2.4–2.04 (2H, m).

b) 2-[[(1R)-3-Amino-1-phenylpropyl]oxy]-4-chloro-5-fluoro benzonitrile oxalate

2-[[(1R)-3-Azido-1-phenylpropyl]oxy]-4-chloro-5-fluorobenzonitrile (Example 40 (a)) was reduced in an analogous procedure to that described for Example 37 (c).

MS APCI+ve $^m$/z 305/7 [(M+H)$^+$].
$^1$H NMR 400 MHz (d$_6$-DMSO) 8.01 (1H, d), 7.44–7.31 (6H, m), 5.78 (1H, dd), 2.91–2.81 (2H, m), 2.28–2.05 (2H, m).

EXAMPLE 41

γ-[5-Chloro-2-(trifluoromethyl)phenoxy]-N-methylbenzenepropanamine hydrochloride The title compound was prepared by the method of Example 3 (b) using racemic (3-hydroxy-3-phenylpropyl) carbamic acid 1,1-dimethylethyl ester and 2,4-dichloro-1-(trifluoromethyl)benzene to give 70 mg of the product as a colourless solid.

MS APCI+ve $^m$/z 344/6 [(M+H)$^+$].
$^1$H NMR 300 MHz (d$_6$-DMSO) 8.93–8.79 (m, 2H), 7.65 (d, 1H), 7.45–7.39 (m, 4H), 7.38–7.30 (m, 1H), 7.15 (s, 1H), 7.13 (d, 1H), 5.88 (dd, 1H), 3.01–2.90 (m, 2H), 2.55 (s, 3H), 2.37–2.12 (m, 2H).

EXAMPLE 42

2-[[(1R)-3-(Methylamino)-1-phenylpropyl]oxy]-4-(trifluoromethyl)benzonitrile hydrochloride The title compound was prepared by the method of Example 3 (b) using 2-fluoro-4-(trifluoromethyl) benzonitrile to give 290 mg of the product as a white solid.

MS APCI+ve $^m$/z 335 [(M+H)$^+$].
$^1$H NMR 400 MHz (d$_6$-DMSO) 9.12–8.99 (m, 2H), 8.00 (d, 1H), 7.50–7.30 (m, 7H), 6.06 (dd, 1H), 3.10–2.96 (m, 2H), 2.57 (s, 3H), 2.46–2.20 (m, 2H).

EXAMPLE 43

4-Chloro-5-fluoro-2-[[(1R)-3-[[(5-methylpyrazinyl)methyl]amino]-1-phenylpropyl]oxy]benzonitrile dihydrochloride a) 4-Chloro-2-[[(1R)-3-chloro-1-phenylpropyl]oxy]-5-fluorobenzonitrile 4-Chloro-2,5-difluorobenzonitrile (1.0 g, 5.8 mmol) and S-α-(2-chloroethyl)benzene methanol (1.0 g, 5.86 mmol) were dissolved in dimethylformamide (10 ml) and 60% NaH (350 mg, 8.7 mmol) added portionwise over 5 minutes. The mixture was stirred for 2 h, quenched with water and extracted with ethyl acetate. The extracts were washed with water (×3), dried over magnesium sulphate, filtered and evaporated. Purification by flash chromatography (5% ethyl acetate/hexane) gave 1.8 g (96%) of the product as a colourless oil.

$^1$H NMR 300 MHz (CDCl$_3$) 7.44–7.32 (m, 5H), 7.31 (d, 1H), 6.87 (d, 1H), 5.44 (dd, 1H), 3.93–3.82 (m, 1H), 3.67–3.57 (m, 1H), 2.64–2.51 (m, 1H), 2.31–2.18)m, 1H).

b) 4-Chloro-5-fluoro-2-{[(1R)-3-iodo-1-phenylpropyl]oxy}benzonitrile

4-Chloro-2-{[(1R)-3-chloro-1-phenylpropyl]oxy}-5-fluorobenzonitrile (1.8 , 5.6 mmol) and sodium iodide (12.8 g, 100 mmol) were dissolved in acetone (50 ml) and heated under reflux for 24 h. The reaction mixture was cooled, filtered and evaporated. The semi-solid residue was dissolved in toluene, filtered and evaporated again to give 2.3 g of the crude product as a yellow oil. This was used without purification for the next step.

c) 4-Chloro-5-fluoro-2-[[(1R)-3-[[(5-methylpyrazinyl)methyl]amino]-1-phenylpropyl]oxy]benzonitrile dihydrochloride 4-Chloro-5-fluoro-2-{[(1R)-3-iodo-1-phenylpropyl]oxy}benzonitrile (200 mg, 0.48 mmol), 5-methyl-2-pyrazinemethanamine (120 mg, 0.96 mmol) and triethylamine (335 μl, 2.4 mmol) were stirred in DMSO (5 ml) for 48 h. The mixture was washed with water and purified by chromatography (5% 1M ammonia-methanol/dichloromethane). The eluent was evaporated and the residue treated with 4M hydrogen chloride in dioxan (5 ml). The solvent was evaporated, azeotroped twice with toluene and triturated with ether to give the required product as a white solid.

MS APCI+ve $^m$/z 411 [(M+H)$^+$].
$^1$H NMR 400 MHz (d$_6$-DMSO) 8.71 (s, 1H), 8.58 (s, 1H), 8.01 (d, 1H), 7.49 (d, 1H), 7.46–7.30 (m, 5H), 5.96 (dd, 1H), 4.36 (t, 2H), 3.20–3.02 (m, 2H), 2.53 (s, 3H), 2.52–2.28 (m, 2H).

EXAMPLE 44

4-Chloro-5-fluoro-2-[[(1R)-3-[(1H-imidazol-2-ylmethyl)amino]-1-phenylpropyl]oxy]benzonitrile dihydrochloride The title compound was prepared by the method of Example 43 (c) using 1H-imidazole-2-methanamine to give the title product as a white solid.

MS APCI+ve $^m$/z 385 [(M+H)$^+$].
$^1$H NMR 400 MHz (d$_6$-DMSO) 8.01 (d, 1H), 7.72 (s, 2H), 7.51 (d, 2H), 7.49–7.32 (m, 5H), 6.00 (dd, 1H), 4.54 (s, 2H), 3.26–3.12 (m, 2H), 2.50–2.25 (m, 2H).

EXAMPLE 45

2-[[(1R)-3-Amino-1-(3-isoxazolyl)propyl]oxy]-4-(trifluoromethyl)-benzonitrile fumarate a) 2-[[(1R)-3-Azido-1-(3-isoxazolyl)propyl]oxy]-4-(trifluoromethyl)benzonitrile The product from Example 93 (a) (0.17 g) was reacted with 4-(trifluoromethyl)-2-fluoro-benzonitrile (0.3 g) using the procedure described in Example 93 (b) to afford the product as a gum which was carried on directly to the next step.

b) 2-[[(1R)-3-Amino-1-(3-isoxazolyl)propyl]oxy]-4-(trifluoromethyl)benzonitrile fumarate The product from step (a) was subjected to the procedure described in Example 90 (b) to afford the product as a solid (0.1 g).

MS APCI+ve $^m$/z 312 [(M+H)$^+$].
$^1$H NMR 300 MHz (d$_6$-DMSO) 8.99 (1H, d), 8.03 (1H, d), 7.60 (1H, s), 7.50 (1H, d), 6.74 (1H, d), 6.43 (2H, s), 6.24–6.15 (1H, m), 2.98 (2H, dd), 2.48–2.35 (1H, m), 2.34–2.21 (1H, m).

EXAMPLE 46

4-Chloro-2-[[(1R)-3-[[2-(dimethylamino)ethyl]amino]-1-phenylpropyl]oxy]-5-fluoro benzonitrile dihydrochloride The title compound was prepared by the method of Example 43 (c) using N$^1$,N$^1$-dimethyl-1,2-ethanediamine to give the product as a white solid.

MS APCI+ve $^m$/z 376 [(M+H)$^+$].
$^1$H NMR 400 MHz (d$_6$-DMSO) 8.02 (d, 1H), 7.52 (d, 1H), 7.48–7.32 (m, 5H), 5.95 (dd, 3H), 3.47–3.39 (m, 2H), 3.39–3.30 (m, 2H), 3.19–3.03 (m, 2H), 2.83 (s, 6H), 2.47–2.22 (m, 2H).

EXAMPLE 47

4-Chloro-5-fluoro-2-[[(1R)-3-[[2-(4-morpholinyl)ethyl]amino]-1-phenylpropyl]oxy]benzonitrile dihydrochloride The title compound was prepared by the method of Example 43 (c) using 4-morpholineethanamine to give the product as a white solid.

MS APCI+ve $^m$/z 418 ([M+H]$^+$].
$^1$H NMR 400 MHz (d$_6$-DMSO) 9.75–9.50 (m, 2H), 8.02 (d, 1H), 7.51 (d, 1H), 7.48–7.32 (m, 5H), 5.95 (dd, 1H), 4.07–3.91 (m, 2H), 3.86–3.70 (m, 2H), 3.61–3.34 (m, 6H), 3.22–3.01 (m, 4H), 2.50–2.20 (m, 2H).

EXAMPLE 48

4-Chloro-5-fluoro-2-[[(1R)-3-[[2-(1H-imidazol-1-yl)ethyl]amino]-1-phenylpropyl]oxy]benzonitrile dihydrochloride The title compound was prepared by the method of Example 43 (c) using 1H-imidazole-1-ethanamine to give the product as a white solid.

MS APCI+ve $^m$/z 399 [(M+H)$^-$].

$^1$H NMR 300 MHz (d$_6$-DMSO) 9.17–9.12 (m, 1H), 8.01 (d, 1H), 7.82–7.78 (m, 1H), 7.69–7.65 (m, 1H), 7.53 (d, 1H), 7.49–7.30 (m, 5H), 5.98 (dd, 1H), 4.61 (t, 2H), 3.50 (t, 2H), 3.13–2.99 (m, 2H), 2.45–2.22 (m, 2H).

EXAMPLE 49
4-Chloro-5-fluoro-2-[[(1R)-3-[[2-(1 H-imidazol-4-yl)ethyl] amino]-1-phenylpropyl]oxy]benzonitrile dihydrochloride The title compound was prepared by the method of Example 43 (c) using 1H-imidazole-4-ethanamine to give the product as a white solid.

MS APCI+ve $^m$/z 399 [(M+H)$^-$].

EXAMPLE 50
4-Chloro-5-fluoro-2-[[(1R)-3-[(2-hydroxyethyl)amino]-1-phenylpropyl]oxy]benzonitrile hydrochloride The title compound was prepared by the method of Example 43 (c) using 2-aminoethanol to give the product as a white solid.

MS APCI+ve $^m$/z 349 [(M+H)$^-$].

$^1$H NMR 400 MHz (d$_6$-DMSO) 9.10–8.90 (m, 2H), 8.02 (d, 1H), 7.49 (d, 1H), 7.47–7.39 (m, 4H), 7.38–7.32 (m, 1H), 5.91 (dd, 1H), 5.26 (t, 2H), 3.67 (q, 2H), 3.13–2.96 (m, 2H), 2.46–2.21 (m, 2H).

EXAMPLE 51
2-[[(1R)-3-[(2-Aminoethyl)amino]-1-phenylpropyl]oxy]-4-chloro-5-fluorobenzonitrile dihydrochloride The title compound was prepared by the method of Example 43 (c) using 1,2-ethanediamine to give the product as a white solid.

MS APCI+ve /z 348 [(M+H)$^+$].

$^1$H NMR 400 MHz (d$_6$-DMSO) 8.01 (d, 1H), 7.51 (d, 1H), 7.48–7.32 (m, 5H), 5.98 (dd, 1H), 3.37–3.30 (m, 2H), 3.26–3.16 (m, 2H), 3.13–3.04 (m, 2H), 2.48–2.20 (m, 2H).

EXAMPLE 52
4-Chloro-5-fluoro-2-[[(1R)-1-phenyl-3-[(3 3.3-trifluoropropyl)amino]propyl]oxy]benzonitrile trifluoroacetate 2-[[(1R)-3-Amino-1-phenylpropyl]oxy]-4-chloro-5-fluorobenzonitrile (300 mg, 0.99 mmol) and 3,3,3-trifluoropropanal (123 mg, 1.2 mmol) were dissolved in dichloromethane (10 ml), 4A sieves added, followed by sodium triacetoxyborohydride (320 mg, 1.5 mmol) and stirred for 20 h. The reaction mixture was washed with saturated aqueous sodium hydrogen carbonate, dried over magnesium sulphate, filtered and evaporated. The residue was purified by reverse phase chromatography (0.1% aqueous trifluoroacetic acid/methanol) to give 280 mg of the product as a white solid.

MS APCI+ve $^m$/z 401 [(M+H)$^+$].

$^1$H NMR 300 MHz (d$_6$-DMSO) 8.99–8.82 (m, 2H), 8.04 (d, 5H), 7.48–7.30 (m, 2H), 5.78 (dd, 1H), 3.26 (t, 2H), 3.21–3.03 (m, 2H), 2.79–2.61 (m, 2H), 2.43–2.13 (m, 2H).

EXAMPLE 53
2-{[(1R)-3-amino-1-(2-thiazolyl)propyl]oxy}-4-chlorobenzonitrile hydrochloride.
a) [3-Oxo-3-(2-thiazolyl)propyl]carbamic acid 1,1-dimethylethyl ester To a solution of 2-bromothiazole (5.035 g, 30.7 mmol) in dry tetrahydrofuran (125 ml) at −78° C. under nitrogen was added a solution of n-butyllithium in hexanes (1.6 M, 17.6 ml, 28.2 mmol) over a period of 30 minutes, followed by a solution of [3-(methoxymethylamino)-3-oxopropyl] carbamic acid 1,1-dimethylethyl ester (2.976 g, 12.8 mmol) in dry tetrahydrofuran (30 ml) added over 30 minutes. The reaction mixture was allowed to warm up to 0° C., quenched with saturated ammonium chloride and extracted with ethyl acetate (3×100 ml). The combined extracts were washed with water (3×50 ml) and saturated brine solution (1×100 ml), dried (magnesium sulphate) and concentrated in vacuo to leave a crude orange oil. Flash chromatography (silica, 25% ethyl acetate in isohexane) gave 2.2 g of a pale yellow oil (67%).

MS APCI+ve$^m$/z 201 ([(M(—C$_4$H$_9$)+H)$^+$].

$^1$H NMR 300 MHz (CDCl$_3$) 8.01 (1H, m), 7.69 (1H, m), 5.05 (1H, br s), 3.57 (2H, q), 3.39 (2H, t), 1.46 (9H, s).

b) [(3R)-3-Hydroxy-3-(2-thiazolyl)propyl]carbamic acid 1,1-dimethylethyl ester

To a solution of (S)-3-methyl-CBS-oxazaborolidine (1M solution in toluene, 0.43 ml) in dry tetrahydrofuran (30 ml) at −10° C. under nitrogen, was added borane-tetrahydrofuran complex (1M in tetrahydrofuran, 2.58 ml) and stirred at −10° C. for 15 minutes. A solution of [3-oxo-3-(2-thiazolyl)propyl]carbamic acid 1,1-dimethylethyl ester (1.1 g, 4.3 mmol) in dry tetrahydrofuran (20 ml) was added dropwise over 45 minutes and the resulting mixture was allowed to warm up to room temperature over 16 h. Methanol (10 ml) was added and the mixture was stirred at room temperature for 15 minutes before the solvent was removed at reduced pressure. Methanol (10 ml) was again added and removed at reduced pressure to leave a crude yellow oil. Flash chromatography (silica, 25 to 100% ethyl acetate in isohexane) gave 0.75 g of a clear gum (67%).

MS APCI+ve $^m$/z 259 [(M+H)$^+$].

$^1$H NMR 300 MHz (CDCl$_3$) 7.72 (1H, d), 7.29 (1H, d), 5.06–5.02 (1H, m), 4.92 (1H, br s), 4.71 (1H, s), 3.70–3.58 (1H, m), 3.25–3.16 (1H, m), 2.24 (1H, m), 1.93–1.87 (1H, m), 1.44 (9H, s).

c) [(3R)-3-(5-Chloro-2-cyanophenoxy)-3-(2-thiazolyl) propyl]carbamic acid 1,1-dimethylethyl ester.

To a solution of 4-chloro-2-fluorobenzonitrile (156 mg, 1 mmol) and [(3R)-3-hydroxy-3-(2-thiazolyl)propyl]carbamic acid 1,1-dimethylethyl ester (258 mg, 1 mmol) in dry dimethylformamide (3 ml), was added sodium hydride (60% dispersion in oil, 40 mg, 1 mmol) and the mixture was stirred at room temperature for 16 h. The reaction was quenched with methanol and partitioned between ethyl acetate and water. The combined extracts were washed with water (3×25 ml) and saturated brine solution, dried (magnesium sulphate) and concentrated in vacuo to leave a crude yellow gum. Flash chromatography (silica, 15% ethyl acetate in isohexane) gave 345 mg of a white solid (86%).

MS APCI+ve$^m$/z 394/396 [(M+H)$^+$].

$^1$H NMR 300 MHz (CDCl$_3$) 7.79 (1H, d), 7.49 (1H, d), 7.38 (1H, d), 7.06 (1H, d), 7.02 (1H, dd), 5.72 (1H, dd), 4.80 (1H, bd s), 3.56–3.20 (2H, m), 2.50–2.20 (2H, m), 1.44 (9H, s).

d) 2-{[(1R)-3-Amino-1-(2-thiazolyl)propyl]oxy}-4-chlorobenzonitrile hydrochloride To a solution of [(3R)-3-(5-chloro-2-cyanophenoxy)-3-(2-thiazolyl)propyl]-carbamic acid 1,1-dimethylethyl ester (140 mg, 0.36 mmol) in dry dioxan (3 ml) was added 4M HCl in dioxan (1 ml) and the mixture was stirred at room temperature for 16 h. The precipitate was collected, washed with ethyl acetate and vacuum dried to leave 106 mg of a white solid (90%).

MS APCI+ve$^m$/z 294/296 [(M+H)$^+$].

$^1$H NMR 300 MHz (d$_6$-DMSO) δ ppm:8.16 (3H, br s), 7.90–7.83 (3H, m), 7.52 (1H, d), 7.26 (1H, dd), 6.31 (1H, dd), 3.10–2.96 (2H, m), 2.48–2.38 (2H, m).

EXAMPLE 54
4-Chloro-2-{[(1R)-3-(methylamino)-1-(2-thiazolyl)propyl]oxy}benzonitrile hydrochloride a) [(3R)-3-(5-Chloro-2-cyanophenoxy)-3-(2-thiazolyl)propyl]methylcarbamic acid 1,1-dimethylethyl ester To a solution of [(3R)-3-(5-chloro-2-cyanophenoxy)-3-(2-thiazolyl)propyl]-carbamic acid 1,1-dimethylethyl ester (200 mg, 0.51 mmol) in dry tetrahydrofuran (10 ml), was added sodium hydride (56 mg, 60% dispersion in oil, 1.41 mmol) and stirred at room temperature for 15 minutes. Iodomethane (1.325 g, 0.58 ml, 4.7 mmol) was added. The reaction was stirred at room temperature for 18 h, quenched with saturated ammonium chloride solution and partitioned between ethyl acetate and water. The combined extracts were washed with water (3×25 ml) and saturated brine solution, dried (magnesium sulphate) and concentrated in vacuo to leave a crude yellow gum. Flash chromatography (silica, 25% ethyl acetate in isohexane) afforded 175 mg of an opaque oil (98%).

MS APCI+ve$^m$/z 408/410 [(M+H)$^+$].

$^1$H NMR 300 MHz (CDCl$_3$) 7.79 (1H, d), 7.49 (1H, d), 7.37 (1H, d), 7.07 (1H, s), 7.01 (1H, d), 5.68–5.63 (1H, m), 3.70–3.56 (1H, m), 3.43–3.33 (1H, m), 2.88 (3H, s), 2.45–2.28 (2H, m), 1.44 (9H, s).

b) 4-Chloro-2-{[(1R)-3-(methylamino)-1-(2-thiazolyl)propyl]oxy}benzonitrile hydrochloride The title compound was made using the same method as in Example 53 (d) to give 175 mg of a white solid (99%).

MS APCI+ve$^m$/z 308/310 [(M+H)$^+$].

$^1$H NMR 300 MHz (d$_6$-DMSO) 7.90–7.83 (3H, m), 7.56–7.51 (1H, m), 7.27 (1H, d), 6.35–6.25 (1H, m), 3.29 (3H, s), 3.09 (2H, t), 2.60–2.54 (2H, m).

EXAMPLE 55
(R)-γ-(2.5-Dichlorophenoxy)-2-thiazolepropanamine hydrochloride a) [(3S-3-Hydroxy-3-(2-thiazolyl)propyl]carbamic acid 1,1-dimethylethyl ester To a solution of (R)-3-methyl-CBS-oxazaborolidine (1M solution in toluene, 0.43 ml) in dry tetrahydrofuran (30 ml) at −10° C. under nitrogen was added borane-tetrahydrofuran complex (1M in tetrahydrofuran, 2.58 ml) and stirred at −10° C. for 15 minutes. A solution of [3-oxo-3-(2-thiazolyl)propyl]carbamic acid 1,1-dimethylethyl ester (1.1 g, 4.3 mmol) in dry tetrahydrofuran (20 ml) was added dropwise over 45 minutes and the resulting mixture was allowed to warm up to room temperature over 16 h. Methanol (10 ml) was added and the mixture was stirred at room temperature for 15 minutes before the solvent was removed at reduced pressure. Methanol (10 ml) was again added and removed at reduced pressure to leave a crude yellow oil. Flash chromatography (silica, 25 to 100% ethyl acetate in isohexane) afforded 0.74 g (67%) of a clear gum.

MS APCI+ve$^m$/z 259 [(M+H)$^+$].

$^1$H NMR 300 MHz (CDCl$_3$) 7.72 (1H, d), 7.29 (1H, d), 5.06–5.02 (1H, m), 4.95 (1H, bd s), 4.75 (1H, s), 3.70–3.58 (1H, m), 3.25–3.16 (1H, m), 2.24–2.16 (1H, m), 1.93–1.87 (1H, m), 1.44 (9H, s).

b) [(3R)-3-(2,5-Dichlorophenoxy)-3-(2-thiazolyl)propyl]carbamic acid 1,1-dimethylethyl ester.

To a solution of 2,5-dichlorophenol (163 mg, 1 mmol) [(3S)-3-hydroxy-3-(2-thiazolyl)propyl]carbamic acid 1,1-dimethylethyl ester (258 mg, 1 mmol) and triphenylphosphine (315 mg, 1.2 mmol) in dry tetrahydrofuran (30 ml) at 0° C. under nitrogen, was added diisopropyl azodicarboxylate (243 mg, 0.24 ml, 1.2 mmol) dropwise over 5 minutes. The mixture was stirred at room temperature for 16 h before the reaction was concentrated in vacuo to leave a crude yellow gum. Flash chromatography (silica, 15% ethyl acetate in isohexane) afforded 245 mg of a clear oil (63%).

MS APCI+ve$^m$/z 403/405/407 [(M+H)$^+$].

$^1$H NMR 300 MHz (CDCl$_3$) 7.79 (1H, d), 7.35 (1H, d), 7.29 (1H, d), 6.93 (1H, d), 6.90 (1H, dd), 5.66 (1H, dd), 5.03 (1H, bd s), 3.50–3.20 (2H, m), 2.45–2.25 (2H, m), 1.43 (9H, s).

c) (R)-γ-(2,5-Dichlorophenoxy)-2-thiazolepropanamine hydrochloride

The title compound was made using the method of Example 53 (d) to give 144 mg of a white solid (70%).

MS APCI+ve$^m$/z 303/305 [(M+H)$^+$].

$^1$H NMR 300 MHz (d$_6$-DMSO) 7.95 (3H, m), 7.78 (1H, d), 7.56 (1H, d), 7.53 (1H, d), 7.34 (1H, dd), 5.36–5.30 (1H, m), 3.08–2.84 (2H, m), 2.46–2.26 (2H, m).

EXAMPLE 56
2-[3-Amino-1-(2-oxazolyl)propoxy]-4-chlorobenzonitrile oxalate a) 3-Chloro-1-(2-oxazolyl)-1-propanone To a solution of oxazole (2.93 g, 42.5 mmol) in tetrahydrofuran (150 ml) at −70° C. under a nitrogen atmosphere was added n-butyllithium (17 ml of a 2.5M solution in hexanes) dropwise and the solution stirred for 20 minutes. Zinc chloride (84.9 ml of a 1M solution in diethyl ether) was added and the solution warmed to 0° C. over 45 minutes. Solid cuprous iodide (8.09 g, 42.5 mmol) was added and after 10 minutes, 3-chloropropionyl chloride (8.38 ml, 87.8 mmol) was added. After 1 h, ethyl acetate and aqueous ammonium chloride solution were added. The organic layer was separated and washed sequentially with aqueous ammonium chloride solution, water and brine. The solution was dried (sodium sulphate) and evaporated to yield 15.5 g of the crude product as a red oil. This mixture was used without further purification.

$^1$H NMR 300 MHz (CDCl$_3$) 7.86 (1H, s), 7.36 (1H, s), 3.93 (2H, t), 3.57 (2H, m).

b) R-α-(2-Azidoethyl)-2-oxazolemethanol (S)-2-Methyl-CBS-oxazaborolidine (0.72 ml of a 1M solution in toluene) was added to tetrahydrofuran (5 ml) under a nitrogen atmosphere and the solution cooled to −5° C. Borane-tetrahydrofuran complex (7.2 ml of a 1M solution in tetrahdrofuran) was added dropwise and the solution stirred for 10 minutes. A solution of the crude product from Example 56(a) (ca. 7.24 mmol) in tetrahydrofuran (7 ml) was added dropwise and the reaction warmed slowly to 0° C. over 16 h. Methanol (20 ml) was cautiously added and the volatiles removed in vacuo. Two further methanol addition/solvent evaporation cycles were performed. The residue was purified by flash chromatography using 10–40% ethyl acetate/isohexane as eluent to give 724 mg of a colourless oil. This was taken up into dimethylsulfoxide (5 ml), solid sodium azide (450 mg) added and the reaction heated at 65° C. for 16 h. After cooling to room temperature, water was added and the solution extracted with diethyl ether (3×). The combined organic extracts were dried (sodium sulphate) and the solvent removed in vacuo to yield 490 mg of the sub title compound as an orange oil that was used without further purification.

$^1$H NMR 300 MHz (CDCl$_3$) 7.65 (1H, s), 7.10 (1H, s), 4.97 (1H, dt), 3.63–3.47 (2H, m), 3.05 (1H, bs), 2.28–2.07 (2H, m).

c) 2-[3-Amino-1-(2-oxazolyl)propoxy]-4-chlorobenzonitrile oxalate

To a solution of the product from Example 56 (b) (160 mg) in dimethylformamide (2 ml) was added sodium hydride (76 mg of a 60% dispersion in mineral oil) and the reaction stirred for 1 h. Solid 4-chloro-2-fluoro-benzonitrile (296 mg) was added and the reaction stirred for 2 h. Water was added and the solution extracted with diethyl ether. The organic extract was separated, dried (sodium sulphate) and the solvent removed in vacuo. The residue was taken up in tetrahydrofuran (4 ml) and triphenylphosphine (283 mg) added. After 5 minutes, water (1 ml) was added and the reaction stirred for 16 h. Further water (2 ml) was added and the reaction stirred at 55° C. for 3 h and then 48 h at room temperature. The reaction was poured into ethyl acetate/aqueous 1N sodium hydroxide. The organic extract was separated, dried (sodium sulphate) and the solvent removed in vacuo. Purification by RP-HPLC afforded the free base of the title product (20 mg) as a white solid. This was taken up in diethylether/dichloromethane (1:1) and a solution of oxalic acid (15 mg) in diethyl ether (1 ml) added. The resulting solid was filtered off and dried in vacuo to yield 4 mg of the title product as a hydroscopic white solid.

MS APCI+ve$^m$/z 278 [(M+H)$^+$].

$^1$H NMR 400 MHz (d$_4$-MeOH) 7.87 (1H, s), 7.66 (1H, d), 7.34 (1H, s), 7.22 (1H, d), 7.17 (1H, s), 3.21 (1H, m), 3.10 (1H, m), 2.73 (1H, ddd), 2.46 (1H, ddd).

EXAMPLE 57

γ-(2,5-Dichlorophenoxy)-2-oxazolepropanamine oxalate

The title compound was prepared from the product from Example 56 (b) and 1,4-dichloro-2-fluoro-benzene using similar procedures to Example 56 (c). Final purification was by recrystallisation (2-propanol/methanol/diethyl ether) to afford a beige solid.

MS APCI+ve$^m$/z 287 [(M+H)$^+$].

$^1$H NMR 400 MHz (d$_4$-MeOH) 7.96 (1H, s), 7.37 (1H, d), 7.23 (1H, s), 7.18 (1H, m), 7.02 (1H, dd), 5.70 (1H, dd), 3.28 (2H, m), 2.59 (1H, m), 2.47 (1H, m).

EXAMPLE 58

2-[[-3-Amino-1-(3-pyridinyl)propyl]oxy]-4-chloro-5-fluorobenzonitrile oxalate a) [3-Oxo-3-(3-pyridinyl)propyl]carbamic acid, 1,1-dimethylethylester Isopropylmagnesium bromide (7.1 ml, 2M in tetrahydrofuran, 14.2 mmol) was added to a solution of 3-bromopyridine (2.24 g, 14.2 mmol) in tetrahydrofuran (15 ml) at 0° C. and stirred at 20° C. for 1 h. A solution of 1,1-dimethylethyl [3-(methoxymethylamino)-3-oxopropyl carbamate (1.08 g, 4.65 mmol) in tetrahydrofuran (6 ml) was added and the mixture was stirred for 18 h. The mixture was quenched with saturated aqueous ammonium chloride and extracted with diethyl ether (three times) The combined organic extracts were dried (sodium sulphate) and evaporated to give an oil. Purification by chromatography on silica eluting with petrol-acetone gave 568 mg (49%) of the sub-title compound as a colourless oil.

MS APCI+ve$^m$/z 251 [(M+H)$^+$].

b) [3-Hydroxy-3-(3-pyridinyl)propyl]carbamic acid, 1,1-dimethylethyl ester

Borane (3.0 ml, 1M in tetrahydrofuran) was added to a solution of (3aS)-tetrahydro-1-methyl-3,3-diphenyl-3H-pyrrolo[1,2-c][1,3,2]oxazaborole (0.22 ml, 1M in toluene) in tetrahydrofuran (5 ml) at 0° C. A solution of the product from step (a) (1.13 g, 4.52 mmol) in tetrahydrofuran (3 ml) was added over 30 minutes and then stirred at 20° C. for 24 h. Methanol was added and the solution was evaporated and methanol (15 ml) and 2M hydrochloric acid (5 ml) were added and stirred for 45 minutes. Aqueous potassium carbonate and di-tert-butyldicarbonate (250 mg) were added and the mixture was extracted with ethyl acetate (2×) and dichloromethane (4×). ) The organic extracts were dried (sodium sulphate), evaporated and purified by chromatography on silica eluting with dichloromethane—methanol to give 928 mg (73%) of the sub-title compound as a colourless oil.

MS APCI+ve$^m$/z 253 [(M+H)$^+$].

c) [(3-(5-chloro-2-cyano-4-fluorophenoxy)-3-(3-pyridinyl)propyl]carbamic acid, 1,1 dimethylethyl ester Sodium hydride (141 mg, 60% dispersion in oil) was added to a solution of the product from step (b) (785 mg, 2.96 mmol) and 4-chloro-2,5-difluorobenzonitrile (546 mg, 3.75 mmol) in tetrahydrofuran (9 ml) and the resultant suspension was stirred for 0.5 h. The mixture was quenched with saturated aqueous ammonium chloride, basified to pH 8 and extracted with ethyl acetate (three times). The combined organic extracts were dried (sodium sulphate), evaporated and purified by chromatography on silica eluting with petrol—acetone to give 1.05 g (88%) of the sub-title compound as a colourless oil.

MS APCI+ve$^m$/z 406 [(M+H)$^+$].

d) 2-[[-3-Amino-1-(3-pyridinyl)propyl]oxy]-4-chloro-5-fluorobenzonitrile oxalate A solution of the product from step (c) (227 mg, 0.56 mmol) in 4M HCl in dioxan (4 ml) was stirred for 0.5 h. Aqueous potassium carbonate was added and the mixture was extracted with dichloromethane. The organic extracts were dried (sodium sulphate), evaporated and purified by chromatography on silica eluting with dichloromethane—3M ammonia in methanol to give a pale yellow gum (167 mg). To a solution of this amine in isopropanol (3 ml) was added a solution of oxalic acid (23 mg) in hot methanol (0.3 ml). The crystals that formed on cooling were collected and dried to afford 180 mg (100%) of the title compound as a white solid.

MS APCI+ve$^m$/z 306 [(M+H)$^+$].

$^1$H NMR 400 MHz (d$_6$-DMSO) 8.66 (d, 1H), 8.56 (dd, 1H), 8.02 (d, 1H), 7.82 (dt, 1H), 7.52 (d, 1H), 7.46 (dd, 1H), 6.42 (s, 2H), 5.92 (dd, 1H), 2.89 (t, 2H), 2.37–2.27 (m, 1H), 2.21–2.10 (m, 1H).

EXAMPLE 59

4-Chloro-5-fluoro-2-[3-(methylamino)-1-(3-pyridinyl)propoxy]benzonitrile oxalate a) [(3-(5-Chloro-2-cyano-4-fluorophenoxy)-3-(3-pyridinyl)propyl]carbamic acid 1,1 dimethylethyl ester Sodium hydride (34.2 mg, 60% dispersion in oil, 0.86 mmol) was added to a solution of the product from Example 58 (c) (219 mg, 0.54 mmol) and methyl iodide (0.2 ml, 3.2 mmol) in tetrahydrofuran (4 ml) and stirred for 3 h. Aqueous ammonium chloride was added and the mixture was extracted with dichloromethane (three times). The combined organic extracts were dried (sodium sulphate), evaporated and purified by chromatography on silica eluting; with petrol—acetone to give the sub-title compound as a colourless oil (157 mg, 69%).

MS APCI+ve$^m$/z 420 [(M+H)$^+$].

b) 4-Chloro-5-fluoro-2-[3-(methylamino)-1-(3-pyridinyl)propoxy]benzonitrile oxalate The title compound was prepared from the product of Example 59 (a) by the method of Example 58 (d).

MS APCI+ve$^m$/z 320 [(M+H)$^+$].

$^1$H NMR 400 MHz (d$_6$-DMSO) 8.67 (d, 1H), 8.57 (d, 1H), 8.03 (d, 1H), 7.83 (d, 1H), 7.54 (d, 1H), 7.47 (dd, 1H), 5.88 (t, 1H, 3.11–2.95 (m, 2H), 2.59 (s, 3), 2.45–2.32 (m, 1H), 2.30–2.19(m, 1H).

EXAMPLE 60

γ-[2-Chloro-5-(trifluoromethyl)phenoxy]-3-pyridinepropanamine oxalate a) [(3-(2-Chloro-5-trifluoromethylphenoxy)-3-(3-pyridinyl)propyl]-carbamic acid 1,1-dimethylethyl ester Diethyl azodicarboxylate (0.71 ml, 4.47 mmol) was added to a solution of [3-hydroxy-3-(3-pyridinyl)propyl]carbamic acid 1,1-dimethylethyl ester (Example 58(b)) (291 mg, 1.15 mmol), 2-chloro-5-trifluoromethylphenol (232 mg, 1.18 mmol) and triphenylphosphine (455 mg, 1.73 mmol) in tetrahydrofuran (6 ml) at 0° C. and stirred at 20° C. for 18 h. The reaction was concentrated in vacuo and the residue purified by chromatography on silica, eluting with petrol—diethyl ether to afford the sub-title compound (394 mg, 79%).

MS APCI+ve$^m$/z 431 [(M+H)$^+$].

b) γ-[2-Chloro-5-(trifluoromethyl)phenoxy]-3-pyridinepropanamine oxalate

The title compound was prepared by the method of Example 58 (d) using the product of Example 60 (a).

MS APCI+ve$^m$/z 331 [(M+H)$^+$].

$^1$H NMR 300 MHz (d$_6$-DMSO) δ 8.64 (d, 1H), 8.54 (dd, 1H), 7.99 (s, 2H), 7.81 (dt, 1H), 7.69 (d, 1H), 7.44 (dd, 1H), 7.36–7.28 (m, 2H), 5.93 (dd, 1H), 3.02–2.91 (m, 2H), 2.42–2.12 (m, 2H).

EXAMPLE 61

2-[3-Amino-1-(6-methoxy-2-pyridinyl)propoxy]-4-chloro-5-fluorobenzonitrile oxalate a) [3-(6-Methoxy-2-pyridinyl)-3-oxopropyl]carbamic acid 1,1-dimethylethyl ester Butyl lithium (2.5M solution in hexanes, 1.4 ml) was added to a solution of 6-bromo-2-methoxypyridine (690 mg, 4.0 mmol) in tetrahydrofuran (4 ml) at −78° C. and stirred for 1 h. A solution of [3-(methoxymethylamino)-3-oxopropyl carbamic acid 1,1-dimethylethyl ester (344 mg, 1.42 mmol) in tetrahydrofuran (3 ml) was added and the mixture was warmed to 0° C. over 3 h. The mixture was quenched with saturated aqueous ammonium chloride and extracted with ethyl acetate (three times) The combined organic extracts were dried (sodium sulphate), evaporated and purified by chromatography on silica eluting with petrol-acetone to give the sub-title compound as a colourless oil (291 mg, 73%).

MS APCI+ve$^m$/z 281 [(M+H)$^+$].

b) 1[3-Hydroxy-3-(6-methoxy-2-pyridinyl)-propyl]carbamic acid 1,1-dimethylethyl ester A mixture of the product from Example 61 (a) (489 mg, 1.75 mmol) and sodium tetrahydroborate (133 mg, 3.52 mmol) in tetrahydrofuran (4 ml) was stirred for 5 h. 2M Hydrochloric acid was added and the mixture was extracted with ethyl acetate (three times). The combined organic extracts were dried (sodium sulphate), evaporated and purified by chromatography on silica eluting with petrol-ether to give the sub-title compound as a colourless oil (446 mg, 90%).

MS APCI+ve$^m$/z 283 [(M+H)$^+$].

c) [(3-(5-Chloro-2-cyano-4-fluorophenoxy)-3-(6-methoxy-2-pyridinyl)-propyl]-carbamic acid 1,1-dimethylethyl ester The sub-title compound was prepared by the method of Example 58 (c) using [3-hydroxy-3-(6-methoxy-2-pyridinyl)propyl]carbamic acid 1,1-dimethylethyl ester (Example 61 (b)) and 4-chloro-2,5-difluorobenzonitrile.

MS APCI+ve$^m$/z 436 [(M+H)$^+$].

d) 2-[3-Amino-1-(6-methoxy-2-pyridinyl)propoxyl-4-chloro-5-fluorobenzamide oxalate The title compound was prepared from the product of Example 61 (c) by the method of Example 58 (d).

MS APCI+ve$^m$/z 336 [(M+H)$^+$].

$^1$H NMR 300 MHz (d$_6$-DMSO) 8.05 (d, 1H), 7.76 (t, 1H), 7.48 (d, 1H), 7.04 (d, 1H), 6.80 (d, 1H), 5.71 (t, 1H), 3.85 (s, 3H), 3.04–2.95 (m, 2H), 2.39–2.25 (m, 2H).

EXAMPLE 62

2-[[(1R)-3-Amino-1-(5-methyl-3-isoxazolyl)propyl]oxy]-4-chloro-5-fluoro-benzonitrile fumarate 5-Methylisoxazole-3-carboxylic acid was converted into the title product by the procedures described for Example 89 steps (a) to (c) and Example 93 steps (a) to (c) to afford a solid.

MS APCI+ve$^m$/z 310 [(M+H)$^+$].

$^1$H NMR 300 MHz (d$_6$-DMSO) 8.04 (1H, d), 7.58 (1H, d), 6.40 (2H, s), 6.34 (1H, s), 5.99–5.91 (1H, m), 2.94 (2H, t), 2.40 (3H, s), 2.38–2.29 (1H, m), 2.26–2.15 (1H, m).

EXAMPLE 63

2-[3-Amino-1-(1,6-dihydro-6-oxo-2-pyridinyl)propoxy]-4-chloro-5-fluorobenzonitrile oxalate A solution of the product from Example 61(d) (313 mg, 0.932 mmol) in 62% aqueous hydrogen bromide (2 ml) was heated at 70° C. for 5.5 h. Aqueous potassium carbonate was added and the mixture was extracted with dichloromethane. The organic extracts were dried (sodium sulphate), evaporated and purified by chromatography on silica eluting with dichloromethane—7M ammonia in methanol and then methanol to give:

2-[3-amino-1-(6-methoxy-2-pyridinyl)propoxy]-4-chloro-5-fluorobenzamide, 33.8 mg. The oxalate salt was prepared by the method of Example 58 (d) to give a solid (31.7 mg). MS APCI+ve$^m$/z 354 [(M+H)$^+$]. $^1$H NMR 400 MHz (d$_6$-DMSO) 8.11–7.88 (m, 4H), 7.73 (ddd, 1H), 7.65 (d, 1H), 7.38 (d, 1H), 7.07 (d, 1H), 6.78 (d, 1H), 5.76–5.70 (m, 1H), 3.85 (s, 3H), 3.04–2.89 (m, 2H), 2.38–2.20 (m, 2H);

followed by 2-[3-amino-1-(1,6-dihydro-6-oxo-2-pyridinyl)propoxy]-4-chloro-5-fluorobenzonitrile, 9.5 mg, which was converted into the oxalate salt as in Example 58 (d) to give a solid (5.3 mg).

MS APCI+ve$^m$/z 322 [(M+H)$^+$].

$^1$H NMR 400 MHz (d$_6$-DMSO) 8.08 (d, 1H), 7.99–7.76 (m, 2H), 7.53 (t, 1H), 7.34 (d, 1H), 6.45 (d, 2H), 5.48 (s, 1H), 2.94 (s, 2H), 2.39–2.17 (m, 2H).

EXAMPLE 64

(R)-γ-[2-Chloro-5-(trifluoromethyl)phenoxy]-2-pyridinepropanamine dihydrochloride a) [3-Oxo-3-(2-pyridinyl)propyl]carbamic acid 1,1-dimethylethyl ester 2-Bromopyridine (3.16 g) in dry ether (50 ml) was cooled to −60° C. under a nitrogen atmosphere. N-Butyllithium (2.5M solution in hexanes, 8.5 ml) was added dropwise and stirring at −60° C. continued for a further 15 minutes. A solution of 1,1-dimethylethyl (methoxymethylamino)-3-oxopropyl]carbamate (2.32 g) in ether (20 ml) was added dropwise and the reaction stirred at −40° C. for 1 h and then at 0° C. for 0.5 h. The reaction was quenched with saturated ammonium chloride and extracted with ethyl acetate. The organic extract was washed with water, then brine, dried over magnesium sulphate and evaporated to an oil which was passed down a silica gel column eluted with hexane-:ethyl aceate (4:1) to afford the product as a pale yellow oil (1.4 g).

MS APCI+ve$^m$/z 251 [(M+H)$^+$].

$^1$H NMR 300 MHz (CDCl$_3$) 8.68 (1H, dt), 8.03 (1H, d), 7.84 (1H, td), 7.48 (1H, ddd), 5.10 (1H, s), 3.56 (2H, q), 3.43 (2H, t), 1.43 (9H, s).

b) [(3S)-3-Hydroxy-3-(2-pyridinyl)propyl]carbamic acid, 1,1-dimethylethyl ester

The product of step (a) (0.6 g) was reduced by the procedure described in Example 68(a) to afford the product as a clear oil (0.24 g).

¹H NMR 400 MHz (CDCl₃) 8.53 (1H, d), 7.70 (1H, dd), 7.36 (1H, d), 7.20 (1H, dd), 5.04 (1H, s), 4.82 (1H, dt), 4.65 (1H, s), 3.45 (1H, m), 3.33–3.17 (1H, m), 2.09 (1H, dd), 1.84–1.71 (1H, m), 1.44 (9H, s).

c) (R)-3-[2-Chloro-5-(trifluoromethyl)phenoxy]-3-(2-pyridinyl)propyl]carbamic acid, 1,1-dimethylethyl ester The product of step (b) (0.24 g) and 2-chloro-4-trifluoromethylphenol were subjected to the procedure described in Example 8(a) to afford the product as an oil (0.3 g).

MS APCI+ve $^m$/z 431 [(M+H)⁺].

¹H NMR 400 MHz (CDCl₃) 8.60 (1H, dd), 7.67 (1H, td), 7.47 (1H, d), 7.37 (1H, d), 7.22 (1H, ddd), 7.11 (1H, dd), 6.95 (1H, d), 5.44 (1H, dd), 5.15 (1H, s), 3.45 (1H, dq), 3.30 (1H, dt), 2.38–2.20 (2H, m), 1.40 (9H, s).

d) (R)-γ-[2-Chloro-5-(trifluoromethyl)phenoxy]-2-pyridinepropanamine dihydrochloride The product of step (c) (0.3 g) was subjected to the procedure described in Example 88(b) to afford the product as a white solid (0.25 g).

MS APCI+ve $^m$/z 331 [(M+H)⁺].

¹H NMR 400 MHz (d₆-DMSO) 8.63 (1H, dd), 8.11 (3H, s), 7.88 (1H, td), 7.71 (1H, d), 7.47 (1H, d), 7.40 (1H, ddd), 7.30 (1H, d), 7.24 (1H, d), 5.84 (1H, dd), 3.01 (2H, d), 2.43–2.23 (2H, m).

EXAMPLE 65

2-[3-Amino-1-(6-bromo-3-pyridinyl)propoxy]-4-chlorobenzonitrile oxalate a) [3-(6-Bromo-3-pyridinyl)-3-oxopropyl] carbamic acid, 1,1-dimethylethyl ester The sub-title compound was prepared from 2,5-dibromopyridine and [3-(methoxymethylamino)-3-oxopropyl carbamic acid, 1,1-dimethylethyl ester by the method of Example 58(a).

¹H NMR 300 MHz (CDCl₃) 8.90 (1H, d), 8.07 (1H, dd), 7.62 (1H, dd), 5.07 (1H, s), 3.53 (1H, q), 3.50 (1H, q), 3.19 (2H, t), 1.43 (9H, s).

b) [3-(6-Bromo-3-pyridinyl)-3-hydroxypropyl]carbamic acid 1,1-dimethylethyl ester A mixture of product from Example 65(a) (645 mg, 1.96 mmol) and sodium tetrahydroborate (115 mg, 3.04 mmol) in tetrahydrofuran (5 ml) was stirred for 18 h. 2M hydrochloric acid was added and the mixture was extracted with ethyl acetate (three times). The combined organic extracts were dried (magnesium sulphate), evaporated and purified by chromatography on silica eluting with diethyl ether to give the sub-title compound as a colourless oil (6.60 g).

¹H NMR 300 MHz (CDCl₃) 8.33 (1H, d), 7.63 (1H, dd), 7.46 (1H, d), 4.95–4.86 (1H, m), 4.78–4.69 (1H, m), 4.33–4.27 (1H, m), 3.68–3.51 (1H, m), 3.22–3.09 (1H, m), 1.89–1.66 (2H, m), 1.46 (9H, s).

c) [3-(6-Bromo-3-pyridinyl)-3-(5-chloro-2-cyanophenoxy) propyl]carbamic acid 1,1-dimethylethyl ester The sub-title compound was prepared from the product of Example 65(b) and 4-chloro-2-hydroxybenzonitrile by the method of Example 60(a).

¹H NMR 300 MHz (CDCl₃) 8.40 (1H, d), 7.65 (1H, dd), 7.55–7.41 (1H, m), 7.33 (1H, d), 7.06–6.93 (1H, m), 6.80 (1H, d), 5.38 (1H, dd), 4.84 (1H, s), 3.45–3.28 (2H, m), 2.36–2.03 (2H, m), 1.44 (9H, s).

d) 2-[3-Amino-1-(6-bromo-3-pyridinyl)propoxy]-4-chlorobenzonitrile oxalate

The title compound was prepared from the product of Example 65(c) by the method of Example 58(d).

MS APCI+ve $^m$/z 366 [(M+H)⁺].

¹H NMR 300 MHz (d₆-DMSO) 8.50 (s, 1H), 7.85–7.70 (m, 3H), 7.31 (s, 1H), 7.21 (dd, 1H, 5.96–5.88 (m, 1H), 2.94–2.86 (m, 2H), 2.39–2.07 (m, 2H).

EXAMPLE 66

2-[[3-Amino-1-(5-isoxazolyl)propyl]oxy]-4-chlorobenzonitrile oxalate a) N-Methoxy-N-methyl-5-isoxazolecarboxamide A solution of isoxazole 5-carboxylic acid (2.81 g), N-methoxy-N-methylamine hydrochloride (2.49 g), EDCI (4.96 g), dimethylaminopyridine (3.15 g) and 4-methylmorpholine (2.8 ml) in dichloromethane (20 ml) was stirred for 18 h. 2M Hydrochloric acid was added and the mixture was extracted with dichloromethane (three times). The organic layers were washed with aqueous sodium hydrogen carbonate and then brine, combined, dried (magnesium sulphate), evaporated and purified by chromatography on silica eluting with petrol-ether to give the sub-title compound as a colourless oil (2.94 g, 76%).

¹H NMR 300 MHz (CDCl₃) 8.35 (1H, d), 6.89 (1H, d), 3.83 (3H, s), 3.39 (3H, s).

b) 3-Chloro-1-(5-isoxazolyl)-1-propanone

Vinyl magnesium bromide (20 ml, 1M in tetrahydrofuran) was added to a solution of the product from Example 66(a) (2.59 g, 16.6 mmol) in tetrahydrofuran (35 ml) at −78° C. and warmed to 0° C. over 2.5 h. After cooling to −50° C., the mixture was slowly poured into excess iced 2M hydrochloric acid. The mixture was extracted with ether (five times). The organic extracts were dried (magnesium sulphate) and evaporated to give a brown oil. 1M Hydrogen chloride in diethyl ether (20 ml) was added and stirred for 40 minutes. The solvent was removed its vacuo to give the sub-title compound (2.0 g, 75%).

¹H NMR 300 MHz (CDCl₃) 8.39 (1H, s), 6.96 (1H, s), 3.91 (2H, t), 3.49 (2H, t).

c) α-(2-Chloroethyl)-5-isoxazolemethanol

Borane (4.2 ml, 1M in tetrahydrofuran) was added to a solution of (3αS)-tetrahydro-1-methyl-3,3-diphenyl-3H-pyrrolo [1,2-c][1,3,2]oxazaborole (0.06 ml, 1M in toluene) in tetrahydrofuran (5 ml) at 0° C. A solution of the product from Example 66(b) (998 mg, 6.25 mmol) in tetrahydrofuran (5 ml) was added slowly and then stirred at 20° C. for 4 h. Methanol was added and the solution was evaporated and the residue azeotroped with methanol. Purification by chromatography on silica eluting with petrol-ether gave the sub-title compound as a colourless oil (562 mg, 56%).

MS APCI+ve $^m$/z 162 [(M+H)⁺].

d) 4-Chloro-2-[3-chloro-1-(5-isoxazolyl)propoxy]-benzonitrile

Prepared by the method of Example 8(a) using α-(2-chloroethyl)-5-isoxazolemethanol and 4-chloro-2-hydroxybenzonitrile.

¹H NMR 300 MHz (CDCl₃) 8.26 (1H, d), 7.52 (1H, dd), 7.09 (1H, dt), 7.02 (1H, s), 6.36 (1H, t), 5.82–5.74 (1H, m), 3.95–3.84 (1H, m), 3.81–3.70 (1H, m), 2.75–2.61 (1H, m), 2.54–2.40 (1H, m).

e) 2-[[3-Amino-1-(5-isoxazolyl)propyl]oxy]-4-chlorobenzonitrile oxalate

A solution of the product from Example 66(d) (100 mg, 0.34 mmol) and sodium azide (34 mg,0.52 mmol) in DMSO (0.8 ml) was stirred for 3 days. Triphenylphosphine (88 mg, 0.34 mmol), tetrahydrofuran (2 ml) and water (0.5 ml) were added and the solution was stirred for 2 days. Purification by chromatography on silica eluting with dichloromethane—7M ammonia in methanol gave a pale yellow gum (27 mg). To a solution of this amine in isopropanol (3 ml) was added a solution of oxalic acid (9 mg) in methanol (0.3 ml). The crystals that formed on cooling were collected and dried to afford the title compound as a white solid (91 mg, 97%).

MS APCI+ve $^m$/z 278 [(M+H)⁺].

¹H NMR 300 MHz (d₆-DMSO) 8.61 (1H, d), 7.82 (1H, d), 7.51 (1H, d), 7.25 (1H, dd), 6.68 (1H, d), 6.15 (1H, t), 5.46 (3H, s), 2.88 (2H, t), 2.42–2.21 (2H, m).

EXAMPLE 67
4-Chloro-2-[3-[(2-hydroxyethyl)amino]-1-(5-isoxazolyl)propoxy]benzonitrile oxalate a) 4-Chloro-2-[3-iodo-1-(5-isoxazolyl)propoxy]benzonitrile A solution of the chloride from Example 66(d) (106 mg, 0.356 mmol) and sodium iodide (1 g) in acetone (10 ml) was stirred at 20° C. for 2 days and at 55° C. for 1 day. The solvent was removed in vacuo, water added and the mixture was extracted with dichloromethane (three times). The organic layers dried (sodium sulphate), evaporated to give the sub-title compound (159mg, 100%).

$^1$H NMR 300 MHz (CDCl$_3$) 8.26 (1H, d), 7.53 (1H, d), 7.08 (1H, dd), 7.03 (1H, s), 6.35 (1H, s), 5.66 (1H, dd), 3.53–3.30 (2H, m), 2.72–2.04 (2H, m).

b) 4-Chloro-2-[3-[(2-hydroxyethyl)amino]-1-(5-isoxazolyl)propoxy]benzonitrile oxalate A solution of 4-chloro-2-[3-iodo-1-(5-isoxazolyl)propoxy]benzonitrile (159 mg, 0.41 mmol) and ethanolamine (0.2 ml) in tetrahydrofuran (2 ml) was stirred for 2 days. Water was added and the mixture was extracted with dichloromethane The combined organic extracts were dried (sodium sulphate), evaporated and purified by chromatography on silica eluting with dichloromethane –7M ammonia in methanol to give an orange gum (40 mg). The oxalate salt was prepared as in Example 58(d) to afford the title compound as a white solid (40 mg, 30%).

MS APCI+ve$^m$/z 322 [(M+H)$^+$].

$^1$H NMR 400 MHz (d$_6$-DMSO) 8.63 (d, 1H), 7.83 (d, 1H), 7.52 (d, 1H), 7.27 (dd, 1H), 6.69 (d, 1H), 6.17 (t, 1H), 3.94 (s, 2H), 3.65 (t, 4H), 3.10 (t, 1H), 3.04 (t, 1H), 2.48–2.43 (m, 2H).

EXAMPLE 68
(R)-γ-(2,5-Dichlorophenoxy)-5-isoxazolepropanamine oxalate a) (S)-α-(2-Chloroethyl)-5-isoxazolemethanol Borane (18 ml, 1M in tetrahydrofuran) was added to a solution of (3aR)-tetrahydro-1-methyl-3,3-diphenyl-3H-pyrrolo[1,2-c][1,3,2]oxazaborole (1.3 ml, 1M in toluene) in tetrahydrofuran (10 ml) at –10° C. A solution of 3-chloro-1-(3-isoxazolyl)-1-propanone (Example 66(b)) (6 g, 37.6 mmol) in tetrahydrofuran (12 ml) was added slowly and then stirred at –10° C. to 20° C. for 18 h. Methanol was added and the solution was evaporated and the residue azeotroped with methanol. Purification by chromatography on silica eluting with petrol-ether gave the sub-title compound as a colourless oil (774 mg, 13%).

MS APCI+ve$^m$/z 162 [(M+H)$^+$].

b) (S)-α-(2-Azidoethyl)-5-isoxazolemethanol

A solution of the product from Example 68(a) (767 mg, 4.76 mmol) and sodium azide (342 mg, 5.26 mmol ) in DMSO (8 ml) was heated at 65° C. for 18 h. Water was added and the mixture was extracted with ethyl acetate (three times). The combined organic extracts were dried (magnesium sulphate), evaporated and purified by chromatography on silica eluting with petrol—diethyl ether to give the sub-title compound as a colourless oil (454 mg, 57%).

$^1$H NMR 300 MHz (CDCl$_3$) 8.22 (1H, d), 6.26 (1H, t), 5.12–5.03 (1H, m), 3.65–3.46 (2H, m), 2.54 (1H, d), 2.18–2.05 (2H, m).

c) (R)-γ-(2.5-Dichlorophenoxy)-5-isoxazolepropanamine oxalate

Diethyl azodicarboxylate (0.23 ml, 1.46 mmol) was added to a solution of triphenylphosphine (355 mg, 1.35 mmol) in tetrahydrofuran (3 ml) at 0° C. After 10 minutes a solution of the product from Example 68(b) (151 mg, 0.90 mmol) and 2,5-dichlorophenol (164 mg, 1.0 mmol) in tetrahydrofuran (3 ml) were added and stirred at 20° C. for 3 h. Triphenylphosphine (268 mg, 1.02 mmol) and water (1 ml) were added and stirred for 2.5 days. The reaction was concentrated in vacuo and the residue purified by chromatography on silica, eluting with dichloromethane –7M ammonia in methanol to give a pale yellow gum (91 mg). To a solution of this amine in isopropanol (3 ml) was added a solution of oxalic acid (26 mg) in methanol (1 ml). The crystals that formed on cooling were collected and dried to afford the title compound as a white solid (37 mg, 14%).

MS APCI+ve$^m$/z 287 [(M+H)$^+$].

$^1$H NMR 300 MHz (d$_6$-DMSO) 8.61 (1H, d), 7.50 (1H, d), 7.34 (1H, d), 7.11 (1H, d of d), 6.62 (1H, d), 6.02 (1H, d), 2.98 (2H, t), 2.44–2.24 (2H, m).

EXAMPLE 69
(R)-γ-(2,5-Dichlorophenoxy)-N-methyl-benzenepropanamine fumarate

Using [(3S)-3-hydroxy-3-phenylpropyl]methylcarbamic acid 1,1-dimethylethyl ester (266 mg, 1.0 mmol) and 9,5-dichlorophenol (163 mg, 1.0 mmol), the title compound was prepared using the procedure described in Example 2(b), with a final conversion into a fumarate salt.

MS APCI+ve$^m$/z 310 [(M+H)$^+$].

$^1$H NMR 300 MHz (d$_6$-DMSO) 7.45–7.28 (6H, m), 7.08 (1H, d), 6.98–6.95 (1H, dd), 6.45 (2H, s), 5.75–5.71 (1H, m), 2.95–2.90 (2H, t), 2.50 (3H, s), 2.34–2.08 (2H, m).

EXAMPLE 70
(R)-γ-[2-Chloro-5-(trifluoromethyl)phenoxy]-N-methyl-benzenepropanamine fumarate Using 1,1-dimethylethylester [(3S)-3-hydroxy-3-phenylpropyl]methylcarbamic acid (281 mg, 1.06 mmol) and 4-chloro-3-hydroxybenzotrifluoride (208 mg, 1.06 mmol), the title compound was prepared using the procedure described in Example 2(b), with a final conversion into a fumarate salt.

MS APCI+ve$^m$/z 344 [(M+H)$^+$].

$^1$H NMR 300 MHz (d$_6$-DMSO) 7.67–7.64 (1H,dd), 7.44–7.23 (7H,m), 6.44 (2H,s), 5.86–5.82 (1H,m), 2.94 (2H,t), 2.50 (3H,s), 2.38–2.12 (2H,m).

EXAMPLE 71
4-Chloro-2-[[(1R)-3-(methylamino)-1-(2-thienyl)propyl]oxy]benzonitrile oxalate a) 4-Chloro-2-[[(1R)-3-chloro-1-(2-thienyl)propyl]oxy]benzonitrile Using 4-chloro-2-hydroxybenzonitrile (303 mg, 1.97 mmol) and (S)-α-(2-chloroethyl) thiophenemethanol (349 mg, 1.97 mmol), and the procedure described in Example 5(a), the title compound was prepared as a white crystalline solid (373 mg, 61%).

$^1$H NMR300 MHz (CDCl$_3$) 7.48–7.45 (1H,d), 7.33–7.31 (1H,dd), 7.14–7.13 (1H,m), 7.03–6.97 (3H,m), 5.82–5.77 (1H,q), 3.91–3.83 (1H,m), 3.67–3.59 (1H,m), 2.70–2.63 (1H,m), 2.42–2.33 (1H,m).

b) 4-Chloro-2-[[(1R)-3-iodo-1-(2-thienyl)propyl]oxy]benzonitrile

The product of step (a) (368 mg, 1.18 mmol) was converted into the title compound using the procedure described in Example 5(b), giving a pale brown oil (408 mg, 86%).

The product was used directly in the next step.

c) 4-Chloro-2-[[(1R)-3-(methylamino)-1-(2-thienyl)propyl]oxy]benzonitrile oxalate The product of step (b) (400 mg, 0.99 mmol) was used to prepare the title compound by the procedure described in Example 5(c) except that the oxalate salt was prepared (135 mg, 34%).

MS APCI+ve $^m$/z 307 [(M+H)$^+$].

$^1$H NMR 400 MHz (d$_6$-DMSO) 7.79–7.77 (1H,d), 7.58–7.56 (1H,d), 7.47–7.46 (1H, 7.27–7.26 (1H,m), 7.20–7.18 (1H,dd), 7.05–7.03 (1H,m), 6.17–6.14 (1H,t), 3.09–2.94 (2H,m), 2.59 (3H,s), 2.50–2.39 (1H,m), 2.33–2.22 (1H,m).

EXAMPLE 72

2-[[(1R)-3-Amino-1-(3-furanyl)propyl]oxy]-4-chloro-5-fluorobenzonitrile fumarate a) [3-(3-Furanyl)-3-oxopropyl]-carbamic acid 1,1-dimethylethyl ester 3-Bromofuran (5.88 g, 40 mmol) was dissolved in anhydrous tetrahydrofuran (60 ml) and the solution cooled to −78° C. n-Butyllithium (2.29M, 17.5 ml, 40 mmol) was added dropwise and the solution stirred for 1 h at −78° C. [3-(Methoxymethylamino)-3-oxopropyl]carbamic acid, 1,1-dimethylethyl ester as a solution in tetrahydrofuran (40 ml) was added dropwise over 1 h. The solution was stirred overnight whilst allowing to warm to room temperature. Aqueous saturated ammonium chloride solution (30 ml) was added and the mixture extracted with ethyl acetate (3×70 ml). The combined organic extracts were washed with water (3×30 ml), dried (sodium sulphate) and evaporated in vacuo. The residue was chromatographed on flash silica, eluting with hexane:ethyl acetate (7:3), to afford the title compound as a pale yellow solid (3.03 g, 63%).

$^1$H NMR 300 MHz CDCl$_3$ 8.05 (1H, d), 7.40–7.50 (1H, m), 6.72–6.82 (1H, m), 5.07 (1H, s), 3.41–3.60 (2H, m), 2.90–3.09 (2H, m), 1.43 (9H, s).

b) [(3R)-3-(3-Furanyl)-3-hydroxypropyl]carbamic acid 1,1-dimethylethyl ester (S)-2-Methyl-CBS-oxazaborolidine (1M in toluene, 0.84 ml, 0.836 mmol) was added to anhydrous tetrahydrofuran (50 ml) and the solution cooled to 0° C. Borane:tetrahydrofuran complex (1M, 5.02 ml, 5.02 mmol) was then added dropwise, keeping the temperature at 0° C. The mixture was stirred for 15 minutes then added the product of step (a) (2.0 g, 8.36 mmol) as a solution in tetrahydrofuran (50 ml), dropwise over 1 h keeping the temperature at 0° C. Stirred overnight whilst allowing to warm to room temperature. The reaction was quenched with methanol (5 ml) and stirred for a half hour. The solvent was removed in vacuo and another aliquot of methanol (20 ml) added. The solvent was removed in vacuo and the residue chromatographed on flash silica, eluting with hexane:ethyl acetate (1:1), to give the title compound as a colourless oil (1.685 g, 84%).

$^1$H NMR 300 MHz (CDCl$_3$) 7.35–7.43 (2H, m), 6.40 (1H, t), 4.85 (1H, s), 4.69–4.77 (1H, m), 3.41–3.60 (1H, m), 3.09–3.30 (2H, m), 1.80–1.92 (2H, m), 1.51 (9H, s).

c) [(3R)-3-(5-Chloro-2-cyano-4-fluorophenoxy)-3-(3-furanyl)propyl]-carbamic acid 1,1-dimethylethyl ester The product of step (b) (277 mg, 1.15 mmol) and 4-chloro-2,5-difluorobenzonitrile (199 mg, 1.15 mmol) were dissolved in dimethylformamide (10 ml) and sodium hydride (60%, 48 mg, 1.2 mmol) added in one portion. The reaction was stirred for 2 h at room temperature then quenched with aqueous saturated ammonium chloride solution (30 ml) and extracted with ethyl acetate (3×60 ml). The combined organic extracts were washed with water (3×20 ml), dried (sodium sulphate) and evaporated iii vacuo. The residue was chromatographed on flash silica, eluting with hexane:ethyl acetate (3:1), to give the title compound as a white crystalline solid (330 mg, 73%).

$^1$H NMR 300 MHz (CDCl$_3$) 7.39–7.51 (2H, m), 7.36 (1H, s), 7.05 (1H, d), 6.43 (1H, t), 5.27–5.36 (1H, m), 5.19 (1H,s), 3.18–3.43 (2H, m), 2.20–2.33 (1H, m), 2.02–2.13 (1H, m), 1.49 (9H, s).

d) 2-[[(1R)-3-Amino-1-(3-furanyl)propyl]oxy]-4-chloro-5-fluorobenzonitrile fumarate The product from step (c) (150 mg, 0.3 mmol) was dissolved in 4M HCl in dioxan (10 ml) and stirred at room temperature for 10 minutes. The reaction was placed in an ice-bath and aqueous saturated sodium bicarbonate solution (30 ml) added cautiously. The mixture wa extracted with ethyl acetate (3×50 ml) and the combined extracts were washed with water (20 ml), dried (sodium sulphate) and evaporated in vacuo. The residue was chromatographed on flash silica, eluting with 5% 7N ammonia in methanol in dichloromethane. The product was dissolved in methanol (5 ml) and treated with one equivalent of fumaric acid. Stirred for 10 minutes then removed the solvent in vacuo and triturated the solid residue with a little ethyl acetate. The white solid was filtered off and dried to give the title compound (50 mg, 40%).

MS APCI+ve $^m$/z 295/297 [(M+H)$^+$].

$^1$H NMR 300 MHz (d$_6$-DMSO) 8.05 (1H, d), 7.87 (1H, s), 7.75 (1H, d), 7.65 (1H, d), 6.65 (1H, s), 6.51 (2H, s), 5.77–5.89 (1H, m), 2.95 (2H, t), 2.10–2.44 (2H, m),

EXAMPLE 73

4-Chloro-5-fluoro-2-[[(1R)-1-(3-furanyl)-3-methylamino)propyl]oxy]-benzonitrile fumarate a) [(3R)-3-(5-Chloro-2-cyano-4-fluorophenoxy)-3-(3-furanyl)propyl]carbamic acid 1,1-dimethylethyl ester The product from Example 72(c) (460 mg, 1.17 mmol) was dissolved in anhydrous tetrahydrofuran (10 ml) and sodium hydride (60%, 104 mg, 2.6 mmol) added in one portion. The reaction was stirred for 10 minutes, then methyl iodide (0.66 ml, 10.53 mmol) was added and the reaction stirred for 24 h at room temperature. The reaction was quenched with aqueous saturated ammonium chloride solution (30 ml) and the mixture extracted with ethyl acetate (3×70 ml). The combined extracts were washed with water (3×30 ml), dried (sodium sulphate) and evaporated in vacuo to give the title compound (360 mg, 75%).

$^1$H NMR 300 MHz (CDCl$_3$) 7.42 (2H, d), 7.26–7.36 (1H, m), 6.99 (1H, d), 6.42 (1H, s), 5.16–5.26 (1H, m), 3.27–3.56 (2H, m), 2.87 (3H, s), 2.21–2.43 (1H, m), 2.02–2.20 (1H, m), 1.40 (9H, s).

b) 4-Chloro-5-fluoro-2-[[(1R)-1-(3-furanyl)-3-methylamino)propyl]oxy]-benzonitrile fumarate Using the product from step (a) (355 mg, 0.87 mmol) and the procedure described in Example 72(d), the title compound was prepared as a white solid (210 mg, 78%).

MS APCI+ve $^m$/z 309/311 [(M+H)$^+$].

$^1$H NMR 300 MHz (d$_6$-DMSO) 7.98 (1H, d), 7.80 (1H, s), 7.68 (1H, t), 7.61 (1H, d), 6.53 (1H, t), 6.44 (2H, s), 5.76 (1H, t), 2.90 (2H, t), 2.57 (3H, s), 2.33 (1H, quintet), 2.17 (1H, m).

EXAMPLE 74

4-Chloro-5-fluoro-2-[[(1R)-3-(methylamino)-1-(3-thienyl)propyl]oxy]benzonitrile oxalate a) N-Methoxy-N-methyl-3-thiophene carboxamide 3-Thiophene carboxylic acid (10.04 g, 78.3 mmol) was dissolved in dichloromethane (250 ml) and 4-dimethylaminopyridine (9.57 g, 78.3 mmol), N,O-dimethylhydroxylamine hydrochloride (7.64 g, 78.3 mmol), N-methylmorpholine (8.6 ml, 78.3 mmol) and 1-(3-dimethylaminopropyl)-3-ethylcarbodiimide hydrochloride (15.01 g, 78.3 mmol) added and the resultant solution stirred for 24 h at room temperature. The reaction was diluted with dichloromethane (100 ml) and washed with aqueous 2M hydrochloric acid (3×30 ml), aqueous saturated sodium bicarbonate solution (2×30 ml) and water (3×30 ml). The organic phase was dried (magnesium sulphate), filtered and evaporated to give the title compound as a colourless oil (12.3 g, 92%).

$^1$H NMR 300 MHz (CDCl$_3$) 8.07 (1H, dd), 7.58 (1H, dd), 7.26–7.33 (1H, m), 3.66 (3H, s), 3.37 (3H, s).

b) 1-(3-Thienyl)-2-propen-1-one

The product from step (a) (2.074 g, 12.1 mmol) was dissolved in anhydrous tetrahydrofuran (30 ml) and the solution cooled to −10° C. Vinyl magnesium bromide (1M, 14.5 ml, 14.5 mmol) was added dropwise, keeping the temperature below 0° C. The resultant solution was stirred at 0° C. for 2.5 h, then allowed to warm to room temperature. The reaction mixture was slowly poured into aqueous 2M hydrochloric acid (200 ml) and ice. Extracted with ethyl acetate (3×70 ml) and the combined extracts were washed with water (2×30 ml) and brine (20 ml), dried (magnesium sulphate) and evaporated in vacuo to give the title compound (1.288 g, 77%).

$^1$H NMR 300 MHz (CDCl$_3$) 8.06–8.12 (1H, m), 7.58–7.64 (1H, m), 7.32–7.39 (1H, m), 6.99–7.12 (1H, m), 6.46 (1H, dd), 5.89 (1H, dd).

c) 3-Chloro-1-(3-thienyl)-1-propanone

The product from step (b) (1.288 g, 9.3 mmol) was dissolved in a mixture of diethyl ether (30 ml) and dichloromethane (20 ml) and 1M hydrochloric acid in diethyl ether (25 ml) added. The reaction was stirred for 18 h at room temperature. The solvent was removed in vacuo to give the title compound (1.482 g, 91%).

$^1$H NMR 300 MHz (CDCl$_3$) 8.02–8.12 (1H, m), 7.51–7.61 (1H, m), 7.30–7.40 (1H, m), 3.90 (2H, t), 3.37 (2H, t).

d) (R)-α-(2-Chloroethyl)-3-thiophenemethanol

Using the procedure described in Example 72(b) and 3-chloro-1-(3-thienyl-1-propanone (984 mg, 5.6 mmol), the title compound was prepared as a colourless oil (647 mg, 65%).

$^1$H NMR 300 MHz (CDCl$_3$) 7.29–7.36 (1H, m), 7.20–7.27 (1H, m), 7.04–7.12 (1H, m), 5.02–5.09 (1H, m), 3.70–3.82 (1H, m), 3.52–3.62 (1H, m), 2.08–2.34 (2H, m), 1.95 (1H, d).

e) 4-Chloro-2-[[(1R)-3-chloro-1-(3-thienyl)-propyl]oxy]-5-fluoro-benzonitrile

Using the product of step (d) (322 mg, 1.84 mmol), 4-chloro-2,5-difluorobenzonitrile (320 mg, 1.84 mmol) and the procedure described in Example 72(c), the title compound was prepared (540 mg, 89%).

$^1$H NMR 300 MHz (CDCl$_3$) 7.35–7.40 (1H, m), 7.29–7.34 (1H, m), 7.25–7.28 (1H, m), 7.11 (1H, dt), 6.95–6.99 (1H, m), 5.54–5.63 (1H, m), 3.78–3.90 (1H, m), 3.55–3.66 (1H, m), 2.53–2.65 (1H, m), 2.21–2.35 (1H, m).

f) 4-Chloro-5-fluoro-2-[[(1R)-3-iodo-1-(3-thienyl)-propyl]oxy]benzonitrile

Using the procedure described in Example 5(b) and 4-chloro-2-[[(1R)-3-chloro-1-(3-thienyl)propyl]oxy]-5-fluorobenzonitrile (520 mg, 1.57 mmol), the title compound was prepared (640 mg, 97%).

$^1$H NMR 300 MHz (CDCl$_3$) 7.35–7.39 (1H, m), 7.29–7.34 (2H, m), 7.09–7.12 (1H, m), 6.95–6.99 (1H, m), 5.42–5.51 (1H, m), 3.37–3.47 (1H, m), 3.16–3.26 (1H, m), 2.51–2.61 (1H, m), 2.26–2.38 (1H, m).

g) 4-Chloro-5-fluoro-2-[[(1R)-3-(methylamino)-1-(3-thienyl)propyl]oxy]benzonitrile oxalate Using the product of step (f) (210 mg, 0.5 mmol) and the procedure described in Example 5(c), with oxalic acid replacing hydrochloric acid, the title compound was prepared (148mg, 71%).

MS APCI+ve$^m$/z 325/327 [(M+H)$^+$].

$^1$H NMR 300 MHz (d$_6$-DMSO) 8.01 (1H, d), 7.58–7.64 (2H, m), 7.51 (1H, d), 7.12–7.16 (1H, m), 5.80–5.90 (1H, m), 2.90–3.08 (2H, m), 2.63 (3H, s), 2.30–2.43 (1H, m), 2.13–2.28 (1H, m).

EXAMPLE 75

4-Chloro-5-fluoro-2-[[(1R)-3-[(2-hydroxyethyl)amino]-1-(3-thienyl)propyl]oxy]benzonitrile oxalate The product from Example 74(f) (200 mg, 0.47 mmol) was dissolved in anhydrous tetrahydrofuran (40 ml), ethanolamine (5 ml) added and the mixture stirred for 3 days at room temperature. Water (30 ml) was added and the reaction extracted with ethyl acetate (3×60 ml). The combined organic extracts were washed with water (3×20 ml), dried (magnesium sulphate) and evaporated in vacuo. The residue was chromatographed on flash silica, eluting with 10% 7N ammonia in methanol in dichloromethane, and the product dissolved in methanol and treated with one equivalent of oxalic acid. The mixture was stirred for 10 minutes then the solvent removed in vacuo and the residue triturated in ethyl acetate. The white solid was filtered and dried to afford the title compound.

MS APCI+ve$^m$/z 355/357 [(M+H)$^+$].

$^1$H NMR 300 MHz (d$_6$-DMSO) 8.01 (1H, d), 7.61 (2H, t), 7.52 (1H, d), 7.08–7.17 (1H, m), 5.79–5.93 (1H, m), 3.64 (2H, t), 3.03 (4H, dd), 2.32–2.47 (1H, m), 2.18–2.32 (1H, m).

EXAMPLE 76

2-[[(1R)-3-[(2-aminoethyl)amino]-1-(3-thienyl)propyl]oxy]-4-chloro-5-fluoro-benzonitrile oxalate The product from Example 74(f) (200 mg, 0.47 mmol) was dissolved in anhydrous tetrahydrofuran (40 ml), ethylene diamine (5 ml) added and the mixture stirred for 3 days at room temperature. Water (30 ml) was added and the reaction extracted with ethyl acetate (3×60 ml). The combined organic extracts were washed with water (3×20 ml), dried (magnesium sulphate) and evaporated in vacuo. The residue was chromatographed on flash silica, eluting, with 10% 7N ammonia in methanol in dichloromethane, and the product dissolved in methanol and treated with one equivalent of oxalic acid. The mixture was stirred for 10 minutes then the solvent removed in vacuo and the residue triturated in ethyl acetate. The white solid was filtered off and dried to afford the title compound.

MS APCI+ve$^m$/z 354/356 [(M+H)$^+$].

$^1$H NMR 300 MHz (d$_6$-DMSO) 8.00 (1H, d), 7.56–7.68 (2H, m), 7.52 (1H, d), 7.15 (1H, dd), 5.72–6.01 (1H, m), 3.01–3.14 (4H, m), 2.91–3.01 (2H, m), 2.25–2.42 (1H, m), 2.12 –2.24 (1H, m).

EXAMPLE 77

2-[[(1R)-3-Amino-1-(3-thienyl)propyl]oxy]-4-chloro-5-fluorobenzonitrile oxalate a) 2-[[(1R)-3-Azido-1-(3-thienyl)propyl]oxy]-4-chloro-5-fluorobenzonitrile The product of Example 74(e) (540 mg, 1.64 mmol) was dissolved in anhydrous dimethyl sulfoxide (20 ml) and sodium azide (170 mg, 2.62 mmol) added. The reaction was heated to 65° C. and stirred for 12 h, cooled and water (60 ml) added. The mixture was extracted with ethyl acetate (3×70 ml) and the combined extracts washed with water (5×50 ml), dried (magnesium sulphate) and evaporated in vacuo to give the title compound (535 mg, 97%).

$^1$H NMR 300 MHz (CDCl$_3$) 7.35–7.41 (1H, m), 7.27–7.34 (2H, m), 7.07–7.11 (1H, m), 6.91–6.95 (1H, m), 5.38–5.47 (1H, m), 3.58–3.70 (1H, m), 3.39–3.51 (1H, m), 2.28–2.45 (1H, m), 2.02–2.20 (1H, m).

b) 2-[[(1R)-3-Amino-1-(3-thienyl)propyl]oxy]-4-chloro-5-fluorobenzonitrile oxalate The product from step (a) (529 mg, 1.57 mmol) was dissolved in anhydrous tetrahydrofuran (80 ml), triphenylphosphine (1.235 g, 4.71 mmol) added and the reaction mixture stirred for 1 h at room temperature. Water (5 ml) was added and the reaction stirred for 64 h. Water (100 ml) was added and the reaction extracted with ethyl acetate (4×70 ml). The combined organic extracts were washed with water (3×25 ml), dried (sodium sulphate) and evaporated in vacuo. The residue was chromatographed on flash silica, eluting with 5% 7N ammonia in methanol in dichloromethane, and the product dissolved in methanol and treated with one equivalent of oxalic acid. The mixture was stirred for 10 minutes then the solvent removed in vacuo and the solid residue triturated with ethyl acetate. The white solid was filtered off and dried to give the title compound (380 mg, 60%).

MS APCI+ve$^m$/z 311/313 [(M+H)$^+$].

$^1$H NMR 300 MHz (d$_6$-DMSO) 8.01 (1H, d), 7.55–7.67 (2H, m), 7.47 (1H, d), 7.13 (1H, dd), 5.85 (1H, dd), 2.81–2.99 (2H, m), 2.25–2.39 (1H, m).

EXAMPLE 78

4-Chloro-2-[3-(methylamino)-1-(2-thiazolyl)propoxy]-benzonitrile oxalate a) [3-Hydroxy-3-(2-thiazolyl)propyl]methylcarbamic acid 1,1-dimethylethyl ester 2-Bromothiazole (482 mg, 2.94 mmol) was dissolved in anhydrous tetrahydrofuran (15 ml) and the solution cooled to −78° C. n-Butyllithium (2.4M, 1.25 ml, 3.0 mmol) was added dropwise and the reaction stirred for a half hour at −70° C. This solution was then added dropwise to a solution of 1,1-dimethylethylester methyl(3-oxopropyl)-carbamic acid (600 mg, 3.2 mmol) in anhydrous tetrahydrofuran (15 ml) at −78° C. After the addition was complete, the reaction was allowed to warm slowly to room temperature overnight. Aqueous saturated ammonium chloride solution (20 ml) was added and the reaction extracted with ethyl acetate (3×70 ml). The combined extracts were washed with water (20 ml), dried (magnesium sulphate) and evaporated in vacuo. The residue was chromatographed on flash silica, eluting with ethyl acetate, to give the title compound as a pale orange oil (320 mg, 40%).

$^1$H NMR 300 MHz (CDCl$_3$) 7.72 (1H, d), 7.28 (1H, d), 5.32–5.44 (1H, bs), 4.85–4.94 (1H, m), 3.88–4.01 (1H, m), 2.99–3.12 (1H, m), 2.90 (3H, s), 2.80–2.89 (1H, m), 2.26–2.41 (1H, m), 1.77–1.91 (1H, m), 1.50 (9H, s).

b) [3-(5-Chloro-2-cyanophenoxy)-3-(2-thiazolyl)propyl]methylcarbamic acid 1,1-dimethylethyl ester The product from step (a) (312 mg, 1.15 mmol), 2-hydroxy-4-chlorobenzonitrile (176 mg, 1.15 mmol) and triphenylphosphine (330 mg, 1.26 mmol) were dissolved in anhydrous tetrahydrofuran (20 ml) and the solution cooled to 0° C. Diethyl azodicarboxylate (219 mg, 1.26 mmol) was added dropwise and the solution allowed to warm to room temperature slowly and stirred for 18 h. The solvent was removed in vacuo and the residue chromatographed on flash silica, eluting with hexane:ethyl acetate (1:1) to give the title compound (200 mg, 43%).

$^1$H NMR 300 MHz (CDCl$_3$) 7.79 (1H, d), 7.34–7.53 (2H, m), 6.92–7.09 (2H, m), 5.61 –5.71 (1H, m), 3.52–3.74 (1H, m), 3.31–3.45 (1H, m), 2.91 (3H, s), 2.82–2.92 (1H, m), 2.24–2.48 (1H, m), 1.40 (9H, s).

c) 4-Chloro-2-[3-(methylamino)-1-(2-thiazolyl)propoxy]benzonitrile oxalate

The product from step (b) (200 mg, 0.49 mmol) was dissolved in 4M hydrochloric acid in dioxan and stirred for 2.5 h. The solvent was removed in vacuo and the residue applied to an acidic SCX resin, washed with methanol (150 ml) and liberated the product with 7N ammonia in methanol (50 ml). The solvent was evaporated in vacuo and the residue dissolved in methanol (5 ml) and treated with one equivalent of oxalic acid. Stirred for 15 minutes then removed the solvent in vacuo and triturated the residue with a little ethyl acetate. The white solid was filtered off and dried to give the, title compound (17 mg, 11%).

MS APCI+ve$^m$/z 308/310 [(M+H)$^+$].

$^1$H NMR 300 MHz (d$_6$-DMSO) 7.79–7.93 (3H, m), 7.51 (1H, d), 7.26 (1H, dd), 6.20–6.29 (1H, m), 3.07 (2H, t), 2.59 (3H, s), 2.39–2.62 (2H, m).

EXAMPLE 79

2-[[1R)-3-Amino-1-(2-thiazolyl)propyl]oxy]-4-chloro-5-fluoro-benzonitrile hydrochloride a) [3-Oxo-3-[5-(trimethylsilyl)-2-thiazolyl]propyl]carbamic acid 1,1-dimethylethyl ester Using 2-(trimethylsilyl)thiazole (2.59 g, 16.5 mmol) and the procedure described in Example 72(a), with the modification of stirring for 2 h at −70° C. after the additions are complete and quenching at −65° C., the title compound was prepared (1.48 g, 55%).

$^1$H NMR 300 MHz (CDCl$_3$) 7.60 (1H, s), 4.76 (1H, s), 3.21 (2H, q), 2.91–3.08 (2H, m) 1.12 (9H, s), 0.01 (9H, s).

b) [(3R)-3-hydroxy-3-[5-(trimethylsilyl)-2-thiazolyl]propyl]carbamic acid 1,1-dimethylethyl ester The product from step (a) (1.47 g, 4.47 mmol) and the procedure described in Example 72(b) were used to prepare the title compound (700 mg, 47%).

$^1$H NMR 300 MHz (CDCl$_3$) 7.42 (1H, s), 4.68–4.79 (1H, m), 4.64 (1H, s), 4.28 (1H, s), 3.18–3.37 (1H, m), 2.79–2.95 (1H, m), 1.77–1.92 (1H, m), 1.51–1.65 (1H, m), 1.14 (9H, s), 0.03 (9H, s).

c) [(3R)-3-(5-Chloro-2-cyano-4-fluorophenoxy)-3-(2-thiazolyl)propyl]carbamic acid, 1,1-dimethylethyl ester The product from step (b) and the procedure described in Example 72(c) were used to prepare the title compound (376 mg, 43%).

$^1$H NMR 300 MHz (CDCl$_3$) 7.79 (1H, d), 7.31–7.42 (2H, m), 7.14 (1H, d), 5.66 (1H, dd), 4.79 (1H, s), 3.44–3.60 (1H, m), 3.22–3.33 (1H, m), 2.36–2.51 (1H, m), 2.20–2.34 (1H, m), 1.43 (9H, s).

d) 2-[[(1R)-3-Amino-1-(2-thiazolyl)propyl]oxy]-4-chloro-5-fluoro-benzonitrile hydrochloride The product from step (c) (370 mg, 0.9 mmol) was dissolved in 4M hydrochloric acid in dioxan and stirred at room temperature for a half hour. The solvent was removed in vacuo and the residue triturated with a mixture of ethyl acetate and methanol (14:1). The white solid was filtered and dried to afford the title compound (243 mg, 70%).

MS APCI+ve$^m$/z 312/314 [(M+H)$^+$].

$^1$H NMR 300MHz (d$_6$-DMSO) 8.23 (3H, br s), 8.08 (1H, d), 7.9 (1H, d), 7.85(1H, d), 7.74 (1H, d), 6.29 (1H, dd), 2.90–3.07 (2H, m), 2.35–2.48 (2H, m).

EXAMPLE 80
γ-(2-Chloro-5-nitrophenoxy)-N-methylbenzenepropanamine hydrochloride a) [3-(2-Chloro-5-nitrophenoxy)-3-phenylpropyl]methylcarbamic acid 1,1-dimethylethyl ester This was prepared by the method of Example 2 using α-[2-(methylamino)ethyl]benzenemethanol and 2-chloro-5-nitrophenol.

MS APCI+ve $^m$/z 321/323 [(M-Boc+H)$^+$].

b) γ-(2-Chloro-5-nitrophenoxy)-N-methylbenzenepropanamine hydrochloride

[3-(2-Chloro-5-nitrophenoxy)-3-phenylpropyl]methylcarbamic acid, 1,1-dimethylethyl ester (132 mg, 0.282 mmol) was stirred in 4N HCl in dioxane (1 ml) for 16 h, and the resulting solid filtered off to give the product as the hydrochloride salt (60 mg).

MS APCI+ve $^m$/z 321/323 [(M+H)$^+$].

$^1$H NMR 300 MHz (d$_6$-DMSO) 8.89–8.73 (2H, br m), 7.83–7.73 (3H, m), 7.47–7.39 (4H, m), 7.36–7.30 (1H, m), 5.92 (1H, m), 3.11–3.00 (2H, m), 2.58 (3H, s), 2.42–2.31 (1H, m), 2.28–2.18 (1H, m).

EXAMPLE 81
(R)-γ-(5-Chloro-2-nitrophenoxy)-N-methylbenzene)propanamine fumarate a) [(3R)-3-(5-Chloro-2-nitrophenoxy)-3-phenylpropyl]methylcarbamic acid, 1,1-dimethylethyl ester This was prepared by the method of Example 20(a) using [(3S)-3-hydroxy-3-phenylpropyl]methylcarbamic acid 1,1-dimethylethyl ester and 5-chloro-2-nitrophenol.

APCI+ve $^m$/z 32 1/323 [(M-BOC+H)$^+$].

b) (R)-γ-(5-Chloro-2-nitrophenoxy)-N-methylbenzene)propanamine fumarate

This was prepared by the method of Example 20(b), the product being isolated as the fumarate salt.

MS APCI+ve $^m$/z 321/323 [(M+H)$^+$].

$^1$H NMR 400 MHz (d$_6$-DMSO) 7.92 (1H, d), 7.45–7.39 (4H, m), 7.36–7.31 (1H, m), 7.27 (1H, d), 7.14 (1H, m), 6.46 (2H, s), 5.88 (1H, m), 2.96–2.86 (2H, m), 2.50 (3H, s), 2.29–2.19 (1H, m), 2.17–2.09 (1H, m).

EXAMPLE 82
4-Chloro-5-fluoro-2-{[(1R)-3-[(2-fluoroethyl)amino]-1-phenylpropyl]oxy}benzonitrile oxalate This was prepared by the method of Example 43(b) using 2-fluoroethylamine and 4-chloro-2-{[(1R)-3-chloro-1-phenylpropyl]oxy}-5-fluorobenzonitrile. The free base was converted into the oxalate salt.

MS APCI+ve $^m$/z 351 [(M+H)$^+$].

$^1$H NMR 400 MHz (d$_6$-DMSO) 8.02 (1H, d), 7.46–7.41 (5H, m), 7.38–7.33 (1H, m), 5.80–5.76 (1H, m), 4.73 (1H, t), 4.61 (1H, t), 3.4–3.2 (2H, m), 3.15–3.0 (2H, m), 2.4–2.3 (1H, m), 2.21–2.10 (1H, m).

EXAMPLE 83
2-[[(1R)-3-Amino-1-phenylpropyl]oxy]-4-bromo-5-fluorobenzonitrile oxalate a) 4-Bromo-2,5-difluorobenzaldehyde n-Butyllithium (1.95M in hexanes, 10.2 ml)) was added dropwise to a stirred solution of 1,4-dibromo-2,5-difluorobenzene (5 g, 18.4 mmol) in diethyl ether (60 ml) at −70° C. After 1 h, the solution was warmed to 0° C. over 1 h, diluted with water, the layers separated and the ether layer dried over sodium sulphate and evaporated. Purification by column chromatography (Biotage), eluting with 5% ethyl acetate/hexane, gave a yellow oil (1.82 g).

$^1$H NMR 300 MHz (CDCl$_3$) 10.28 (1H, s), 7.61 (1H, dd), 7.48 (1H, dd).

b) 4-Bromo-2,5-difluorobenzonitrile

4-Bromo-2,5-difluorobenzaldehyde (1.82 g, 8.3 mmol) and hydroxylamine-O-sulphonic acid (1.1 eq., 1.03 g) in water (40 ml) were heated to 100° C. for 6 h, cooled and extracted with ethyl acetate. The organic layer was dried (sodium sulphate) and evaporated to give the title compound as a pale yellow solid (1.2 g).

$^1$H NMR 300 MHz (CDCl$_3$) 7.51 (1H, t), 7.39 (1H, t).

(c) 4-Bromo-2-[[(1R)-3-chloro-1-phenylpropyl]oxy]-5-fluorobenzonitrile

This was prepared by the method of Example 43(a) using 4-bromo-2,5-difluorobenzonitrile and (R)-α-(2-chloroethyl)benzenemethanol.

$^1$H NMR 300 MHz (CDCl$_3$) 8.02 (1H, s), 7.42–7.26 (5H, m), 7.06–7.03 (1H, m), 5.46–5.43 (1H, m), 3.82–3.62 (1H, m), 3.75–3.60 (1H, m), 2.75–2.5 (1H, m), 2.55–2.30 (1H, m).

d) 2-[[(1R)-3-Azido-1-phenylpropyl]oxy]-4-bromo-5-fluorobenzonitrile

This was prepared by the method of Example 68(b) using 4-bromo-2-[[(1R)-3-chloro-1-phenylpropyl]oxy]-5-fluorobenzonitrile and sodium azide.

MS APCI+ve $^m$/z 351 [(M−N$_2$+H)$^+$].

e) 2-[[(1R)-3-Amino-1-phenylpropyl]oxy]-4-bromo-5-fluorobenzonitrile oxalate

This was prepared by the method of Example 77(b) using 2-[[(1R)-3-azido-1-phenylpropyl]oxy]-4-bromo-5-fluorobenzonitrile.

MS APCI+ve $^m$/z 349/350 [(M+H)$^+$].

$^1$H NMR 400 MHz (d$_6$-DMSO) 7.96 (1H, d), 7.48–7.40 (5H, m), 7.36–7.32 (1H, m), 5.79–5.75 (1H, dd), 2.95–2.82 (2H, m), 2.32–2.20 (1H, m), 2.10 (1H, m).

EXAMPLE 84
3-[[(3R)-3-(2,5-dichlorophenoxy)-3-phenylpropyl]amino]-1-propanol hydrochloride a) 1.4-Dichloro-2-[[(1R)-3-chloro-1-phenylpropyl]oxy]benzene, 2,5-Dichlorophenol (1.65 g) was subjected to the procedure described for Example 5(a) to afford the product as a clear oil (2.26 g).

$^1$H NMR 300 MHz (CDCl$_3$) 7.39–7.36 (5H, m), 7.24 (1H, s), 6.82 (1H, dd), 6.74 (1H, d), 5.40 (1H, dd), 3.93–3.80 (1H, m), 3.69–3.57 (1H, m), (2.33–2.18 (1H, m).

b) 1,4-Dichloro-2-[[(1R)-3-iodo-1-phenylpropyl]oxy]benzene,

The product from step (a) (2.26 g) was subjected to the procedure described for Example 5 (b) to afford the product as a yellow oil (2.78 g).

$^1$H NMR 300 MHz (CDCl$_3$) 7.39–7.36 (5H, m), 7.25–7.23 (1H, m), 6.84–6.80 (1H, m). 6.76–6.73 (1H, m), 5.32–5.25 (1H, m), 3.50–3.39 (1H, m), 3.33–3.24 (1H, m), 2.60–2.49 (1H, m), 2.39–2.26 (1H, m).

c) 3-[[(3R)-3-(2,5-Dichlorophenoxy)-3-phenylpropyl]amino]-1-propanol hydrochloride The product of step (b) (0.2 g) and 3-amino-propanol (0.11 g) were dissolved in dimethylformamide (4 ml) and stirred for 24 h. The reaction was poured into water and extracted into ethyl acetate. The organic extract was washed with brine, dried over magnesium sulphate and evaporated to dryness and triturated with 1N HCl in ether to give the product as a white solid.

MS APCI+ve $^m$/z 354 [(M+H)$^+$].

$^1$NMR (d$_6$-DMSO) 8.76 (1H, s), 7.50–7.37 (6H, m), 7.09 (1H, d), 6.99 (1H, dd), 5.77 (1H, dd), 4.73 (1H, s), 3.47 (2H, t), 3.11–2.91 (4H, m), 2.39–2.26 (1H, m), 2.26–2.14 (1H, m), 1.80–1.67 (2H, m).

EXAMPLE 85
1-[(3R)-3-(2,5-Dichlorophenoxy)-3-phenylpropyl]-4-piperidinemethanol hydrochloride The product of Example 84(b) (0.2 g) and 4-piperidinemethanol (0.11 g) were subjected to the procedure described in Example 84(c) to give the product as a white solid.

MS APCI+ve $^m$/z 394 [(M+H)$^+$].

$^1$H NMR 300 MHz (d$_6$-DMSO) 9.97 (1H, s), 7.48–7.28 (6H, m), 7.11 (1H, d), 6.99 (1H, dd), 5.77–5.67 (1H, m), 4.68–4.58 (1H, m), 3.56–3.44 (2H, m)m 3.28–3.20 (2H, m), 3.19–3.07 (2H, m), 2.99–2.83 (2H, m), 1.86–1.74 (2H, m), 1.68–1.53 (1H, m), 1.51–1.35 (2H, m), 2.44–2.24 (2H, m).

EXAMPLE 86
N-[(3R)-3-(2,5-Dichlorophenoxy)-3-phenylpropyl]-2-thiophenemethanamine hydrochloride The product of Example 84(b) (0.2 g) and 2-thiophenemethanamine (0.06) were subjected to the procedure described in Example 84(c) to give the product as a white solid.

MS APCI+ve $^m$/z 392 [(M+H)$^+$].

$^1$H NMR 400 MHz (d$_6$-DMSO) 9.40–9.24 (2H, m), 7.63 (1H, dd), 7.49–7.36 (5H, m), 7.36–7.28 (2H, m), 7.12–7.05 (2H, m), 7.03–6.95 (1H, m), 5.83–5.74 (1H, m), 4.46–4.37 (2H, m), 3.16–2.97 (2H, m), 2.40–2.29 (1H, m), 2.28–2.18 (1H, m).

EXAMPLE 87
N-[(3R)-3-(2,5-dichlorophenoxy)-3-phenylpropyl]-5-methyl-2-furanmethanamine hydrochloride The product of Example 84(b) (0.2 g) and 5-methyl-2-furanmethanamine (0.06 g) were subjected to the procedure described in Example 84(c) to give the product as a white solid.

MS APCI+ve $^m$/z 390 [(M+H)$^+$].

$^1$H NMR 300 MHz (d$_6$-DMSO) 9.36–9.17 (2H, m), 7.51–7.29 (6H, m), 7.10–7.04 (1H, m), 7.02–6.94 (1H, m), 6.48 (1H, d), 6.12 (1H, dd), 5.82–5.71 (1H, m), 4.20 (2H, s), 3.12–2.94 (2H, m), 2.39–2.13 (2H, m), 2.26 (3H, s).

EXAMPLE 88
4-Chloro-2-[[(1R)-1-phenyl-3-(1-piperazinyl)propyl]oxy]benzonitrile dihydrochloride a) 1,1-Dimethylethyl 4-[(3R)-3-(5-chloro-2-cyanophenoxy)-3-phenylpropyl]-1-piperazinecarboxylate 4-Chloro-2-{[(1R)-3-chloro-1-phenylpropyl]oxy}benzonitrile (0.3 g) and 1,1-dimethylethyl piperazinecarboxylate (0.4 g) were subjected to the procedure described for Example 11 to give the product as a clear gum (0.35 g).

$^1$H NMR 400 MHz (CDCl$_3$) 7.45 (1H, d), 7.41–7.34 (5H, m), 6.92 (1H, dd), 6.86 (1H, d), 5.36 (1H, dd), 3.49–3.34 (4H, m), 2.62–2.21 (7H, m), 2.11–1.96 (1H, m), 1.47 (9H, d).

b) 4-Chloro-2-[[(1R)-1-phenyl-3-(1-piperazinyl)propyl]oxy]-benzonitrile dihydrochloride The product from step (a) (0.35 g) was stirred in 4M HCl in dioxane (10 ml) for 3 h, then poured into saturated sodium bicarbonate solution (100 ml) and extracted into ethyl acetate. The extract was evaporated to dryness and the residue triturated with 1N HCl in ether to give the product as a white solid.

MS APCI+ve $^m$/z 356 [(M+H)$^+$].

$^1$H NMR 400 MHz (d$_6$-DMSO) 9.81–9.42 (2H, m), 7.78 (1H, d), 7.53–7.25 (6H, m), 7.15 (1H, d), 5.99–5.84 (1H, m), 3.94–3.03 (12H, m).

EXAMPLE 89
5-Fluoro-2-[[(1R)-3-[(2-Hydroxyethyl)amino]-1-(3-isoxazolyl)propyl]oxy]-4-methyl-benzonitrile fumarate a) N-Methoxy-N-methyl-3-isoxazolecarboxamide, A mixture of 3-isoxazolecarboxylic acid (4.2 g), 4-dimethylaminopyridine (5.1 g), N,O-dimethylhydroxylamine hydrochloride (4.0 g), N-methylmorpholine (4.2 g) and 1-(3-diethylaminopropyl)-3-ethylcarbodiimide hydrochloride (7.5 g) in dichloromethane (175 ml) were stirred at ambient temperature overnight. The reaction mixture was then washed with 2N hydrochloric acid (100 ml), saturated sodium bicarbonate (100 ml), brine, dried over magnesium sulphate and evaporated to give the product as a dark orange oil (3.7 g).

$^1$H NMR 300 MHz (CDCl$_3$) 8.48 (1H, d), 6.72 (1H, br s), 3.8 (3H, s), 3.4 (3H, s).

b) 1-(3-Isoxazolyl)-2-propen-1-one

The product of step (a) (0.66 g) was dissolved in dry tetrahydrofuran (20 ml), under a nitrogen atmosphere and cooled to −30° C. A solution of vinyl magnesium bromide (1M, 6 ml) was added dropwise over 5 minutes and the reaction mixture was allowed to warm to 0° C. and stirred at this temperature for 2 h. The mixture was then poured into ice-cold 2N hydrochloric acid (50 ml) and extracted into ethyl acetate. The extract was washed with water, brine, dried over magnesium sulphate and evaporated to give a dark oil (0.4 g).

$^1$H NMR 300 MHz (CDCl$_3$) 8.53–8.48 (1H, m), 7.36–7.22 (1H, m), 6.88–6.81 (1H, m), 6.76–6.64 (1H, m), 6.07–6.00 (1H, m).

c) 3-Chloro-1-(3-isoxazolyl)-1-propanone

The product of step (b) was treated with 1M HCl in ether (5 ml) and stirred for 4 h at ambient temperature. The solvent was then removed under reduced pressure to leave the product as a dark gum (0.42 g).

$^1$H NMR 300 MHz (CDCl$_3$) 8.51 (1H, d), 6.79 (1H, d), 3.92 (2H, t), 3.57 (2H, t).

d) (S)-α-(2-Chloroethyl)-3-isoxazolemethanol

The product of step (c) (1 g) was reduced by the procedure described in Example 68(a) to give the product as a clear oil (0.5 g).

$^1$H NMR 300 MHz (CDCl$_3$) 8.47–8.36 (1H, m), 6.43–6.38 (1H, m), 5.18 (1H, dt), 3.87–3.75 (1H, m), 3.73–3.62 (1H, m), 2.71–2.61 (1H, m), 2.36–2.18 (2H, m).

e) 2-[[(1R)-3-Chloro-1-(3-isoxazolyl)propyl]oxy]-5-fluoro-4-methyl-benzonitrile

The product of step (d) (0.47 g) was reacted with 5-fluoro-2-hydroxy-4-methylbenzonitrile using the procedure described for Example 5(a) to afford the product as a white solid (0.4 g).

$^1$H NMR 300 MHz (CDCl$_3$) 8.42 (1H, t), 7.18 (1H, d), 6.94 (1H, d), 6.47 (1H, d), 5.78 (1H, dd), 3.97–3.82 (1H, m), 3.80–3.67 (1H, m), 2.73–2.56 (1H, m), 2.43–2.29 (1H, m), 2.31 (3H, s).

f) 5-Fluoro-2-[[(1R)-3-[(2-hydroxyethyl)amino]-1-(3-isoxazolyl)propyl]oxy]-4-methyl-benzonitrile fumarate The product of step (e) (0.16 g) was reacted with ethanolamine (0.3 g) using the procedure described for Example 11 to afford the product as a white solid (0.14 g).

MS APCI+ve $^m$/z 320 [(M+H)$^+$].

$^1$H NMR 300 MHz (d$_6$-DMSO) 8.97 (1H, s), 7.67 (1H, d), 7.26 (1H, d), 6.68 (1H, s), 6.48 (2H, s), 5.93 (1H, s), 3.60 (2H, s), 2.96 (4H, d), 2.47–2.35 (1H, m), 2.33–2.10 (4H, m).

EXAMPLE 90

2-[[(1R)-3-Amino-1-(3-isoxazolyl)propyl]oxy]-5-fluoro-4-methyl-benzonitrile fumarate a) 2-[[(1R)-3-Azido-1-(3-isoxazolyl)propyl]oxy]-5-fluoro-4-methyl-benzonitrile The product of Example 89(e) (0.2 g) and sodium azide (0.045 g) in dimethylsulphoxide (5 ml) were heated at 60° C. for 24 h to give the product.

MS APCI+ve $^m/z$ 274 [(M−28)$^+$].

b) 2-[[(1R)-3-Amino-1-(3-isoxazolyl)propyl]oxy]-5-fluoro-4-methyl-benzonitrile fumarate The solution produced in step (a) was treated with tetrahydrofuran (10 ml), water (1 ml) and triphenylphosphine (0.3 g) and stirred at ambient temperature for 36 h. The mixture was poured into saturated sodium bicarbonate (20 ml) and extracted into ethyl acetate. The extract was evaporated to dryness and the residue loaded onto an ion exchange resin (SCX isolute) and washed with acetonitrile and methanol. The product was eluted off the column with 7M ammonia in methanol to give an oil which was converted into the fumarate salt (0.104 g).

MS APCI+ve $^m/z$ 276 [(M+H)$^+$].

$^1$H NMR 300 MHz (d$_6$-DMSO) 8.97 (1H, d), 7.68 (1H, d), 7.24 (1H, d), 6.68 (1H, d), 6.41 (2H, s), 5.99–5.85 (1H, m), 3.01–2.89 (2H, m), 2.43–2.29 (1H, m), 2.27–2.16 (1H, m), 2.24 (3H, s).

EXAMPLE 91

4-Chloro-2-[[(1R)-3-[(1,1-dimethylethyl)amino]-1-(3-isoxazolyl)propyl]oxy]benzonitrile fumarate a) (R)-α-(2-Chloroethyl)-3-isoxazolemethanol The product from Example 89(c) (3 g) was reduced using the procedure described in Example 66(c) to give the product as clear oil (1,1 g).

$^1$H NMR 300 MHz (CDCl$_3$) 8.40 (1H, d), 6.40 (1H, d), 5.25–5.13 (1H, m), 3.88–3.61 (2H, m), 2.42 (1H, d), 2.33–2.21 (2H, m).

b) 4-Chloro-2-[[(1R)-3-chloro-1-(3-isoxazolyl)propyl]oxy]benzonitrile

The product of step (a) (0.19 g) and 2-fluoro-4-chlorobenzonitrile (0.17 g) were dissolved in dimethylformamide (5 ml) and treated with sodium hydride (60% dispersion in oil, 0.06 g). After 2 h, the reaction was poured into 2N hydrochloric acid (10 ml) and extracted into ethyl acetate (50 ml). The extract was washed with saturated sodium bicarbonate, brine, dried over magnesium sulphate and evaporated down to a yellow oil (0.29 g).

MS APCI+ve $^m/z$ 298 [(M+H)$^+$].

$^1$H NMR 300 MHz (CDCl$_3$) 8.44 (1H, d), 7.49 (1H, d), 7.13 (1H, d), 7.04 (1H, dd), 6.46 (1H, d), 5.82 (1H, dd), 3.88 (1H, ddd), 3.73 (1H, dt), 2.73–2.57 (1H, m), 2.47–2.26 (1H, m).

c) 4-Chloro-2-[[(1R)-3-[1,1-dimethylethyl)amino]-1-(3-isoxazolyl)propyl]oxy]benzonitrile fumarate The product from step (b) (0.14 g) and tert-butylamine (0.5 g) were reacted using the procedure described for Example 12 to afford the product as a white solid (0.085 g).

MS APCI+ve $^m/z$ 334 [(M+H)$^+$].

$^1$H NMR 300 MHz (d$_6$-DMSO) 8.96 (1H, d), 7.77 (1H, d), 7.40 (1H, d), 7.20 (1H, dd), 6.71 (1H, t), 6.46 (2H, s), 6.15–5.90 (1H, m), 2.95 (2H, t), 2.45–2.34 (1H, m), 2.33–2.19 (1H, m), 1.22 (9H, s).

EXAMPLE 92

2-[[(1R)-3-Amino-1-(3-isoxazolyl)propyl]oxy]-4-chloro-benzonitrile fumarate a) 2-[[(1R)-3-Azido-1-(3-isoxazolyl)propyl]oxy]-4-chloro-benzonitrile The product of Example 91(b) was subjected to the procedure in Example 90(a) to afford the product which was then carried on directly to the next step.

b) 2-[[(1R)-3-Amino-1-(3-isoxazolyl)propyl]oxy]-4-chloro-benzonitrile fumarate

The product of step (a) (0.14 g) was subjected to the procedure described in Example 90 (b) to afford the product as a white solid (0.05 g).

MS APCI+ve $^m/z$ 278 [(M+H)$^+$].

$^1$H NMR 300 MHz (d$_6$-DMSO) 8.99 (1H, d), 7.81 (1H, d), 7.41 (1H, d), 7.23 (1H, dd), 6.72 (1H, d), 6.41 (2H, s), 6.08 (1H, dd), 2.95 (2H, t), 2.44–2.31 (1H, m), 2.31–2.19 (1H, m).

EXAMPLE 93

2-[[(1R)-3-Amino-1-(3-isoxazolyl)propyl]oxy]-4-chloro-5-fluoro-benzonitrile a) (R)-α-(2-Azidoethyl)-3-isoxazolemethanol, The product from Example 91(a) (0.17 g) and sodium azide (0.08 g) were heated in dimethylsulphoxide (3 ml) at 70° C. for 4 h. The mixture was then poured into water and extracted with ethyl acetate. The extract was washed with water, brine, dried over magnesium sulphate and evaporated to give the product as a clear oil (0.15 g).

MS APCI+ve $^m/z$ 141 [(M−28)$^+$].

$^1$H NMR 300 MHz (CDCl$_3$) 8.47 (1H, d), 6.50 (1H, d), 5.18–4.98 (1H, m), 3.72–3.40 (2H, m), 2.70–2.47 (1H, m), 2.16–1.98 (2H, m).

b) 2-[[(1R)-3-Azido-1-(3-isoxazolyl)propyl]oxy]-4-chloro-5-fluorobenzonitrile

The product from step (a) (0.1 g) and 2,5-difluoro-4-chloro-benzonitrile (0.18 g) and sodium hydride (60% dispersion in oil, 0.035 g) were subjected to the procedure described in Example 90(a) to afford the product as a gum (0.15 g).

MS APCI+ve $^m/z$ 294 [(M−28)$^+$].

c) 2-[[(1R)-3-Amino-1-(3-isoxazolyl)propyl]oxy]-4-chloro-5-fluoro-benzonitrile fumarate The product from step (b) (0.15 g) and triphenylphosphine (0.3 g) were subjected to the procedure described in Example 90(b) to afford the product as a solid (0.105 g).

MS APCI+ve $^m/z$ 296 [(M+H)$^+$].

$^1$H NMR 300 MHz (d$_6$-DMSO) 8.99 (1H, d), 8.04 (1H, d), 7.61 (1H, d), 6.74–6.68 (1H, m), 6.40 (2H, s), 6.09–6.00 (1H, m), 3.00–2.89 (2H, m), 2.43–2.32 (1H, m), 2.29–2.18 (1H, m).

EXAMPLE 94

(R)-γ-(2,5-Dichlorophenoxy)-3-isoxazolepropanamine fumarate a) 3-[(1R)-3-Azido-1-(2,5-dichlorophenoxy)propyl]isoxazole The product from Example 93(a) (0.17 g) was reacted with 2,5-dichloro-fluorobenzene (0.4 g) using the procedure described in Example 93(b) to afford the product as a gum which was carried on to the next step.

b) (R)-γ-(2,5-Dichlorophenoxy)-3-isoxazolepropanamine fumarate

The product from step (a) (0.1 g) was subjected to the procedure described in Example 90(b) to afford the product as a solid (0.03 g).

MS APCI+ve $^m/z$ 287 [(M+H)$^+$].

$^1$H NMR 300 MHz (CD$_3$OD) 8.72 (1H, d), 7.39 (1H, d), 7.13 (1H, d), 7.02 (1H, dd), 6.70 (2H, s), 6.56 (1H, d), 5.86–5.77 (1H, m), 3.28–3.19 (2H, m), 2.60–2.46 (1H, m), 2.43–2.28 (1H, m).

Screens

The pharmacological activity of compounds according to the invention was tested in the following screens.

Screen 1

The activity of compounds of formula (I), or a pharmaceutically acceptable salt, enantiomer or racemate thereof, may be screened for nitric oxide synthase inhibiting activity by a procedure based on that of Förstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 MM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% $CO_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 μl of substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 mCi L-[$^3$H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled L-citrulline is separated from labelled L-arginine using Dowex AG-50W. 150 μl of a 25% aqueous slurry of Dowex 50W (Na$^+$ form) is added to the assay after which the whole is filtered into 96 well plates. 75 μl of filtrate is sampled and added to wells of 96 well plates containing solid scintillant. After allowing the samples to dry the L-citrulline is quantified by scintillation counting.

In a typical experiment basal activity is 300 dpm per 75 μl sample which is increased to 1900 dpm in the reagent controls. Compound activity is expressed as IC$_{50}$ (the concentration of drug substance which gives 50% enzyme inhibition in the assay) and aminoguanidine, which gives an IC$_{50}$ (50% inhibitory concentration) of 10 μM, is tested as a standard to verify the procedure. Compounds are tested at a range of concentrations and from the inhibitions obtained IC$_{50}$ values are calculated. Compounds that inhibit the enzyme by at least 25% at 100 μM are classed as being active and are subjected to at least one retest.

Screen 2

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10%(v/v) foetal bovine serum, and 2 mM L-glutamine, at 37° C. in 5% $CO_2$ Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% $CO_2$ in RPMI 1640 containing 100 μM L-arginine and 100 μM verapamil-HCl in the presence and absence of test compounds.

Nitrite accumulation was determined by mixing an equal volume of culture media with Griess reagent (10 mg/ml sulphanilamide, 1 mg-N-(1-naphthyl)ethylenediamine in 1 ml 2.5% (v/v) phosphoric acid). Inhibition in the presence of compounds was calculated relative to the nitrite levels produced by untreated cells. IC$_{50}$ values were estimated from a semi-log plot of % inhibition versus concentration of compound.

When tested, the compounds of Examples 1 to 94 gave IC$_{50}$ values of less than 25 μM in at least one of the above screens, indicating that they are predicted to show useful therapeutic activity.

What is claim is:

1. A compound of formula (Ia)

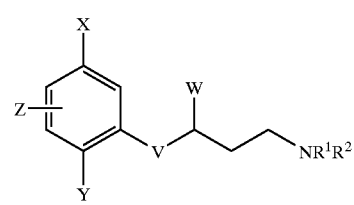

(I)

wherein

X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;

m and p independently represent an integer 0, 1 or 2;

Z represents H or fluoro;

V represents O;

W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a 4 to 8 membered saturated azacyclic ring optionally incorporating one further heteroatom selected from O, S or $NR^8$; said ring being substituted by OH or by C1 to 4 alkyl substituted by C1 to 4 alkoxy, OH or $NR^9R^{10}$;

or the group $NR^1R^2$ together represents part of a five membered aromatic azacyclic ring optionally incorporating one further N atom;

$R^4$, $R^5R^6$, $R^7$, $R^9$ and $R^{10}$ independently represent H or C1 to 4 alkyl;

$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

$R^{11}$ and $R^{12}$ independently represent H or C1 to 4 alkyl;

or a pharmaceutically acceptable salt, enantiomer or racemate thereof, with the proviso that when W represents optionally substituted phenyl, thienyl, furanyl or pyrrolyl and $R^1$ represents H, C1 to 4 alkyl or C3 to 6 cycloalkyl optionally substituted by C1 to 4 alkoxy, then $R_2$ does not represent H, C1 to 4 alkyl or C3 to 6 cycloalkyl optionally substituted by C1 to 4 alkoxy; and with the proviso that when W represents thiazolyl or pyridyl, then either Z represents F; or at least one of X and Y represents CN; or $R^1$ and $R_2$ do not independently represent H or $CH_3$.

2. A compound of formula (1a), according to claim 1, wherein X and Y independently represent Br, Cl, $CH_3$, $CF_3$ or CN.

3. A compound of formula (1a), according to claim 1, wherein W represents an optionally substituted five or six membered aromatic heterocyclic ring containing 1 to 3 heteroatoms independently selected from O, S and N.

4. A compound of formula (1a), according to claim 1, wherein $R^1$ and $R^2$ independently represent H or methyl.

5. A compound selected from the group consisting of:

2-[[(3R)-3-(2,5-dichlorophenoxy)-3-(2-thienyl)propyl]amino]ethanol;

4-chloro-2-{[(1R)-3-(4-hydroxy-1-piperidinyl)-1-phenylpropyl]oxy}-benzonitrile;

4-chloro-2-{[(1R)-3-[(2-hydroxyethyl)methylamino]-1-phenylpropyl]oxy}-benzonitrile;

4-chloro-2-{[(1R)-3-[(3R)-3-hydroxypyrrolidinyl]-1-phenylpropyl]oxy}-benzonitrile;

4-chloro-2-{[(1R)-3-[(3S)-3-hydroxypyrrolidinyl]-1-phenylpropyl]oxy}-benzonitrile;

4-chloro-5-fluoro-2-[3-(methylamino)-1-(2-pyrimidyl)propoxy]benzonitrile;

4-chloro-5-fluoro-2-({(1R)-3-[(3-hydroxypropyl)amino]-1-phenylpropyl}oxy)benzonitrile;

4-chloro-5-fluoro-2-[[(1R)-1-(3-furanyl)-3-(3-hydroxypropyl)amino]propyl]oxy}benzonitrile;

4-chloro-5-fluoro-2-{[(1R)-3-[(3-hydroxypropyl)amino]-1-(3-thienyl)propyl]oxy}benzonitrile;

4-bromo-5-fluoro-2-({(1R)-3-[(3-hydroxypropyl)amino]-1-phenylpropyl}oxy)benzonitrile;

4-bromo-5-fluoro-2-({(1R)-1-(3-furanyl)-3-[(3-hydroxypropyl)amino]propyl}oxy)benzonitrile;

4-bromo-5-fluoro-2-{[(1R)-3-[(3-hydroxypropyl)amino]-1-(3-thienyl)propyl]oxy}benzonitrile;

4-chloro-5-fluoro-2-[[(1R)-3-[[(5-methylpyrazinyl)methyl]amino]-1phenylpropyl]oxy]benzonitrile;

4-chloro-5-fluoro-2-[[(1R)-3-[(1H-imidazol-2-ylmethyl)amino]-1-phenylpropyl]oxy]benzonitrile;

4-chloro-2-[[(1R)-3-[[2-(dimethylamino)ethyl]amino]-1-phenylpropyl]oxy]-5-fluoro benzonitrile;

4-chloro-5-fluoro-2-[[(1R)-3-[[2-(4-morpholinyl)ethyl]amino]-1-phenylpropyl]oxy]benzonitrile;

4-chloro-5-fluoro-2-[[(1R)-3-[[2-(1H-imidazol-1-yl)ethyl]amino]-1-phenylpropyl]oxy]benzonitrile;

4-chloro-5-fluoro-2-[[(1R)-3-[[2-(1H-imidazol-4-yl)ethyl]amino]-1-phenylpropyl]oxy]benzonitrile;

4-chloro-5-fluoro-2-[[(1R)-3-[(2-hydroxyethyl)amino]-1-phenylpropyl]oxy]benzonitrile;

2-[[(1R)-3-[(2-aminoethyl)amino]-1-phenylpropyl]oxy]-4-chloro-5-fluorobenzonitrile;

4-chloro-5-fluoro-2-[[(1R)-1-phenyl-3-[(3,3,3-trifluoropropyl)amino]propyl]oxy]benzonitrile;

2-{[(1R)-3-amino-1-(2-thiazolyl)propyl[oxy}-4-chlorobenzonitrile;

4-chloro-2-{[(1R)-3-(methylamino)-1-(2-thiazolyl)propyl]oxy}benzonitrile;

2-[3-amino-1-(2-oxazolyl)propoxyl]-4-chlorobenzonitrile;

γ-(2,5-dichlorophenoxy)-2-oxazolepropanamine;

2-[[-3-amino-1-(3-pyridinyl)propyl]oxy]-4-chloro-5-fluorobenzonitrile;

4-chloro-5-fluoro-2-[3-(methylamino)-1-(3-pyridinyl)propoxy]benzonitrile;

2-[3-amino-1-(6-methoxy-2-pyridinyl)propoxy]-4-chloro-5-fluorobenzonitrile;

2-[3-amino-1-(1,6-dihydro-6-oxo-2pyridinyl)propoxy]-4-chloro-5-fluorobenzonitrile;

2-[3-amino-1-(6-bromo-3-pyridinyl)propoxy]-4-chlorobenzonitrile;

2-[[3-amino-1-(5-isoxazolyl)propyl]oxy]-4-chlorobenzonitrile;

4-chloro-2-[3-[(2-hydroxyethyl)amino]-1-(5-isoxazolyl)propoxy]benzonitrile;

(R)-γ-(2,5-dichlorophenoxy)-5-isoxazolepropanamine;

4-chloro-5-fluoro-2-[[(1R)-3-[(2-hydroxyethyl)amino]-1-(3-thienyl)propyl]oxy]benzonitrile;

2-[[(1R)-3-[(2-aminoethyl)amino]-1-(3-thienyl)propyl]oxy]-4-chloro-5-fluoro-benzonitrile;

4-chloro-2-[3-(methylamino)-1-(2-thiazolyl)propoxy]-benzonitrile;

2-[[(1R)-3-amino-1-(2-thiazolyl)propyl]oxy]-4-chloro-5-fluoro-benzonitrile;

4-chloro-5-fluoro-2-{[(1R)-3-[(2-fluoroethyl)amino]-1-phenylpropyl]oxy}benzonitrile;

3-[[(3R)-3-(2,5-dichlorophenoxy)-3-phenylpropyl]amino]-1-propanol;

1-[(3R)-3-(2,5-dichlorophenoxy)-3-phenylpropyl]-4-piperidinemethanol;

N-[(3R)-3-(2,5-dichlorophenoxy)-3-phenylpropyl]-2-thiophenemethanamine;

N-[(3R)-3-(2,5-dichlorophenoxy)-3-phenylpropyl]-5-methyl-2-furanmethanamine;

5-fluoro-2-[[(1R)-3-[(2-hydroxyethyl)amino]-1-(3-isoxazolyl)propyl]oxy]-4-methyl-benzonitrile;

2-[[(1R)-3-amino-1-(3-isoxazolyl)propyl]oxy]-5-fluoro-4-methyl-benzonitrile;

4-chloro-2-[[(1R)-3-[(1,1-dimethylethyl)amino]-1-(3-isoxazolyl)propyl]oxy]benzonitrile;

2-[[(1R)-3-amino-1-(3-isoxazolyl)propyl]oxy]-4-chloro-benzonitrile;

2-[[(1R)-3-amino-1-(3-isoxazolyl)propyl]oxy]-4-chloro-5-fluoro-benzonitrile;

(R)-γ-(2,5-dichlorophenoxy)-3-isoxazolepropanamine;

2-[[(1R)-3-amino-1-(3-isoxazolyl)propyl]oxy]-4-(trifluoromethyl)-benzonitrile;

2-[[(1R)-3-amino-1-(5-methyl-3-isoxazolyl)propyl]oxy]-4-chloro-5-fluoro-benzonitrile; or pharmaceutically acceptable salts thereof, enantiomers thereof and racemates thereof.

6. A pharmaceutical composition comprising a compound of formula (Ia) according to claim 1, or a pharmaceutically acceptable salt, enantiomer or racemate thereof, in admixture with a pharmaceutically acceptable adjuvant, diluent or carrier.

\* \* \* \* \*